(12) United States Patent
Skanderup et al.

(10) Patent No.: US 11,993,819 B2
(45) Date of Patent: May 28, 2024

(54) METHOD OF DETERMINING A RISK OF CANCER

(71) Applicant: Agency for Science, Technology and Research, Singapore (SG)

(72) Inventors: Anders Skanderup, Singapore (SG); Yu Amanda Guo, Singapore (SG); Sarah Ng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 34 days.

(21) Appl. No.: 16/977,197

(22) PCT Filed: Mar. 1, 2019

(86) PCT No.: PCT/SG2019/050119
§ 371 (c)(1),
(2) Date: Sep. 1, 2020

(87) PCT Pub. No.: WO2019/168478
PCT Pub. Date: Jun. 6, 2019

(65) Prior Publication Data
US 2021/0155991 A1 May 27, 2021

(30) Foreign Application Priority Data
Mar. 1, 2018 (SG) .......................... 10201801692U

(51) Int. Cl.
*C12Q 1/6886* (2018.01)
*C12Q 1/6827* (2018.01)

(52) U.S. Cl.
CPC .......... *C12Q 1/6886* (2013.01); *C12Q 1/6827* (2013.01)

(58) Field of Classification Search
CPC ............................ C12Q 1/6886; C12Q 1/6827
See application file for complete search history.

(56) References Cited

FOREIGN PATENT DOCUMENTS

WO    WO-0142504 A2 *   6/2001   ........... C12Q 1/6886

OTHER PUBLICATIONS

Supplement Table 4 of Katainen et al. Nature Genetics. 2015. 47(7):818-821. (Year: 2015).*
Stephens. The Mutational Spectra of Cancer Genes in TCGA Data. May 10, 2017. Retrieved on Apr. 27, 2022 from the internet: https://www.cancer.gov/research/key-initiatives/ras/ras-central/blog/2017/cancer-mutation-spectra. (Year: 2017).*
Xie et al. Genomics. 2014. 104:234-241 and Supplementary Data. (Year: 2014).*
Wang et al. Nature Genetics. 2014. 46:573-582. (Year: 2014).*
Supporting Information for Wang et al. Nature Genetics. 2014. 46:573-582. (Year: 2014).*
Guo, et al., *Mutation Hotspots at CTCF Binding Sites Coupled to Chromosomal Instability in Gastrointestinal Cancers*, Nature Communications, vol. 9, No. 1, Apr. 18, 2018, 14 pages.
Katainen et al., *CTCF/cohesin-binding sites are frequently mutated in cancer*, Nature Genetics, vol. 47, No. 7, Jun. 8, 2015, pp. 818-821.
Umer, et al., *A Significant Regulatory Mutation Burden at a High-Affinity Position of the CTCF Motif in Gastrointestinal Cancers*, Human Mutation, vol. 37, No. 9, May 13, 2016, pp. 904-913.
International Application No. PCT/SG2019/050119 received and International Preliminary Report on Patentability dated Sep. 1, 2020, 9 pages.
Singapore Application No. 11202006997S received an International Search Report and Written Opinion dated Feb. 24, 2022, all pages.
Gua, et al., *Mutation Hotspots at CTCF Binding Sites Coupled to Chromosomal Instability in Gastrointestinal Cancers*, Nature Communications, vol. 9, No. 1, Apr. 18, 2018, 14 pages.
Hnisz, et al., *Activation of Proto-Oncogenes by Disruption of Chromosome Neighborhoods*, Science, vol. 351, No. 6280, Mar. 25, 2016, 5 pages.
Piraino, et al., *Identification of 1-15 Coding and Non-Coding Mutational Hotspots in Cancer Genomes*, BMC Genomics, Biomed Central Ltd, London, UK, vol. 18, No. 1, Jan. 5, 2017, 17 pages.
Umer et al., A Significant 1-15 *Regulatory Mutation Burden at a High-Affinity Position of the CTCF Motif in Gastrointestinal Cancers*, Human Mutation, vol. 37, No. 9, Jun. 2, 2016.
European Application No. 19 76 1335 received an Extended Search Report, dated Nov. 5, 2021, 10 pages.
Cancer Genome Atlas Research Network, Comprehensive molecular characterization of gastric adenocarcinoma. *Nature*, Jul. 23, 2014, vol. 513, No. 7517, pp. 202-209.
Lee J-H. et al, Genetic variants and risk of gastric cancer: a pathway analysis 3,10, 14 of a genome-wide association study. Springerplus, May 6, 2015, vol. 4, No. 215, pp. 1-6.
Liu J. et al, Identification and validation of colorectal neoplasia-specific methylation biomarkers based on CTCF-binding sites. Oncotarget, Dec. 11, 2017, vol. 8, No. 69, pp. 114183-114194.
Poulos R.C. et al, In search of non-coding driver mutations by deep sequencing of regulatory elements in colorectal cancer. bioRxiv, Jan. 16, 2018, pp. 249300.
Sandoval-Borquez A. et al, Noncoding Genomics in Gastric Cancer and the Gastric Precancerous Cascade: Pathogenesis and Biomarkers. Dis Markers, Aug. 26, 2015, vol. 2015, Article ID 503762, pp. 1-14.

(Continued)

*Primary Examiner* — Joseph G. Dauner
(74) *Attorney, Agent, or Firm* — Kilpatrick Townsend & Stockton LLP

(57) ABSTRACT

There is provided a method of determining a risk of gastrointestinal cancer in a human subject, the method comprising: determining in a biological sample of the subject, whether mutation is present in at least one CTCF-binding sites (CBS) overlapping regions, or portions or flanking sequences thereof, or at least one non-CBS regions, or portions or flanking sequences thereof, wherein presence of mutation in at least one CBS overlapping regions, or portions or flanking sequences thereof, and/or at least one non-CBS regions, or portions or flanking sequences thereof, is indicative of a risk of gastrointestinal cancer in the subject. There are also provided a method of treating gastrointestinal cancer in a human subject and related kits.

10 Claims, 34 Drawing Sheets

Specification includes a Sequence Listing.

(56) References Cited

OTHER PUBLICATIONS

Wong S.S. et al, Genomic landscape and genetic heterogeneity in gastric adenocarcinoma revealed by whole-genome sequencing. Nat Commun, Nov. 19, 2014, vol. 5, No. 5477, pp. 1-12.
International Patent Application No. PCT/SG2019/050119 received an International Search Report and Written Opinion dated May 28, 2019, 14 pages.
Office Action for Chinese Appln No. 201980016095.7 dated Dec. 18, 2023, all pages.

* cited by examiner

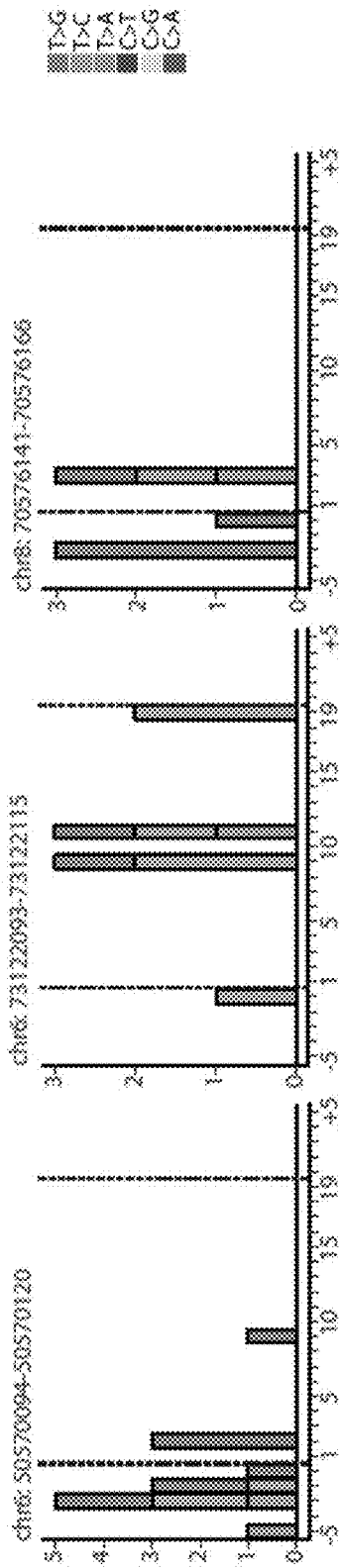
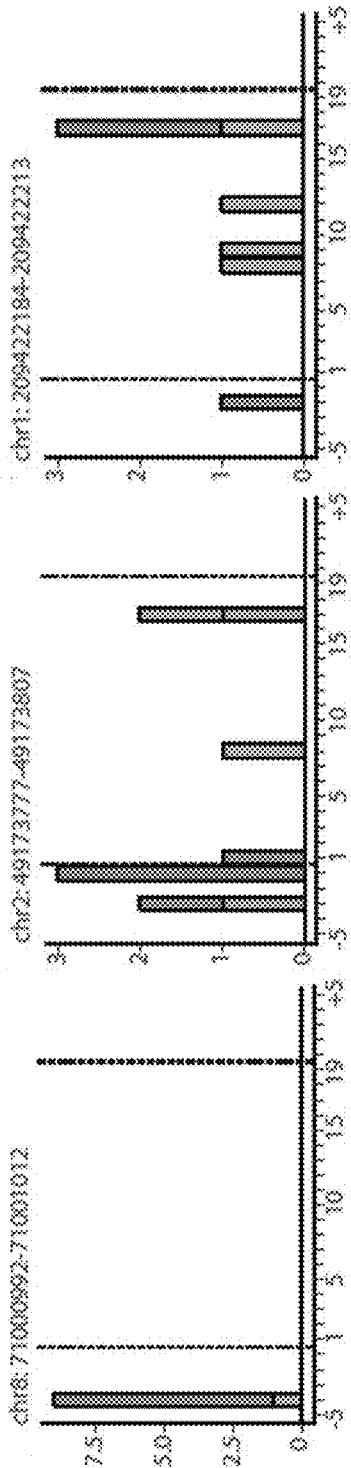
FIG. 14A  FIG. 14B  FIG. 14C
FIG. 14D  FIG. 14E  FIG. 14F

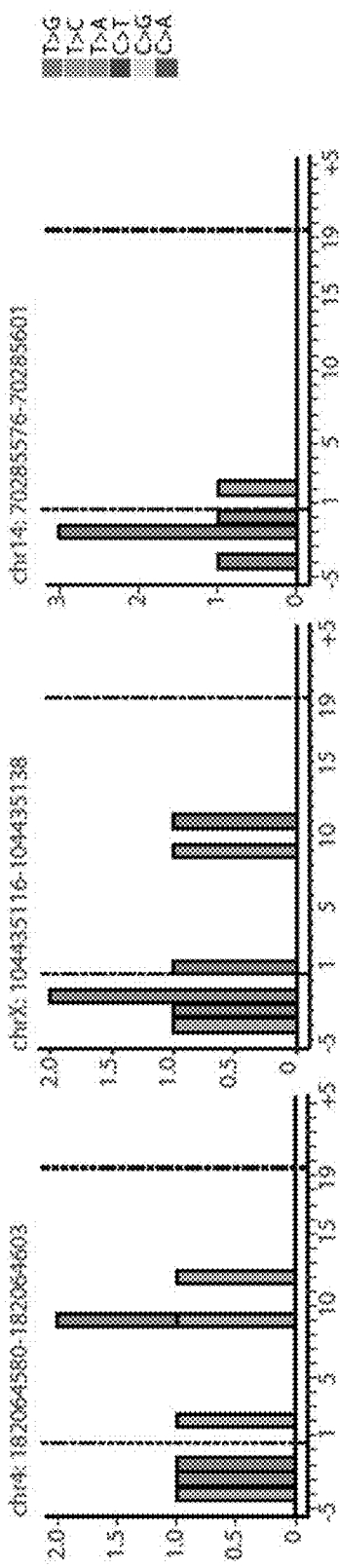
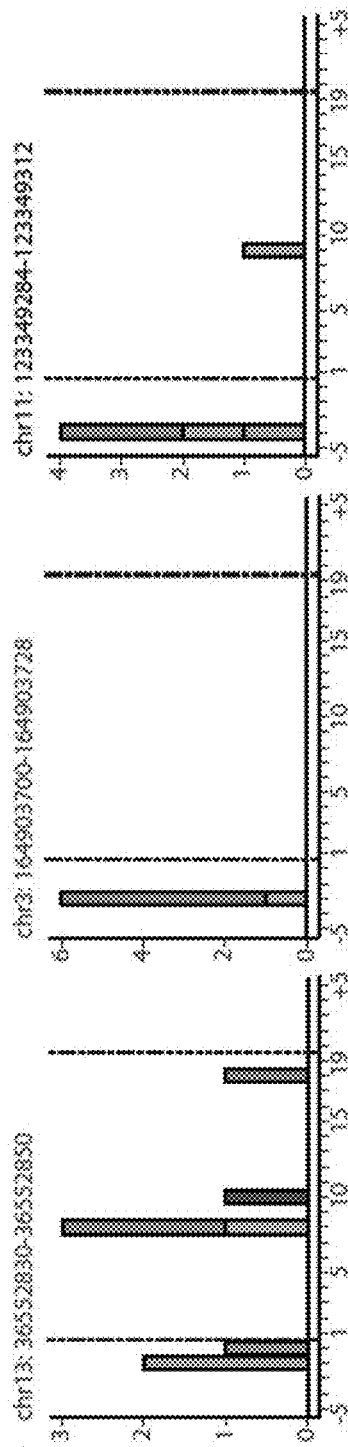
FIG. 14G  FIG. 14H  FIG. 14I
FIG. 14J  FIG. 14K  FIG. 14L

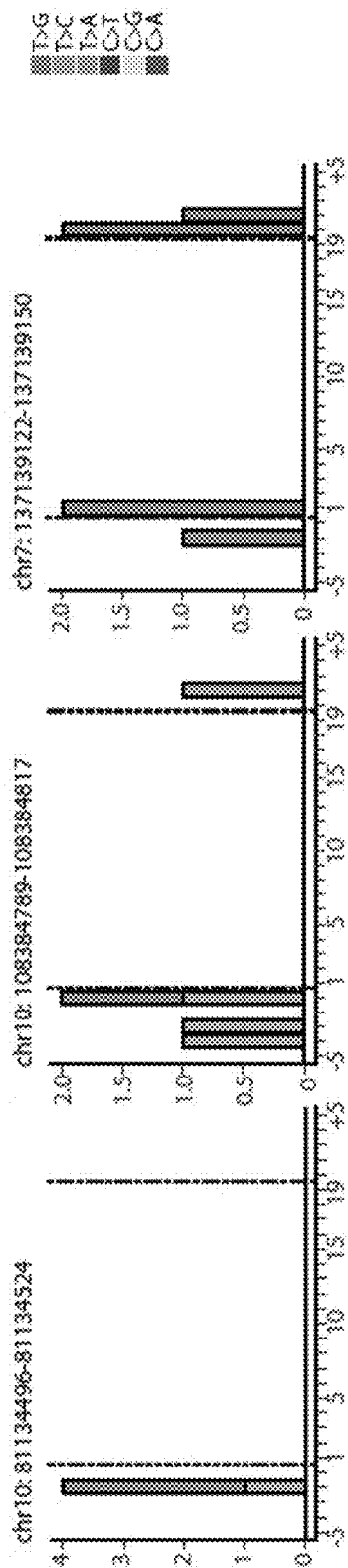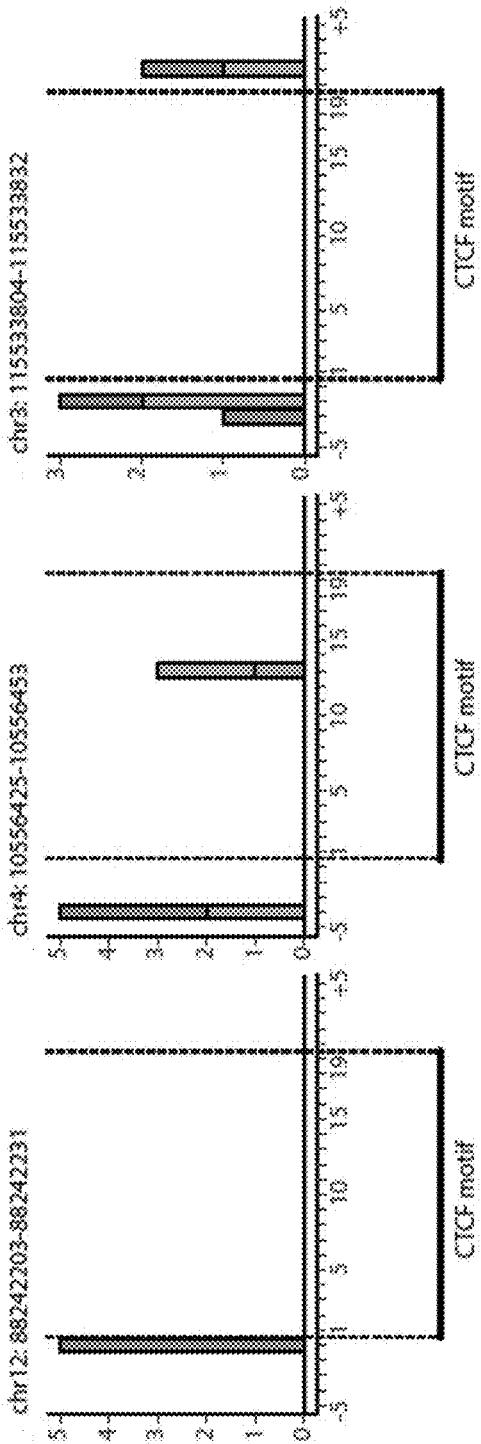
FIG. 14M  FIG. 14N  FIG. 14O
FIG. 14P  FIG. 14Q  FIG. 14R

METHOD OF DETERMINING A RISK OF CANCER

REFERENCE TO A SEQUENCE LISTING

The Sequence Listing written in file Sequence Name "U.S. Ser. No. 16/977,197", filed on Sep. 1, 2020 with the USPTO, 16.29 kilobytes, machine format IBM-PC, MS-Windows operating system, and the Sequence Listing written in file name "1210179-Revised_Sequence_Listing", filed on Mar. 9, 2022 with the USPTO, 17.7 kilobytes, machine format IBM-PC, MS-Windows operating system are both hereby incorporated by reference in their entireties for all purposes.

TECHNICAL FIELD

The present disclosure relates broadly to a method of determining a risk of cancer, a method of treating cancer and related polynucleotides and kits.

BACKGROUND

Non-coding DNA constitutes over 98% of the human genome and harbors numerous functional elements essential for regulating gene expression and maintaining chromosomal architecture. However, due to primarily reasons of cost, cancer genomics studies have so far been confined to profiling somatic DNA alterations in protein coding regions, largely ignoring the non-coding 98% of the human genome and >95% of the transcribed genome. Important non-coding regulatory regions such as gene promoters, enhancers, untranslated regions, and thousands of non-coding RNAs are therefore still largely an uncharted black box of the cancer genome.

Mutations at non-coding regions may drive cancer by dysregulating proto-oncogenes and tumor suppressor genes, as exemplified by recent studies demonstrating recurrent point mutations at the TERT promoter in multiple cancer types and TAL1 enhancer insertions in T-cell acute lymphoblastic leukemia. While previous pan-cancer analyses of tumor genomes have nominated regulatory driver mutations, these studies have typically not been sufficiently powered to identify tissue-specific non-coding driver mutations, as hundreds of samples are usually needed to reliably identify driver mutations in individual cancer types[6]. Recently, the whole genome mutational landscapes of breast, liver[8] and pancreatic[9] cancer tumors have been studied to identify cancer-specific non-coding drivers. However, the prevalence and impact of non-coding tissue specific driver mutations is still unknown for most other cancer types, including gastrointestinal cancers.

Comprehensive genetic and molecular profiling have identified new molecular subtypes and genetic drivers of gastrointestinal cancer/adenocarcinoma. Studies have also investigated the extent and impact of mutational signatures and epigenetic dysregulation in gastrointestinal cancer genomes. However, not all elements of the disease development of gastric cancer are known. As a leading cause of global cancer mortality, there is a need to provide additional understanding of the disease development/progression of gastrointestinal cancer.

Thus, there is a need to provide alternative methods of determining a risk of cancer, methods of treating cancer and related polynucleotides and kits.

SUMMARY

In one aspect, there is provided a method of determining a risk of gastrointestinal cancer in a human subject, the method comprising: determining in a biological sample of the subject, whether mutation is present in at least one of the CTCF-binding sites (CBS) overlapping regions set forth in the table below:

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or flanking sequences thereof, or at least one of the non-CBS regions set forth in the table below:

| Chromosome | Start site | End site |
|---|---|---|
| 7 | 68391104 | 68391132 |
| 7 | 136495924 | 136495948 |
| 2 | 57627616 | 57627640 |
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or flanking sequences thereof, wherein presence of mutation in at least one of the CBS overlapping regions, or portions or flanking sequences thereof, and/or at least one of the non-CBS regions, or portions or flanking sequences thereof, is indicative of a risk of gastrointestinal cancer in the subject.

In one embodiment, the method comprises determining in the biological sample of the subject, whether mutation is present in at least one of the CTCF-binding sites (CBS) overlapping regions set forth in the table below:

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or flanking sequences thereof.

In one embodiment, the method further comprises determining in the biological sample of the subject, whether mutation is present in at least one of the non-CBS regions set forth in the table below:

| Chromosome | Start site | End site |
|---|---|---|
| 7 | 68391104 | 68391132 |
| 7 | 136495924 | 136495948 |
| 2 | 57627616 | 57627640 |
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or flanking sequences thereof.

In one embodiment, the method further comprises determining in the biological sample of the subject, whether mutation is present in at least one of the genes selected from the group consisting of: KRAS, TP53, RHOA, ARID1A, PIK3CA, ERBB3 and PTEN, wherein presence of mutation in at least one of the CBS overlapping regions, or portions or flanking sequences thereof, at least one of the non-CBS regions, or portions or flanking sequences thereof, and/or at least one of the genes is indicative of a risk of gastrointestinal cancer in the subject.

In one embedment, determining whether mutation is present in the CBS overlapping regions, or portions or flanking sequences thereof, and/or the non-CBS regions, or portions or flanking sequences thereof, does not comprise determining whether mutation is present in a region spanning more than 50 nucleotides.

In one embodiment, determining whether mutation is present in at least one of the CBS overlapping regions, or portions or flanking sequences thereof, comprises contacting the biological sample with a primer having at least about 85% sequence identity to a sequence selected from the group consisting of: SEQ ID NO. 35, SEQ ID NO. 36, SEQ ID NO. 39, SEQ ID NO. 40, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 57, SEQ ID NO. 58, SEQ ID NO. 59, SEQ ID NO. 60, SEQ ID NO. 65, SEQ ID NO. 66, SEQ ID NO. 77, SEQ ID NO. 78, SEQ ID NO. SEQ ID NO. 83, SEQ ID NO. 84 and combinations thereof.

In one embodiment, determining whether mutation is present in at least one of the non-CBS regions, or portions or flanking sequences thereof, comprises contacting the biological sample with a primer having at least about 85% sequence identity to a sequence selected from the group consisting of: SEQ ID NO. 37, SEQ ID NO. 38, SEQ ID NO. 41, SEQ ID NO. 42, SEQ ID NO. 43, SEQ ID NO. 44, SEQ ID NO. 53, SEQ ID NO. 54, SEQ ID NO. 55, SEQ ID NO. 56, SEQ ID NO. 61, SEQ ID NO. 62, SEQ ID NO. 63, SEQ ID NO. 64, SEQ ID NO. 67, SEQ ID NO. 68, SEQ ID NO. 71, SEQ ID NO. 72, SEQ ID NO. 75, SEQ ID NO. 76, SEQ ID NO. 81, SEQ ID NO. 82, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, and combinations thereof.

In one embodiment, the method comprises determining whether mutation is present in at least two of the CBS overlapping regions, or portions or flanking sequences thereof, set forth in the table.

In one embodiment, the method comprises determining whether mutation is present in all of the CBS overlapping regions, or portions or flanking sequences thereof, set forth in the table.

In one embodiment, the method comprises determining whether mutation is present in all of the CBS overlapping regions, or portions or flanking sequences thereof, and all of the non-CBS regions, or portions or flanking sequences thereof, set forth in the tables.

In one embodiment, the method has a detection sensitivity of no less than about 50%.

In one aspect, there is provided a method of treating gastrointestinal cancer in a human subject, the method comprising: determining in a biological sample of the subject, whether mutation is present in at least one of the CTCF-binding sites (CBS) overlapping regions set forth in the table below:

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or flanking sequences thereof,
or one of the non-CBS regions set forth in the table below:

| Chromosome | Start site | End site |
|---|---|---|
| 7 | 68391104 | 68391132 |
| 7 | 136495924 | 136495948 |
| 2 | 57627616 | 57627640 |
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or flanking sequences thereof,
wherein if the biological sample shows a presence of mutation in at least one of the CBS overlapping regions, or portions or flanking sequences thereof, and/or at least one of the non-CBS regions, or portions or flanking sequences thereof, the subject is administered a therapeutic agent for treating gastrointestinal cancer.

In one embodiment, the method comprises determining in the biological sample of the subject, whether mutation is present in at least one of the CBS overlapping regions set forth in the table below:

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or flanking sequences thereof.

In one embodiment, the method further comprises determining in the biological sample of the subject, whether mutation is present in at least one of the non-CBS regions set forth in the table below:

| Chromosome | Start site | End site |
|---|---|---|
| 7 | 68391104 | 68391132 |
| 7 | 136495924 | 136495948 |
| 2 | 57627616 | 57627640 |
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or flanking sequences thereof.

In one embodiment, the method further comprises determining in the biological sample of the subject, whether mutation is present in at least one of the genes selected from the group consisting of: KRAS, TP53, RHOA, ARID1A, PIK3CA, ERBB3 and PTEN, wherein if the biological sample shows a presence of mutation in at least one of the CBS overlapping regions, or portions or flanking sequences thereof, at least one of the non-CBS regions, or portions or flanking sequences thereof, and/or at least one of the genes, the subject is administered a therapeutic agent for treating gastrointestinal cancer.

In one embodiment, the therapeutic agent is selected from the group consisting of chemotherapy, radiation therapy, immunotherapy and combinations thereof.

In one embodiment, the biological sample is a fluid biological sample.

In one embodiment, the fluid biological sample is selected from the group consisting of: blood, plasma, serum and combinations thereof.

In one embodiment, the gastrointestinal cancer is selected from the group consisting of gastric cancer, colorectal cancer, colon cancer and rectal cancer.

In one aspect, there is provided a kit for detecting gastrointestinal cancer in a human subject, the kit comprising: an agent for detecting mutation in at least one of the CBS overlapping regions set forth in the table below:

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or flanking sequences thereof,
or in at least one of the non-regions set forth in the table below:

| Chromosome | Start site | End site |
|---|---|---|
| 7 | 68391104 | 68391132 |
| 7 | 136495924 | 136495948 |
| 2 | 57627616 | 57627640 |
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or flanking sequences thereof.

In one embodiment, the kit comprises an agent for detecting mutation in at least one of the CBS overlapping regions set forth in the table below:

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or flanking sequences thereof.

In one embodiment, the kit further comprises an agent for detecting mutation in at least one of the non-CBS regions set forth in the table below:

| Chromosome | Start site | End site |
|---|---|---|
| 7 | 68391104 | 68391132 |
| 7 | 136495924 | 136495948 |
| 2 | 57627616 | 57627640 |

-continued

| Chromosome | Start site | End site |
|---|---|---|
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or flanking sequences thereof.

In one embodiment, the kit further comprises an agent for detecting mutation in at least one of the genes selected from the group consisting of: KRAS, TP53, RHOA, ARID1A, PIK3CA, ERBB3, PTEN.

In one embodiment, the agent for detecting mutation in at least one of the CBS overlapping regions, or portions or flanking sequences thereof, comprises a primer having at least about 85% sequence identity to a sequence selected from the group consisting of: SEQ ID NO. 35, SEQ ID NO. 36, SEQ ID NO. 39, SEQ ID NO. 40, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 57, SEQ ID NO. 58, SEQ ID NO. 59, SEQ ID NO. 60, SEQ ID NO. 65, SEQ ID NO. 66, SEQ ID NO. 77, SEQ ID NO. 78, SEQ ID NO. SEQ ID NO. 83 and SEQ ID NO. 84.

In one embodiment, the agent for detecting mutation in at least one of the non-CBS regions, or portions or flanking sequences thereof, comprises a primer having at least about 85% sequence identity to a sequence selected from the group consisting of: SEQ ID NO. 37, SEQ ID NO. 38, SEQ ID NO. 41, SEQ ID NO. 42, SEQ ID NO. 43, SEQ ID NO. 44, SEQ ID NO. 53, SEQ ID NO. 54, SEQ ID NO. 55, SEQ ID NO. 56, SEQ ID NO. 61, SEQ ID NO. 62, SEQ ID NO. 63, SEQ ID NO. 64, SEQ ID NO. 67, SEQ ID NO. 68, SEQ ID NO. 71, SEQ ID NO. 72, SEQ ID NO. 75, SEQ ID NO. 76, SEQ ID NO. 81, SEQ ID NO. 82, SEQ ID NO. 85, SEQ ID NO. 86, SEQ ID NO. 87, SEQ ID NO. 88, SEQ ID NO. 89, SEQ ID NO. 90, SEQ ID NO. 91 and SEQ ID NO. 92.

In one embodiment, the kit comprises agents for detecting mutation in at least two of the CBS overlapping regions, or portions or flanking sequences thereof, set forth in the table.

In one embodiment, the kit comprises agents for detecting mutation in all of the CBS overlapping regions, or portions or flanking sequences thereof, set forth in the table.

In one embodiment, the kit comprises agents for detecting mutation in all of the CBS overlapping regions, or portions or flanking sequences thereof, and all of the non-CBS regions, or portions or flanking sequences thereof, set forth in the tables.

In one embodiment, the human subject is an Asian subject.

Definitions

The term "biological sample" refers to a sample obtained from a biological subject, including a sample of biological tissue or fluid origin obtained in vivo or in vitro. Hence, a "biological sample" may be a solid biological sample or a liquid biological sample. Examples of a "solid biological sample" include tumor biopsy and examples of a "fluid biological sample" or "liquid biological sample" include blood, serum, plasma, sputum, lavage fluid (for example peritoneal lavage), cerebrospinal fluid, urine, semen, sweat, tears, saliva, and the like. As used herein, the terms "blood," "plasma" and "serum" encompass fractions or processed portions thereof. Similarly, where a sample is taken from a biopsy, swab, smear, etc., the "sample" encompasses a processed fraction or portion derived from the biopsy, swab, smear, etc.

The term "mutation", when used in relation to a nucleic acid sequence, is to be interpreted broadly to refer to an alteration in a nucleic acid sequence as compared to a reference sequence (typically a wild-type sequence). A wild-type sequence generally refers to a sequence found in a normal cell rather than in an abnormal or cancer cell (for example, a gastrointestinal cancer cell). Examples of a wild-type sequence include SEQ ID NOs. 1-34. The term "mutation" includes deletions, additions, insertions and/or substitutions. A "mutation" may be inherited, naturally occurring, or introduced. The term "mutation", when used in relation to a coding gene, generally refers (but is not limited) to a sequence variant that encodes for a protein that is distinct (e.g. in terms of function, conformation, structure etc.) from a protein that is encoded by a wild-type gene.

The term "gene" as used in herein primarily relates to a coding sequence, but can also include some or all of the surrounding regulatory elements or introns. Accordingly, a "mutation", when used in relation to a coding gene, may also include a deletion, addition, insertion and/or substitution in a regulatory element or intron of the coding gene. The term "gene" also includes artificial or recombinant genes created from cDNA or genomic DNA, including recombinant genes based upon splice variants.

All genomic coordinates delineating chromosomal regions used herein are specified according to human reference genome build GRCh37. A "start site" when used herein in relation to a chromosomal region generally relates to the location of the first sequence defining a beginning the chromosomal region and an "end site" generally relates to the position of a last sequence defining an end point of the chromosomal region. For example, a CBS overlapping region with the genomic coordinates "chromosome 6, start site: 50570094, end site: 50570120" spans the region from position 50570094 (inclusive) to position 50570120 (inclusive) on chromosome 6 according to human reference genome build GRCh37. A mutation in the above CBS overlapping region therefore encompasses a mutation occurring anywhere within the region from position 50570094 (inclusive) to position 50570120 (inclusive) on chromosome 6 according to human reference genome build GRCh37.

The term "overlapping region", when used herein in relation to a nucleic acid sequence, is to be interpreted broadly to include a nucleic acid region containing at least a part of or the whole of the nucleic acid sequence. For example, the term "CTCF-binding site (CBS) overlapping region" includes a nucleic acid region containing at least a part of or the whole of a CBS. A "CBS overlapping region" may thus include sequences that are not part of a CBS, as long as at least one nucleotide in the region is a component nucleotide of (i.e. a part of) a CBS.

The term "flanking sequence(s)", when used in relation to a nucleic acid sequence, is to be interpreted broadly to refer to any sequence(s)/base pair(s)/nucleotide(s) immediately contiguous to the nucleic acid sequence at its 5' end and 3' end. The length of a "flanking sequence(s)" is typically about 1-10 nucleotides/base pairs, such as 2, 3, 4, 5, 6, 7, 8, 9 or 10 nucleotides/base pairs. Hence, the term "flanking sequence(s)", when used in relation to a CBS overlapping region, refers to the continuous sequences of no more than 10 nucleotides/base pairs immediately contiguous to the 5' end of the CBS overlapping region and the 3' end of the CBS overlapping region. For example, the "flanking sequence(s)" of the CBS overlapping region "chromosome 6, start site: 50570094, end site: 50570120" encompasses nucleotide(s)/base pair(s) at the positions 50570084 (inclusive) to 50570093 (inclusive) and the nucleotide(s)/base pair(s) at positions 50570121 (inclusive) to 50570130 (inclusive).

The term "isolated" as used herein refers to a nucleic acid or polynucleotide that is removed from its natural environment. An "isolated" nucleic acid or polynucleotide is typically partially purified. The term includes, for example, a recombinant nucleic acid which is incorporated into a vector, into an autonomously replicating plasmid or virus, or into the genomic DNA of a prokaryote or eukaryote, or which exists as a separate molecule independent from any other sequences.

The expression "determining a risk of cancer" when used herein broadly includes determining/detecting a presence of cancer (including recurrent and/or metastatic cancer). Accordingly, the expression "determining a risk of gastrointestinal cancer" includes determining/detecting a presence of gastrointestinal cancer (including recurrent and/or metastatic gastrointestinal cancer).

As used herein, the term "therapeutically effective amount" of a compound will be an amount of an active agent that is capable of preventing or at least slowing down (lessening) a medical condition, such as autoimmune diseases, inflammation and cancer. Dosages and administration of compounds, compositions and formulations of the present disclosure may be determined by one of ordinary skill in the art of clinical pharmacology or pharmacokinetics. See, for example, Mordenti and Rescigno, (1992) Pharmaceutical Research. 9:17-25; Morenti et al., (1991) Pharmaceutical Research. 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the active agent of the present disclosure to be employed therapeutically will depend, for example, upon the therapeutic objectives, the route of administration, and the condition of the patient. Accordingly, it may be necessary for the therapist to titer the dosage and modify the route of administration as required to obtain the optimal therapeutic effect.

The term "Asian" includes a human classification of persons who descend from an ethnic group in Asia. For example, a person having origins in any of the original peoples of the Far East, Southeast Asia, or the Indian subcontinent, including, for example, China (including Hong Kong), Singapore, Malaysia and India.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

DESCRIPTION OF EMBODIMENTS

Exemplary, non-limiting embodiments of the disclosure are disclosed hereinafter. Unless defined otherwise, all technical and scientific terms used herein have the same meanings as commonly understood by one or ordinary skill in the art to which the present disclosure belongs.

In various embodiments, there is provided a method of obtaining/predicting a clinical picture of a test subject, the method comprising determining in a biological sample of the test subject, a biological data associated with one or more non-coding polynucleotide sequences/regions.

In various embodiments, the clinical picture comprises at least one of: a presence/likelihood/propensity/risk of a proliferative disease in a test subject, a presence/likelihood/propensity/risk of recurrence/relapse of a proliferative disease in a test subject, a presence/likelihood/propensity/risk of metastasis of a proliferative disease in a test subject, an indication of the life expectancy/survival rate/time to death of a test subject having a proliferative disease or an efficacy of a treatment regimen for a test subject having a proliferative disease.

In various embodiments, the proliferative disease is cancer. The cancer may be metastatic and/or recurrent. In various embodiments, the cancer may include but is not limited to liver cancer, liver hepatocellular cancer, pancreatic cancer, pancreas adenocarcinoma, lung cancer, lung adenocarcinoma, lung squamous cell carcinoma, lymphoma, breast cancer and gastrointestinal cancer. The cancer may be adenocarcinoma, sarcoma, carcinoid tumors, gastrointestinal stromal tumor (GIST) and/or lymphoma. In some embodiments, the cancer comprises gastrointestinal cancer. In some embodiments, the gastrointestinal cancer may include but is not limited to stomach/gastric cancer, colorectal cancer, colon cancer and rectal cancer. The gastric cancer may be intestinal type, diffuse type and/or mixed type. In some embodiments, the cancer does not include gastric adenocarcinoma subtype of tumors with high levels of microsatellite instability (MSI).

In various embodiments, the test subject is a human subject. In some embodiments, the human subject is an Asian subject. In some embodiments, the Asian subject is a Chinese subject.

In various embodiments, the biological data comprises a mutation. In various embodiments, the biological data comprises from 1 to 50 mutations. In various embodiments, the biological data comprises at least one mutation, at least two mutations, at least three mutations, at least four mutations, at least five mutations, at least six mutations, at least seven mutations, at least eight mutations, at least nine mutations, at least ten mutations, at least 11 mutations, at least 12 mutations, at least 13 mutations, at least 14 mutations, at least 15 mutations, at least 16 mutations, at least 17 mutations, at least 18 mutations, at least 19 mutations, at least 20 mutations, at least 21 mutations, at least 22 mutations, at least 23 mutations, at least 24 mutations, at least 25 mutations, at least 26 mutations, at least 27 mutations, at least 28 mutations, at least 29 mutations, at least 30 mutations, at least 31 mutations, at least 32 mutations, at least 33 mutations or at least 34 mutations.

In some embodiments, the one or more non-coding polynucleotide sequences/regions comprises a non-coding sequence/region of a gene or within a gene. The non-coding sequence/region of a gene or within a gene may comprise an intron of the gene. The non-coding sequence/region of a gene or within a gene may comprise a sequence/region that is not an exon of the gene. In some embodiments, the one or more non-coding polynucleotide sequences/regions comprises an intergenic sequence/region.

In some embodiments, the one or more non-coding polynucleotide sequences/regions comprises a sequence/region that is enriched/located in conserved sequences.

In some embodiments, each of the one or more non-coding polynucleotide sequences/regions is not in proximity with TERT gene. In some embodiments, at least one gene, at least two genes, at least three genes, at least four genes or at least five genes is present in the region spanning the TERT gene and each of the one or more non-coding polynucleotide sequences/regions that is not in proximity with TERT gene. In some embodiments, each of the one or more non-coding polynucleotide sequences/regions that is not in proximity with TERT gene is located at least about 180 kilobase pairs (kbp), at least about 177 kbp, at least about 170 kbp, at least about 160 kbp, at least about 150 kbp, at least about 140 kbp, at least about 130 kbp, at least about 120 kbp, at least about 110 kbp, at least about 100 kbp, at least about 90 kbp, at least about 80 kbp, at least about 70 kbp, at least about 60 kbp, at least about 50 kbp, at least about 40 kbp, at least about 30 kbp, at least about 20 kbp or at least about 10 kbp from the TERT gene.

In various embodiments, the one or more non-coding polynucleotide sequences/regions is located on a human chromosome selected from the group consisting of: human chromosome 1, human chromosome 2, human chromosome 3, human chromosome 4, human chromosome 5, human chromosome 6, human chromosome 7, human chromosome 8, human chromosome 9, human chromosome 12, human chromosome 13, human chromosome 14, human chromosome 16, human chromosome X and any combinations thereof. In various embodiments, the one or more non-coding polynucleotide sequences/regions is not located on a human chromosome selected from the group consisting of: human chromosome 10, human chromosome 11, human chromosome 15, human chromosome 17, human chromosome 18, human chromosome 19, human chromosome 20, human chromosome 21, human chromosome 22, human chromosome Y and any combinations thereof.

In some embodiments, the one or more non-coding polynucleotide sequences/regions comprises a polynucleotide sequence/region indicated in Table 1 below:

TABLE 1

| Chromosome | Start site | End site | Cytogenic location |
|---|---|---|---|
| 6 | 50570094 | 50570120 | 6p12.3 |
| 7 | 68391104 | 68391132 | 7q11.22 |
| 8 | 71000992 | 71001012 | 8q13.3 |
| 7 | 136495924 | 136495948 | 7q33 |
| 2 | 57627616 | 57627640 | 2p16.1 |
| 1 | 209422184 | 209422222 | 1q32.2 |
| 2 | 49173770 | 49173816 | 2p16.3 |
| 2 | 239033350 | 239033370 | 2q37.3 |
| 4 | 182064578 | 182064613 | 4q34.3 |
| X | 104435106 | 104435140 | Xq22.3 |
| 16 | 8381278 | 8381302 | 16p13.2 |
| 5 | 23824204 | 23824224 | 5p14.2 |
| 7 | 67614923 | 67614943 | 7q11.22 |
| 14 | 70285576 | 70285601 | 14q24.2 |
| 6 | 73122084 | 73122123 | 6q13 |
| 8 | 65161396 | 65161420 | 8q12.3 |
| 7 | 4937707 | 4937736 | 7p22.1 |
| 8 | 70576141 | 70576184 | 8q13.3 |
| 12 | 126996666 | 126996686 | 12q24.32 |
| 1 | 153607104 | 153607124 | 1q21.3 |
| 4 | 5415060 | 5415082 | 4p16.2 |
| 16 | 13516145 | 13516165 | 16p13.12 |
| X | 137405623 | 137405655 | Xq26.3 |
| 13 | 36552821 | 36552860 | 13q13.3 |
| 4 | 62653076 | 62653096 | 4q13.1 |
| 3 | 171164993 | 171165017 | 3q26.31 |
| 4 | 144748744 | 144748764 | 4q31.21 |
| 3 | 164903700 | 164903728 | 3q26.1 |
| 5 | 1472143 | 1472163 | 5p15.33 |
| 9 | 25481736 | 25481758 | 9p21.3 |
| 2 | 77150455 | 77150477 | 2p12 |

TABLE 1-continued

| Chromosome | Start site | End site | Cytogenic location |
|---|---|---|---|
| 3 | 104801455 | 104801477 | 3q13.11 |
| X | 125548690 | 125548710 | Xq25 |
| 14 | 83046706 | 83046744 | 14q31.1 |

In some embodiments therefore, there is provided a method of determining a risk of/predicting the likelihood of/detecting cancer in a test subject, the method comprising: determining in a biological sample of the subject, whether mutation is present in at least one of the regions, or portions or flanking sequences thereof, set forth in the Table 1.

In various embodiments, the one or more non-coding polynucleotide sequences/regions comprises a sequence set forth in SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33 or SEQ ID NO. 34.

In various embodiments, the one or more non-coding polynucleotide sequences/regions comprises a transcription factor binding site (TFBS) or portions thereof. In some embodiments, the one or more non-coding polynucleotide sequences/regions comprises a CTCF (11-zinc finger protein or CCCTC-binding factor) binding site (CBS) or a CTCF binding motif and a flanking sequence/region/boundary thereof, optionally wherein the flanking sequence/region/boundary is no more than about 10 bp, no more than about 9 bp, no more than about 8 bp, no more than about 7 bp, no more than about 6 bp, no more than about 5 bp, no more than about 4 bp, no more than about 3 bp, no more than about 2 bp or no more than about 1 bp in length. In some embodiments, the CTCF binding motif has the following position frequency matrix (JASPAR ID: MA0139.1 and UniProt ID: P49711):

```
A [ 87 167 281 56 8 744 40 107 851 5 333 54 12 56 104 372 82 117 402 ]
C [ 291 145 49 800 903 13 528 433 11 0 3 12 0 8 733 13 482 322 181 ]
G [ 76 414 449 21 0 65 334 48 32 903 566 504 890 775 5 507 307 73 266 ]
T [ 459 187 134 36 2 91 11 324 18 3 9 341 8 71 67 17 37 396 59 ]
```

CTCF is a DNA-binding protein essential for the maintenance of genome architecture by mediating both short and long-range chromosomal contacts. Together with the cohesin complex, CTCF organizes chromatin into large topologically associating domains (TADs), insulating the local chromosomal neighborhoods from adjacent regions. Disruption of CTCF binding can therefore lead to dysregulation of gene expression. In cancer, CTCF binding is found to be disrupted through various mechanisms such as DNA copy number alterations spanning domain boundaries, microdeletions within CBSs, and hypermethylation of CBSs. These alterations at CBSs may drive cancer progression by allowing ectopic expression of oncogenes. Notably, a genome-wide elevated somatic mutation rate across CBSs in several cancer types was found. This suggests that mutational and DNA repair processes may act differently at CBSs relative to other genomic regions, thereby resulting in an overall elevated mutational burden at such sites in cancer. More notably, the inventors have also identified 11 CBS overlapping regions that are surprisingly significantly mutated even after controlling for genome-wide elevated mutation rate at CBSs.

In some embodiments therefore, the mutation comprises a mutation at a CBS or CTCF binding motif or a flanking sequence/region/boundary thereof.

Further, in some embodiments, the mutation within the one or more non-coding polynucleotide sequences/regions comprises a mutation that cannot be fully accounted by genome-wide elevated mutation rate of the one or more non-coding polynucleotide sequence/region. In some embodiments wherein the mutation is located within a CBS, the mutation comprises a mutation that cannot be fully accounted by genome-wide elevated mutation rate at CBS (for example, the mutation is one that remains significant after adjustment with a CBS-specific background mutation model).

Accordingly, in some embodiments, there is provided a method of determining a risk of/predicting the likelihood of/detecting gastrointestinal cancer in a human subject, the method comprising: determining in a biological sample of the subject, whether mutation is present in a CTCF-binding sites (CBS) overlapping region, optionally wherein the CBS overlapping region is set forth in Table 2 below:

TABLE 2

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or flanking sequences thereof, wherein presence of mutation in at least a CBS overlapping region, or portions or flanking sequences thereof, indicates a risk of gastrointestinal cancer (for example, an increased or elevated risk of gastrointestinal cancer) or the likelihood that the subject has gastrointestinal cancer or is predisposed to gastrointestinal cancer or that the subject has gastrointestinal cancer or is predisposed to gastrointestinal cancer.

In some embodiments, there is provided a method of determining a risk of gastrointestinal cancer in a human subject, the method comprising: determining in a biological sample of the subject, whether mutation is present in at least one of the CBS overlapping regions set forth in Table 2, or portions or flanking sequences thereof, wherein presence of mutation in at least one of the CBS overlapping regions, or portions or flanking sequences thereof, is indicative of a risk of gastrointestinal cancer in the subject.

In some embodiments, the TFBS or CBS overlapping regions comprises a sequence set forth in SEQ ID NO. 1, SEQ ID NO. 3, SEQ ID NO. 6, SEQ ID NO. 7, SEQ ID NO. 9, SEQ ID NO. 10, SEQ ID NO. 14, SEQ ID NO. 15, SEQ ID NO. 18, SEQ ID NO. 24 and SEQ ID NO. 28.

In some embodiments, the one or more non-coding polynucleotide sequences/regions comprises a sequence/region that is not a TFBS (or a CBS) or portions thereof.

Accordingly, in some embodiments, there is provided a method of determining a risk of/predicting the likelihood of/detecting gastrointestinal cancer in a human subject, the method comprising: determining in a biological sample of the subject, whether mutation is present in a non-CBS region, optionally wherein the non-CBS region is set forth in Table 3 below:

TABLE 3

| Chromosome | Start site | End site |
|---|---|---|
| 7 | 68391104 | 68391132 |
| 7 | 136495924 | 136495948 |
| 2 | 57627616 | 57627640 |
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or flanking sequences thereof, wherein presence of mutation in at least a non-CBS region, or portions or flanking sequences thereof, indicates a risk of gastrointestinal cancer or the likelihood that the subject has gastrointestinal cancer or is predisposed to gastrointestinal cancer or that the subject has gastrointestinal cancer or is predisposed to gastrointestinal cancer.

In some embodiments therefore, the method further comprises determining in a biological sample of the subject, whether mutation is present in at least one of the non-CBS regions set forth in Table 3, or portions or flanking sequences thereof, wherein presence of mutation in at least one of the CBS overlapping regions, or portions or flanking sequences thereof, and/or at least one of the non-CBS regions, or portions or flanking sequences thereof, is indicative of a risk of gastrointestinal cancer in the subject.

In some embodiments, there is provided a method of determining a risk of gastrointestinal cancer in a human subject, the method comprising: determining in a biological sample of the subject, whether mutation is present in at least one of the CTCF-binding sites (CBS) overlapping regions set forth in Table 2, or portions or flanking sequences thereof, or at least one of the non-CBS regions set forth in Table 3, or portions or flanking sequences thereof, wherein presence of mutation in at least one of the CBS overlapping regions, or portions or flanking sequences thereof, and/or at least one of the non-CBS regions, or portions or flanking sequences thereof, is indicative of a risk of gastrointestinal cancer in the subject.

In some embodiments, determining whether mutation is present in each of the one or more non-coding polynucleotide sequences/regions comprises determining whether at least one mutation, at least two mutations, at least three mutations, at least four mutations, at least five mutations, at least six mutations, at least seven mutations, at least eight mutations, at least nine mutations or at least ten mutations is/are present in each of the one or more non-coding polynucleotide sequences/regions. For example, determining whether mutation is present in a non-coding polynucleotide sequences/regions selected from the group consisting of chr 4: 144748744-144748764, chr 7: 136495924-136495948, chr 8: 70576141-70576184, chr 2: 77150455-77150477 and chr 7: 68391104-68391132 comprises determining whether at least three mutations, at least four mutations, at least five mutations or at least six mutations are present in the non-coding polynucleotide sequences/regions. In various embodiments, each of the one or more non-coding polynucleotide sequences/regions is no more than about 50 bp, no more than about 49 bp, no more than about 48 bp, no more than about 47 bp, no more than about 46 bp, no more than about 45 bp, no more than about 44 bp, no more than about 43 bp, no more than about 42 bp, no more than about 41 bp, no more than about 40 bp, no more than about 39 bp, no more than about 38 bp, no more than about 37 bp, no more than about 36 bp, no more than about 35 bp, no more than about 34 bp, no more than about 33 bp, no more than about 32 bp, no more than about 31 bp, no more than about 30 bp, no more than about 29 bp, no more than about 28 bp, no more than about 27 bp, no more than about 26 bp, no more than about 25 bp, no more than about 24 bp, no more than about 23 bp, no more than about 22 bp, no more than about 21 bp, no more than about 20 bp, no more than about 19 bp, no more than about 18 bp, no more than about 17 bp, no more than about 16 bp or no more than about 15 bp in length. Advantageously, mutations in the one or more non-coding polynucleotide sequences/regions are concentrated and focal, and hence the one or more non-coding polynucleotide sequences/regions are extremely well suited as biomarkers in liquid biopsy assays.

In various embodiments therefore, determining whether mutation is present in the CBS overlapping regions, or portions or flanking sequences thereof, and/or the non-CBS regions, or portions or flanking sequences thereof, does not comprise determining whether mutation is present in a region spanning more than 50 nucleotides. In various embodiments, determining whether mutation is present in the CBS overlapping regions, or portions or flanking sequences thereof, and/or the non-CBS regions, or portions or flanking sequences thereof, comprises determining whether mutation is present in a region spanning no more than 50 nucleotides.

In various embodiments, the mutation may comprise a point mutation. The mutation may also comprise one of the following selected from the group consisting of: an insertion mutation, a deletion mutation, a substitution mutation, insertion/deletion mutation (indels), or any combinations thereof. The mutation may also comprise a missense mutation, a splice site mutation, a frame-shift mutation, a nonsense mutation or the like. In some embodiments, the mutation comprises a mutation selected from the group consisting of: A.T>C.G substitution, A.T>G.C substitution, T>G substitution, T>C substitution, T>A substitution and any combinations thereof.

In various embodiments, the mutation comprises a mutation at a position selected from the group consisting of: position 1, position 2, position 3, position 8, position 9, position 10, position 11, position 12, position 17, position 18, position 19 and any combination thereof of a CBS or CTCF binding motif but is not limited as such. In various embodiments, the mutation does not comprise a mutation at a position selected from the group consisting of: position 4, position 5, position 6, position 7, position 13, position 14, position 15, position 16 and any combination thereof of a CBS or CTCF binding motif but is not limited as such.

In some embodiments, wherein the mutation is located in one or more non-CBS region, a plurality of said non-CBS regions, taken collectively, is not enriched in a mutation selected from the group consisting of: A.T>C.G substitution, A.T>G.C substitution and any combinations thereof.

In some embodiments, the mutation comprises a mutation at a sequence/region/boundary flanking a CBS. The sequence/region/boundary flanking a CBS may comprise a sequence/region/boundary flanking the 5' end of the CBS or alternatively/additionally the 3' end of the CBS. The sequence/region/boundary flanking a CBS may be about 1-10 nucleotides/base pairs, such as 2, 3, 4, 5, 6, 7, 8, 9 or 10 nucleotides/base pairs.

Advantageously, sensitivity of the method may be increased by combining mutations in the non-coding polynucleotide sequences/regions with frequently (and focally) mutated protein coding regions in gastrointestinal cancer. Sensitivity of the method may also be increased by combining two or more mutations in the non-coding polynucleotide sequences/regions.

In various embodiments therefore, the method further comprises determining in a biological sample of the test subject, a biological data associated with a gene sequence/region or fragment thereof. In some embodiments, wherein the biological data comprises a presence of a mutation within the gene sequence/region or fragment thereof.

In various embodiments, the method further comprises determining from the biological sample, a mutation in or associated with at least 1, at least 2, at least 3, at least 4, at least 5, at least 6, at least 7, at least 8 of the genes selected from KRAS, TP53, RHOA, ARID1A, PIK3CA, ERBB3, PTEN and HLA-B. In some embodiments, the method further comprises determining from the biological sample, whether mutation is also present in at least one of regions coding for proteins selected from KRAS, TP53, RHOA, ARID1A, PIK3CA, ERBB3, PTEN and HLA-B. In some embodiments, the method further comprises determining in the biological sample of the subject, whether mutation is present in at least one of the genes selected from the group consisting of: KRAS, TP53, RHOA, ARID1A, PIK3CA, ERBB3 and PTEN, wherein presence of mutation in at least one of the CBS overlapping regions, or portions or flanking sequences thereof, at least one of the non-CBS regions, or portions or flanking sequences thereof, and/or at least one of the genes is indicative of a risk of gastrointestinal cancer in the subject. In some embodiments, the method further comprises determining in the biological sample of the subject, whether mutation is present in at least one of the genes selected from the group consisting of: KRAS, TP53 and RHOA, wherein presence of mutation in at least one of the CBS overlapping regions, or portions or flanking sequences thereof, at least one of the non-CBS regions, or portions or flanking sequences thereof, and/or at least one of the genes is indicative of a risk of gastrointestinal cancer in the subject.

In various embodiments, the method comprises determining in a biological sample of the subject, a mutation in or associated with at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33 or at least 34 of the non-coding polynucleotide sequence/region in Table 1.

In various embodiments, the method comprises determining from a biological sample obtained from the subject, whether mutation is present in at least 1, at least 2, at least 3, at least 4, at least 5, at least 6, at least 7, at least 8, at least 9, at least 10 or all 11 of the non-coding regions shown in Table 2 that overlaps/are TF binding sites or CBS and/or determining from the biological sample, whether mutation is also present in at least 1, at least 2, at least 3, at least 4, at least 5, at least 6, at least 7, at least 8, at least 9, at least 10, at least 11, at least 12, at least 13, at least 14, at least 15, at least 16, at least 17 or all 18 of the non-coding regions shown in Table 3 that do not overlap with said TF binding sites or CBS.

In some embodiments, the method comprises determining whether mutation is present in at least two of the CBS overlapping regions, or portions or flanking sequences thereof, set forth in Table 2. In some embodiments, the method comprises determining whether mutation is present in all of the CBS overlapping regions, or portions or flanking sequences thereof, set forth in Table 2. In some embodiments, the method comprises determining whether mutation is present in all of the CBS overlapping regions, or portions or flanking sequences thereof, and all of the non-CBS regions, or portions or flanking sequences thereof, set forth in Tables 2 and 3.

In various embodiments, the method has a detection sensitivity/accuracy of no less than about 15%, of no less than about 20%, no less than about 25%, no less than about 30%, no less than about 40%, no less than about 45%, no less than about 50%, no less than about 55%, no less than about 60%, no less than about 65%, no less than about 70%, no less than about 75%, no less than about 85%, no less than about 90%, or no less than about 95%. In some embodiments, the method has a detection sensitivity of no less than about 50%.

In various embodiments, the method is at least one of a diagnosis method, a prognosis method, a method of disease monitoring, a method of detecting recurrence or a method of detecting metastasis. In some embodiments, the method comprises an early detection method or a monitoring method of disease relapse/recurrence and/or metastasis.

In various embodiments, the method is an in vitro method. In various embodiments, the method is an ex vivo method.

In various embodiments, the method further comprises obtaining the biological sample from the test subject prior to the determining step. In some embodiments, the step of obtaining the biological sample from the test subject is a non-surgical step, a non-invasive step or a minimally invasive step. In some embodiments, the step of obtaining the biological sample from the test subject comprises withdrawing a blood sample from the test subject or obtaining a tumor biopsy from the test subject. In some embodiments, the method further comprises the step of removing particulate blood components from the blood sample to leave behind blood plasma for use in the determining step. In some embodiments, the particulate blood components are selected from the group consisting red blood cells, white blood cells, platelets and combinations thereof.

In various embodiments, the biological sample is a solid biological sample. In some embodiments, the solid biological sample comprises a solid sample derived from a tumor tissue, such as a solid bulk tumor. The solid sample derived from a tumor tissue may comprise a tumor biopsy. In various embodiments, the biological sample is a fluid biological sample. In some embodiments, the fluid biological may include but is not limited to blood, plasma, serum and combinations thereof, and the like.

In various embodiments, the biological sample comprises cell free DNA or circulating DNA of a tumor cell. In various embodiments, the cell free DNA or circulating DNA of a tumor cell is no more than about 250 bp, no more than about 240 bp, no more than about 230 bp, no more than about 220 bp, no more than about 210 bp, no more than about 200 bp, no more than about 190 bp, no more than about 180 bp, no more than about 170 bp, no more than about 160 bp, no more than about 150 bp, no more than about 140 bp, no more than about 130 bp, no more than about 120 bp, no more than about 110 bp, no more than about 100 bp in length, no more than about 90 bp, no more than about 80 bp, no more than about 70 bp, no more than about 60 bp or no more than about 50 bp in length but is not limited as such.

In various embodiments, the method requires no more than about 20 millilitres, no more than about 19.5 millilitres, no more than about 19 millilitres, no more than about 18.5 millilitres, no more than about 18 millilitres, no more than about 17.5 millilitres, no more than about 17 millilitres, no more than about 16.5 millilitres, no more than about 16 millilitres, no more than about 15.5 millilitres, no more than about 15 millilitres, no more than about 14.5 millilitres, no more than about 14 millilitres, no more than about 13.5 millilitres, no more than about 13 millilitres, no more than about 12.5 millilitres, no more than about 12 millilitres, no more than about 11.5 millilitres, no more than about 11 millilitres, no more than about 10.5 millilitres, no more than about 10 millilitres, no more than about 9.5 millilitres, no more than about 9 millilitres, no more than about 8.5 millilitres, no more than about 8 millilitres, no more than about 7.5 millilitres, no more than about 7 millilitres, no more than about 6.5 millilitres, no more than about 6 millilitres, no more than about 5.5 millilitres, no more than about 5 millilitres, no more than about 4.5 millilitres, no more than about 4 millilitres, no more than about 3.5 millilitres, no more than about 3 millilitres, no more than about 2.5 millilitres, no more than about 2 millilitres, no more than about 1.5 millilitres, no more than about 1 millilitres, no more than about 0.9 millilitres, no more than about 0.8 millilitres, no more than about 0.7 millilitres, no more than about 0.6 millilitres, no more than about 500 microliters of biological sample, no more than about 450 microliters of biological sample, no more than about 400 microliters of biological sample, no more than about 350 microliters of biological sample or no more than about 300 microliters of biological sample.

In various embodiments, there is provided a method of treating a proliferative disease in a subject in need thereof comprising: providing a biological sample from the subject; determining in the biological sample of the test subject, a presence of a mutation associated with one or more non-coding polynucleotide sequences/regions, wherein if the sample shows a presence of a mutation, the subject is subjected to treatment with an agent for treating the proliferative disease, optionally wherein the agent may include but is not limited to chemotherapy, radiation therapy, combination therapy, alternative therapy/complementary therapy and immunotherapy. In some embodiments, there is provided a method of treating gastrointestinal cancer in a human subject, the method comprising determining in a biological sample of the subject, whether mutation is present in at least one of the CTCF-binding sites (CBS) overlapping regions set forth in Table 2, or portions or flanking sequences thereof, or one of the non-CBS regions set forth in Table 3 or portions or flanking sequences thereof, wherein if the biological sample shows a presence of mutation in at least one of the CBS overlapping regions, or portions or flanking sequences thereof, and/or at least one of the non-CBS regions, or portions or flanking sequences thereof, the subject is administered a therapeutic agent for treating gastrointestinal cancer.

In some embodiments therefore, there is provided a method of treating gastrointestinal cancer in a human subject, the method comprising: determining in a biological sample of the subject, whether mutation is present in at least one of the CBS overlapping regions set forth in Table 2, or portions or flanking sequences thereof, wherein if the biological sample shows a presence of mutation in at least one of the CBS overlapping regions, or portions or flanking sequences thereof, the subject is administered a therapeutic agent for treating gastrointestinal cancer. In some embodiments, the method further comprises determining in the biological sample of the subject, whether mutation is present in at least one of the non-CBS regions set forth in Table 3, or portions or flanking sequences thereof, wherein if the biological sample shows a presence of mutation in at least one of the CBS overlapping regions, or portions or flanking sequences thereof, and/or at least one of the non-CBS regions, or portions or flanking sequences thereof, the subject is administered a therapeutic agent for treating gastrointestinal cancer. In some embodiments, the method further comprises determining in the biological sample of the subject, whether mutation is present in at least one of the genes selected from the group consisting of: KRAS, TP53, RHOA, ARID1A, PIK3CA, ERBB3 and PTEN, wherein if the biological sample shows a presence of mutation in at least one of the CBS overlapping regions, or portions or flanking sequences thereof, at least one of the non-CBS regions, or portions or flanking sequences thereof, and/or at least one of the genes, the subject is administered a therapeutic agent for treating gastrointestinal cancer. In some embodiments, the method further comprises determining in the biological sample of the subject, whether mutation is present in at least one of the genes selected from the group consisting of: KRAS, TP53 and RHOA, wherein if the biological sample shows a presence of mutation in at least one of the CBS overlapping regions, or portions or flanking sequences thereof, at least one of the non-CBS regions, or portions or flanking sequences thereof, and/or at least one of the genes, the subject is administered a therapeutic agent for treating gastrointestinal cancer.

In some embodiments, the therapeutic agent may include but is not limited to chemotherapy, radiation therapy, immunotherapy and combinations thereof. In some embodiments, a therapeutically effective amount of the therapeutic agent is administered to the subject.

In various embodiments, the method comprises a liquid biopsy assay. In various embodiments therefore, the method may include various existing experimental steps/approaches for targeted sequencing of the one or more non-coding polynucleotide sequences/regions in liquid biopsies (for example, Amplicon sequencing, capture probes and the like).

Detection of a presence of a mutation may be carried out according to any one of the many methods available to the man skilled in the art. In various embodiments, the determining step is carried out by performing an assay capable of detecting a presence of a mutation within the one or more non-coding polynucleotide sequences/regions. In some embodiments, the assay may include but is not limited to DNA sequencing methods, next-generation sequencing (NGS) methods, whole genome sequencing (WGS) methods, whole exome sequencing (WES) methods, panel sequencing methods, paired-end sequencing methods, DNA microarray methods, multiplex ligation-dependent probe amplification (MLPA) methods, single strand conformational polymorphism (SSCP) methods, denaturing gradient gel electrophoresis (DGGE) methods, heteroduplex analysis methods, restriction fragment length polymorphism (RFLP) methods, polymerase chain reaction (PCR) methods, molecular inversion probes, digital droplet PCR, fluorescent-probe PCR, quantitative PCR, allele-specific PCR or the like.

In various embodiments, determining whether mutation is present in one or more non-coding polynucleotide sequences/regions comprises contacting the biological sample with an agent for detecting mutation in the one or more non-coding polynucleotide sequences/regions. In some embodiments, the agent may include but is not limited to primers, probes, capture agents, dyes, labels, nucleotides, salts, buffering agents, various additives, PCR enhancers and combinations thereof. In some embodiments therefore, the determining step comprises contacting the biological sample with a primer/probe for hybridizing under stringent conditions to the one or more non-coding polynucleotide sequences/regions.

In various embodiments, the probe/primer comprises a sequence having at least about 75%, at least about 80%, at least about 85%, at least about 90%, at least about 85% or at least about 99% sequence identity to a sequence set forth in SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56, SEQ ID NO. 57, SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91 or SEQ ID NO. 92. It is understood that other probes/primers, which may be obtained by persons of ordinary skill in the art based on the sequences of the one or more non-coding polynucleotide sequences/regions, and based on well-known criteria for designing sequence specific probes/primers, may also be used.

In various embodiments, determining whether mutation is present in at least one of the CBS overlapping regions or portions or flanking sequences thereof comprises contacting the biological sample with an agent, optionally a primer for detecting mutation in at least one of the CBS overlapping regions set forth in Table 2, or portions or flanking sequences. In various embodiments, determining whether mutation is present in at least one of the CBS overlapping regions or portions or flanking sequences thereof comprises contacting the biological sample with a primer having at least about 85% sequence identity to a sequence selected from the group consisting of: SEQ ID NO. 35, SEQ ID NO. 36, SEQ ID NO. 39, SEQ ID NO. 40, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 57, SEQ ID NO. 58, SEQ ID NO. 59, SEQ ID NO. 60, SEQ ID NO. 65, SEQ ID NO. 66, SEQ ID NO. 77, SEQ ID NO. 78, SEQ ID NO. SEQ ID NO. 83, SEQ ID NO. 84 and combinations thereof. In various embodiments, determining whether mutation is present in at least one of the CBS overlapping regions comprises contacting the biological sample with a primer pair having at least about 85% sequence identity to a pair of sequences such as but is not limited to SEQ ID NOs. 35 and 36, SEQ ID NOs. 39 and 40, SEQ ID NOs. 45 and 46, SEQ ID NOs. 47 and 48, SEQ ID NOs. 49 and 50, SEQ ID NOs. 51 and 52, SEQ ID NOs. 57 and 58, SEQ ID NOs. 59 and 60, SEQ ID NOs. 65 and 66, SEQ ID NOs. 77 and 78, and SEQ ID NOs. 83 and 84, and the like.

In various embodiments, determining whether mutation is present in at least one of the non-CBS regions or portions or flanking sequences thereof comprises contacting the biological sample with an agent, optionally a primer for detecting mutation in at least one of the non-CBS regions set forth in Table 3, or portions or flanking sequences. In various embodiments, determining whether mutation is present in at least one of the non-CBS regions, or portions or flanking sequences thereof, comprises contacting the biological sample with a primer having at least about 85% sequence identity to a sequence selected from the group consisting of: SEQ ID NO. 37, SEQ ID NO. 38, SEQ ID NO. 41, SEQ ID NO. 42, SEQ ID NO. 43, SEQ ID NO. 44, SEQ ID NO. 53, SEQ ID NO. 54, SEQ ID NO. 55, SEQ ID NO. 56, SEQ ID NO. 61, SEQ ID NO. 62, SEQ ID NO. 63, SEQ ID NO. 64, SEQ ID NO. 67, SEQ ID NO. 68, SEQ ID NO. 71, SEQ ID NO. 72, SEQ ID NO. 75, SEQ ID NO. 76, SEQ ID NO. 81, SEQ ID NO. 82, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, and combinations thereof. In various embodiments, determining whether mutation is present in at least one of the non-CBS regions comprises contacting the biological sample with a primer pair having at least about 85% sequence identity to a pair of sequence such as but is not limited to SEQ ID NOs. 37 and 38, SEQ ID NOs. 41 and 42, SEQ ID NOs. 43 and 44, SEQ ID NOs. 53 and 54, SEQ ID NOs. 55 and 56, SEQ ID NOs. 61 and 62, SEQ ID NOs. 63 and 64, SEQ ID NOs. 67 and 68, SEQ ID NOs. 69 and 70, SEQ ID NOs. 71 and 72, SEQ ID NOs. 73 and 74, SEQ ID NOs. 75 and 76, SEQ ID NOs. 79 and 80, SEQ ID NOs. 81 and 82, SEQ ID NOs. 85 and 86, SEQ ID NOs. 87 and 88, SEQ ID NOs. 89 and 90, and SEQ ID NOs. 91 and 92, and the like.

In various embodiments, there is provided a kit comprising an agent, for hybridising under stringent conditions to the one or more non-coding polynucleotide sequences/regions or for hybridising to a polynucleotide having at least about 75%, at least about 80%, at least about 85%, at least about 90%, at least about 85% or at least about 99% sequence identity to the one or more non-coding polynucleotide sequences/regions. In some embodiments, the agent may include but is not limited to primers, probes, capture agents, dyes, labels, nucleotides, salts, buffering agents, various additives, PCR enhancers and combinations thereof.

In various embodiments, there is provided a kit for detecting gastrointestinal cancer in a human subject, the kit comprising an agent for detecting mutation in the one or more non-coding polynucleotide sequences/regions set forth in Table 1 or portions or flanking sequences thereof. In some embodiments, the agent, comprises a sequence having at least about 75%, at least about 80%, at least about 85%, at least about 90%, at least about 85% or at least about 99% sequence identity to a sequence set forth in SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56, SEQ ID NO. 57, SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91 or SEQ ID NO. 92.

In various embodiments, there is provided a kit for detecting gastrointestinal cancer in a human subject, the kit comprising: an agent for detecting mutation in at least one of the CBS overlapping regions set forth in Table 2 or portions or flanking sequences thereof, or in at least one of the non-regions set forth in Table 3 or portions or flanking sequences thereof. In some embodiments, there is provided a kit for detecting gastrointestinal cancer in a human subject, the kit comprising an agent for detecting mutation in at least one of the CBS overlapping regions set forth in Table 2 or portions or flanking sequences thereof. In some embodiments, the agent for detecting mutation in at least one of the CBS overlapping regions, or portions or flanking sequences thereof, comprises a primer having at least about 85% sequence identity to a sequence such as but is not limited to SEQ ID NO. 35, SEQ ID NO. 36, SEQ ID NO. 39, SEQ ID NO. 40, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 57, SEQ ID NO. 58, SEQ ID NO. 59, SEQ ID NO. 60, SEQ ID NO. 65, SEQ ID NO. 66, SEQ ID NO. 77, SEQ ID NO. 78, SEQ ID NO. SEQ ID NO. 83 and SEQ ID NO. 84, and the like. In some embodiments, the kit comprises a primer pair having at least about 85% sequence identity to a pair of sequences selected from the group consisting of SEQ ID NOs. 35 and 36, SEQ ID NOs. 39 and 40, SEQ ID NOs. 45 and 46, SEQ ID NOs. 47 and 48, SEQ ID NOs. 49 and 50, SEQ ID NOs. 51 and 52, SEQ ID NOs. 57 and 58, SEQ ID NOs. 59 and 60, SEQ ID NOs. 65 and 66, SEQ ID NOs. 77 and 78, and SEQ ID NOs. 83 and 84. In some embodiments, the kit comprises primer pairs having the following sequences: SEQ ID NOs. 35 and 36 or a pair of sequences having at least about 85% sequence identity thereto; SEQ ID NOs. 39 and 40 or a pair of sequences having at least about 85% sequence identity thereto; SEQ ID NOs. 45 and 46 or a pair of sequences having at least about 85% sequence identity thereto; SEQ ID NOs. 47 and 48 or a pair of sequences having at least about 85% sequence identity thereto; SEQ ID NOs. 49 and 50 or a pair of sequences having at least about 85% sequence identity thereto; and SEQ ID NOs. 51 and 52 or a pair of sequences having at least about 85% sequence identity thereto. In some embodiments, the kit comprises agents for detecting mutation in at least two of the CBS overlapping regions, or portions or flanking sequences thereof, set forth in Table 2. In some embodiments, the kit comprises agents for detecting mutation in all of the CBS overlapping regions, or portions or flanking sequences thereof, set forth in Table 2. In some embodiments, the kit comprises agents for detecting mutation in all of the CBS overlapping regions, or portions or flanking sequences thereof, and all of the non-CBS regions, or portions or flanking sequences thereof, set forth in Tables 2 and 3.

In some embodiments, the kit further comprises an agent for detecting mutation in at least one of the non-CBS regions set forth in Table 3 or portions or flanking sequences thereof. In some embodiments, there is provided a kit for detecting gastrointestinal cancer in a human subject, the kit comprising an agent for detecting mutation in at least one of the CBS overlapping regions set forth in Table 3 or portions or flanking sequences thereof. In some embodiments, the agent for detecting mutation in at least one of the non-CBS regions, or portions or flanking sequences thereof, comprises a primer having at least about 85% sequence identity to a sequence selected from the group consisting of: SEQ ID NO. 37, SEQ ID NO. 38, SEQ ID NO. 41, SEQ ID NO. 42, SEQ ID NO. 43, SEQ ID NO. 44, SEQ ID NO. 53, SEQ ID NO. 54, SEQ ID NO. 55, SEQ ID NO. 56, SEQ ID NO. 61, SEQ ID NO. 62, SEQ ID NO. 63, SEQ ID NO. 64, SEQ ID NO. 67, SEQ ID NO. 68, SEQ ID NO. 71, SEQ ID NO. 72, SEQ ID NO. 75, SEQ ID NO. 76, SEQ ID NO. 81, SEQ ID NO. 82, SEQ ID NO. 85, SEQ ID NO. 86, SEQ ID NO. 87, SEQ ID NO. 88, SEQ ID NO. 89, SEQ ID NO. 90, SEQ ID NO. 91 and SEQ ID NO. 92. In some embodiments, the kit comprises a primer pair having at least about 85% sequence identity to a pair of sequences such as but is not limited to SEQ ID NOs. 37 and 38, SEQ ID NOs. 41 and 42, SEQ ID NOs. 43 and 44, SEQ ID NOs. 53 and 54, SEQ ID NOs. 55 and 56, SEQ ID NOs. 61 and 62, SEQ ID NOs. 63 and 64, SEQ ID NOs. 67 and 68, SEQ ID NOs. 69 and 70, SEQ ID NOs. 71 and 72, SEQ ID NOs. 73 and 74, SEQ ID NOs. 75 and 76, SEQ ID NOs. 79 and 80, SEQ ID NOs. 81 and 82, SEQ ID NOs. 85 and 86, SEQ ID NOs. 87 and 88, SEQ ID NOs. 89 and 90, and SEQ ID NOs. 91 and 92, and the like.

In various embodiments, the probe/primer is no more than about 30 bp, no more than about 29 bp, no more than about 28 bp, no more than about 27 bp, no more than about 26 bp, no more than about 25 bp, no more than about 24 bp, no more than about 23 bp, no more than about 22 bp, no more than about 21 bp, no more than about 20 bp, no more than about 19 bp, no more than about 18 bp, no more than about 17 bp, no more than about 16 bp, no more than about 15 bp, no more than about 14 bp, no more than about 13 bp, no more than about 12 bp, no more than about 11 bp, no more than about 10 bp, no more than about 9 bp, no more than about 8 bp, no more than about 7 bp, no more than about 6 bp or no more than about 5 bp in length.

In various embodiments, the kit further comprises a probe/primer for hybridising to a gene sequence. In some embodiments, the gene is selected form the group consisting of: KRAS, TP53, RHOA, ARID1A, PIK3CA, ERBB3, PTEN and HLA-B. 1. In some embodiments, the kit further comprises an agent for detecting mutation in at least one of the genes selected from the group consisting of: KRAS, TP53, RHOA, ARID1A, PIK3CA, ERBB3 and PTEN. In some embodiments, the kit further comprises an agent for detecting mutation in at least one of the genes selected from the group consisting of: KRAS, TP53 and RHOA.

In various embodiments, the kit comprises at least about 10, at least about 20, at least about 30, at least about 40, at least about 50, at least about 60 or at least about 68 probes/primers.

In various embodiments, there is also provided an isolated nucleic acid or polynucleotide comprising a mutation in each of the one or more non-coding polynucleotide sequences/regions set forth in Table 1, or a polynucleotide having at least about 75%, at least about 80%, at least about 85%, at least about 90%, at least about 85% or at least about 99% sequence identity with each of the one or more non-coding polynucleotide sequences/regions set forth in Table 1.

In various embodiments, there is provided a method, product or use as described herein.

The horizontal lines mark the Bonferroni adjusted P-values of 0.01 and 1% FDR respectively.

Figure 12:
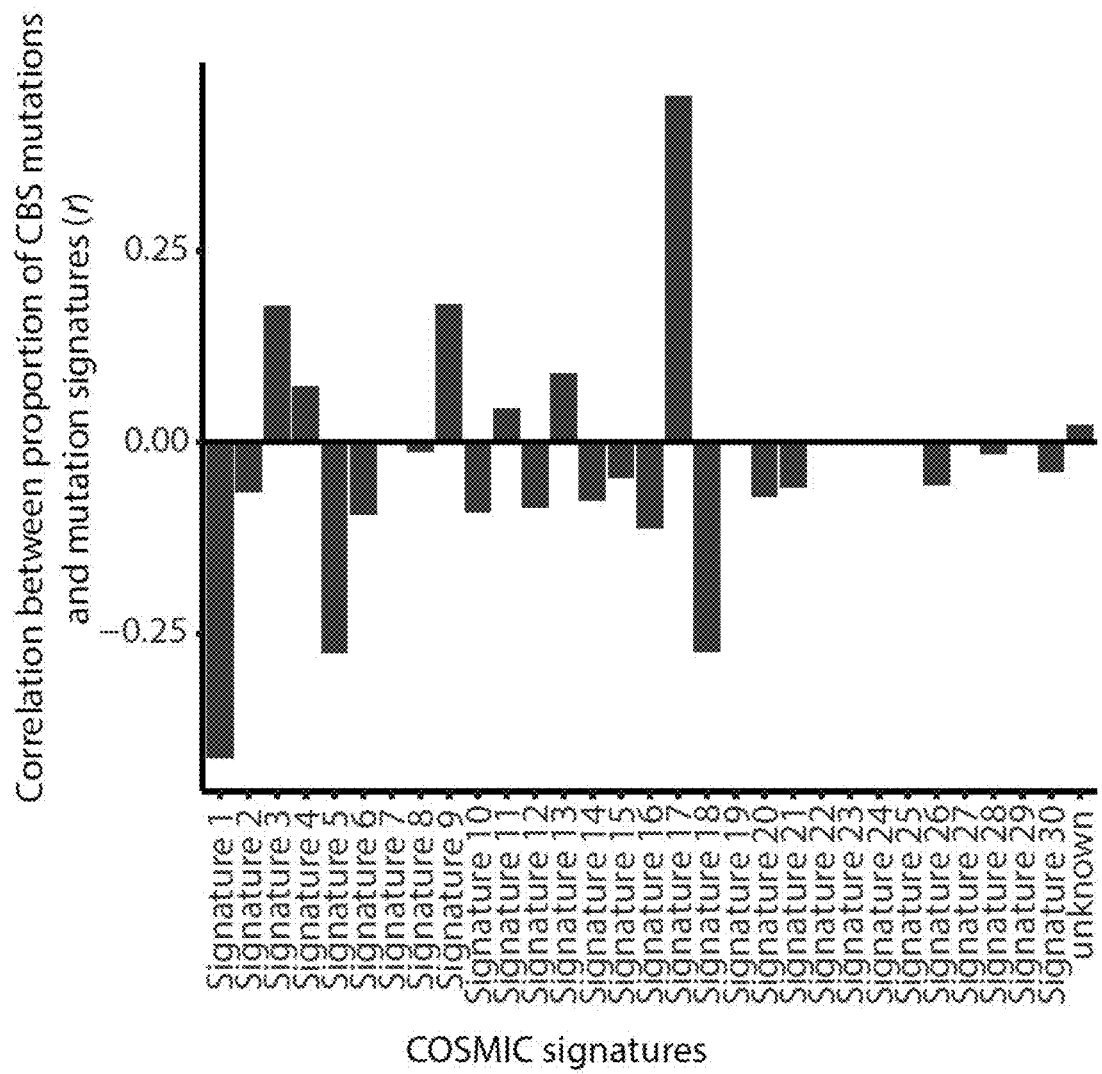
Figure 13A:
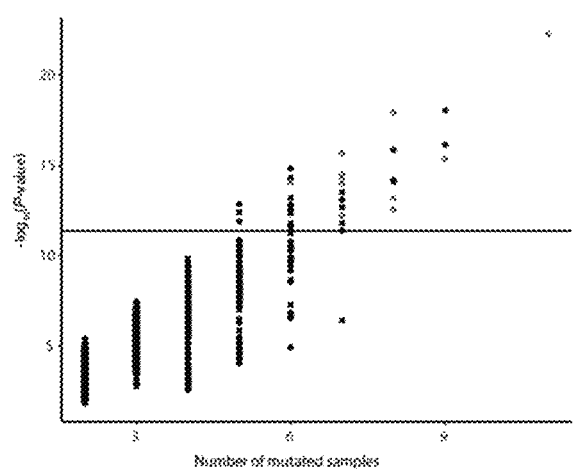
Figure 13B:
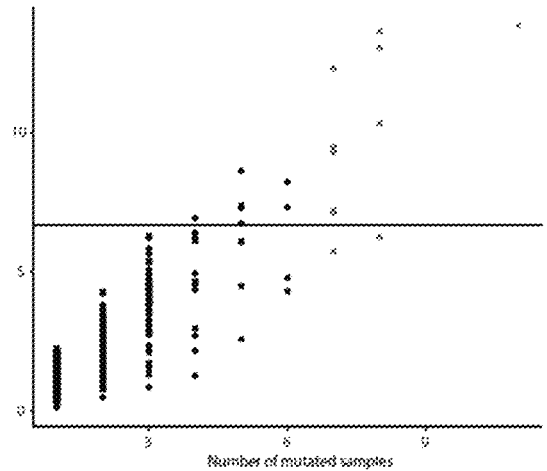
Figure 13C:
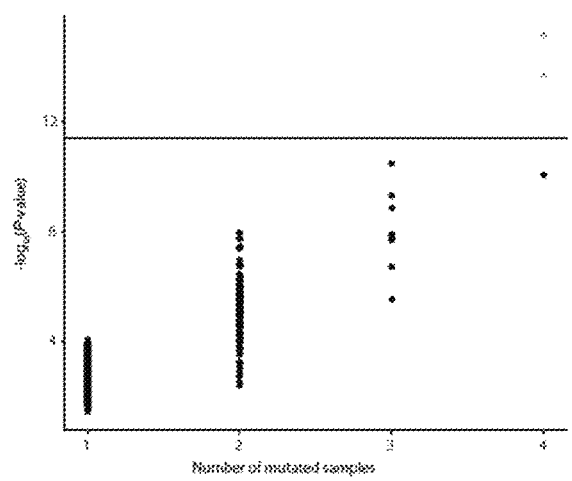
Figure 13D:
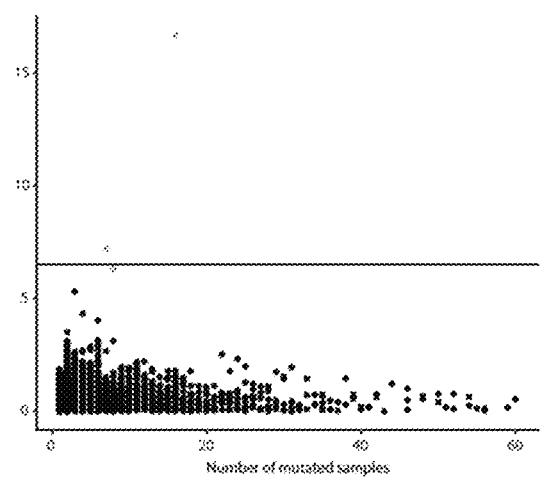

FIG. 12 shows the correlation between CBS mutation rate of each sample with COSMIC signatures.

FIG. 13 shows the negative log P-values of mutation recurrence plotted against the number of mutated samples in each non-coding region. (A) Genome-wide SNV hotspot model. Significantly mutated hotspots overlapping CBSs are highlighted in grey. (B) CBS-specific model. CBS hotspots identified in (A) are highlighted in grey. (C) Genome-wide indel hotspot model. 2 significantly mutated regions are highlighted in grey. (D) Gene-based indel recurrence model. 3 significantly mutated genes are highlighted in grey.

FIG. 14 shows the distribution of mutations within each CBS hotspot. (A-R) Somatic substitution patterns within each CBS hotspot. CBS hotspots identified from genome-wide analysis of non-coding SNV hotspots are highlighted in grey. Y-axis shows the mutation count and x-axis shows the position relative to CTCF motif.

Figure 15:
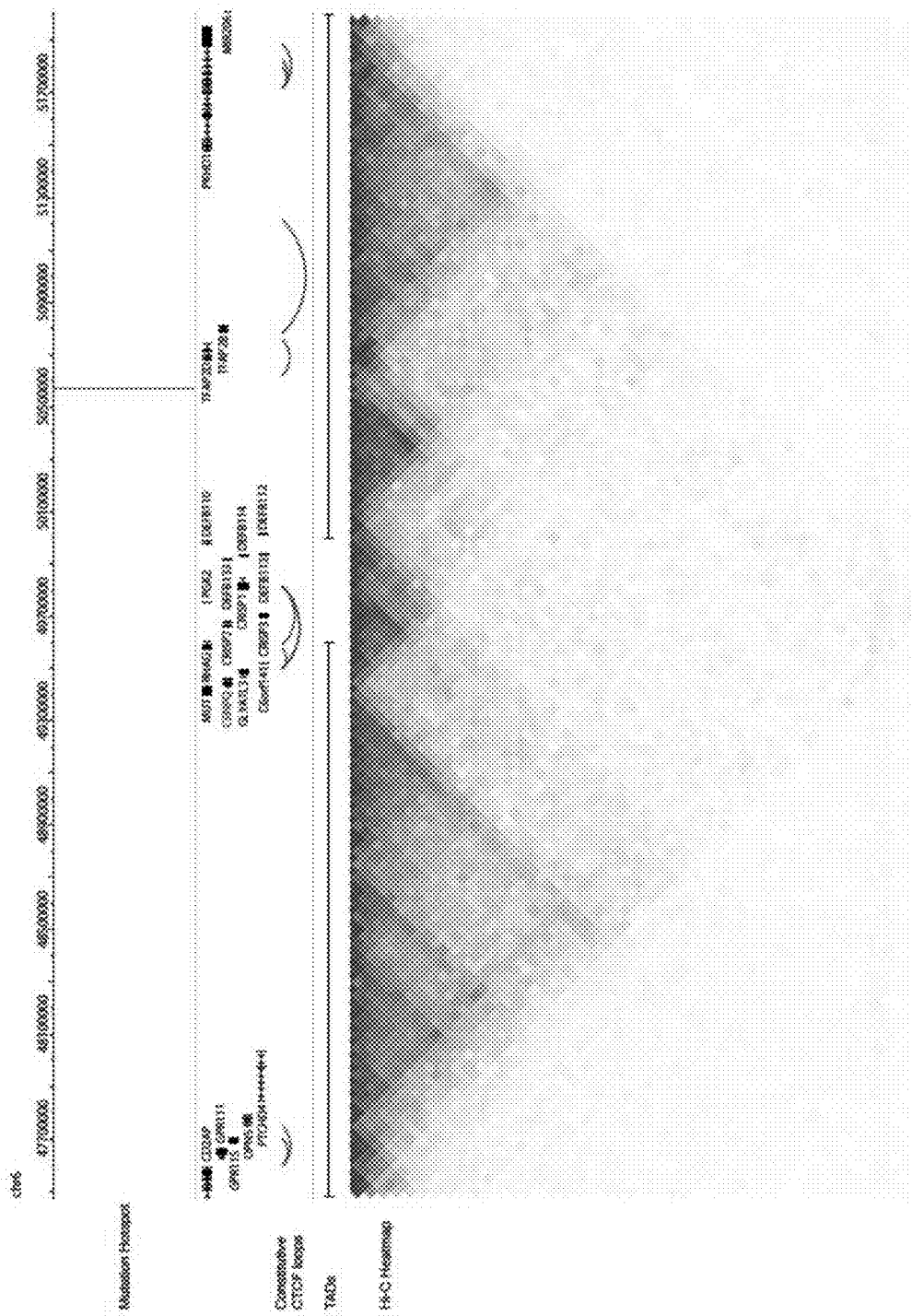

FIG. 15 shows the chromatin neighborhood of the CBS hotspot at chr6:50570094-50570120. Candidate gene with expression change associated with the mutation status of the hotspot is highlighted in grey. The archs represent constitutive CTCF loops defined by Hnisz et al., *Science*, 2016. The heatmap shows the normalized Hi-C interaction frequencies in IMR90 cells (Dixon et al., *Nature*, 2012). TADs were called by Dixon et al., *Nature*, 2012.

Figure 16:
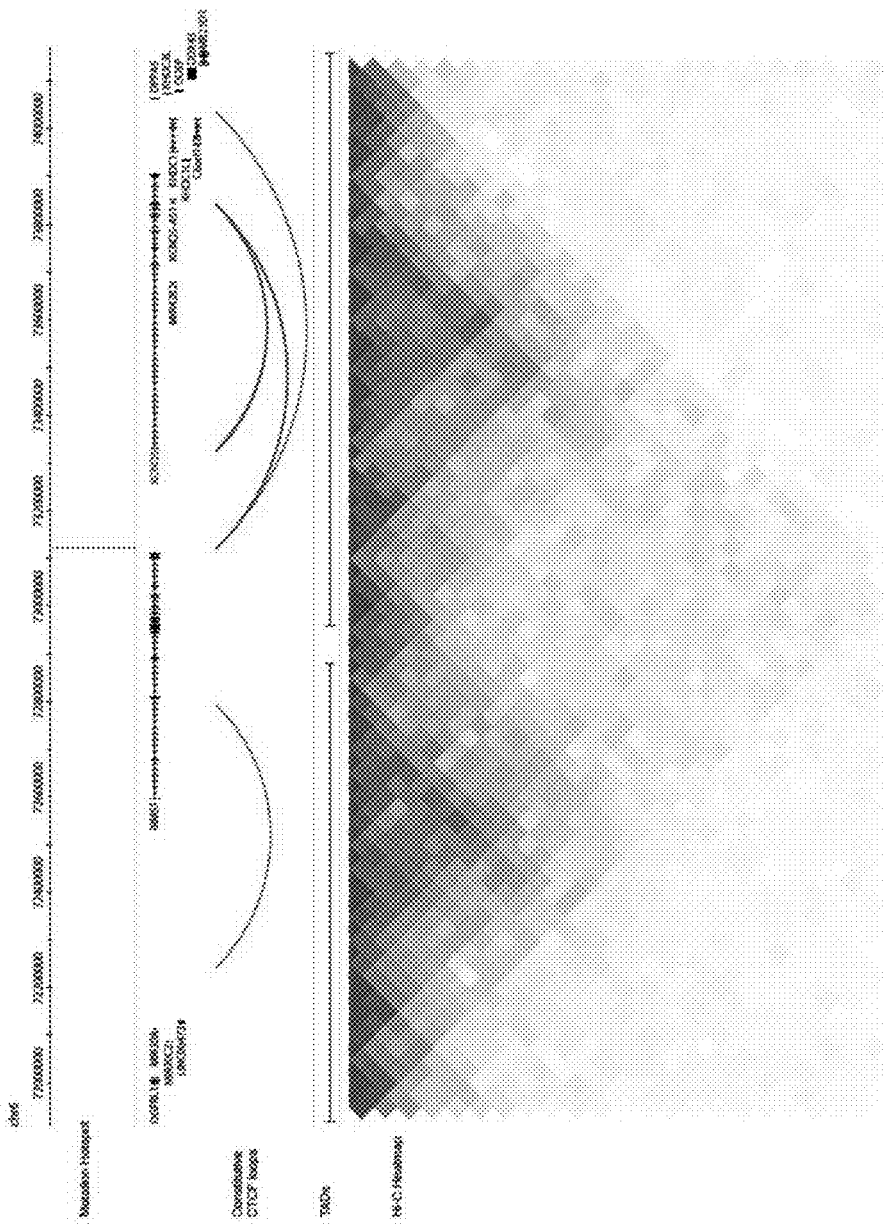

FIG. 16 shows the chromatin neighborhood of the CBS hotspot at chr6:73122084-73122123. Candidate gene with expression change associated with the mutation status of the hotspot is highlighted in grey. The archs represent constitutive CTCF loops defined by Hnisz et al., *Science*, 2016. The heatmap shows the normalized Hi-C interaction frequencies in IMR90 cells (Dixon et al., *Nature*, 2012). TADs were called by Dixon et al., *Nature*, 2012.

Figure 17:
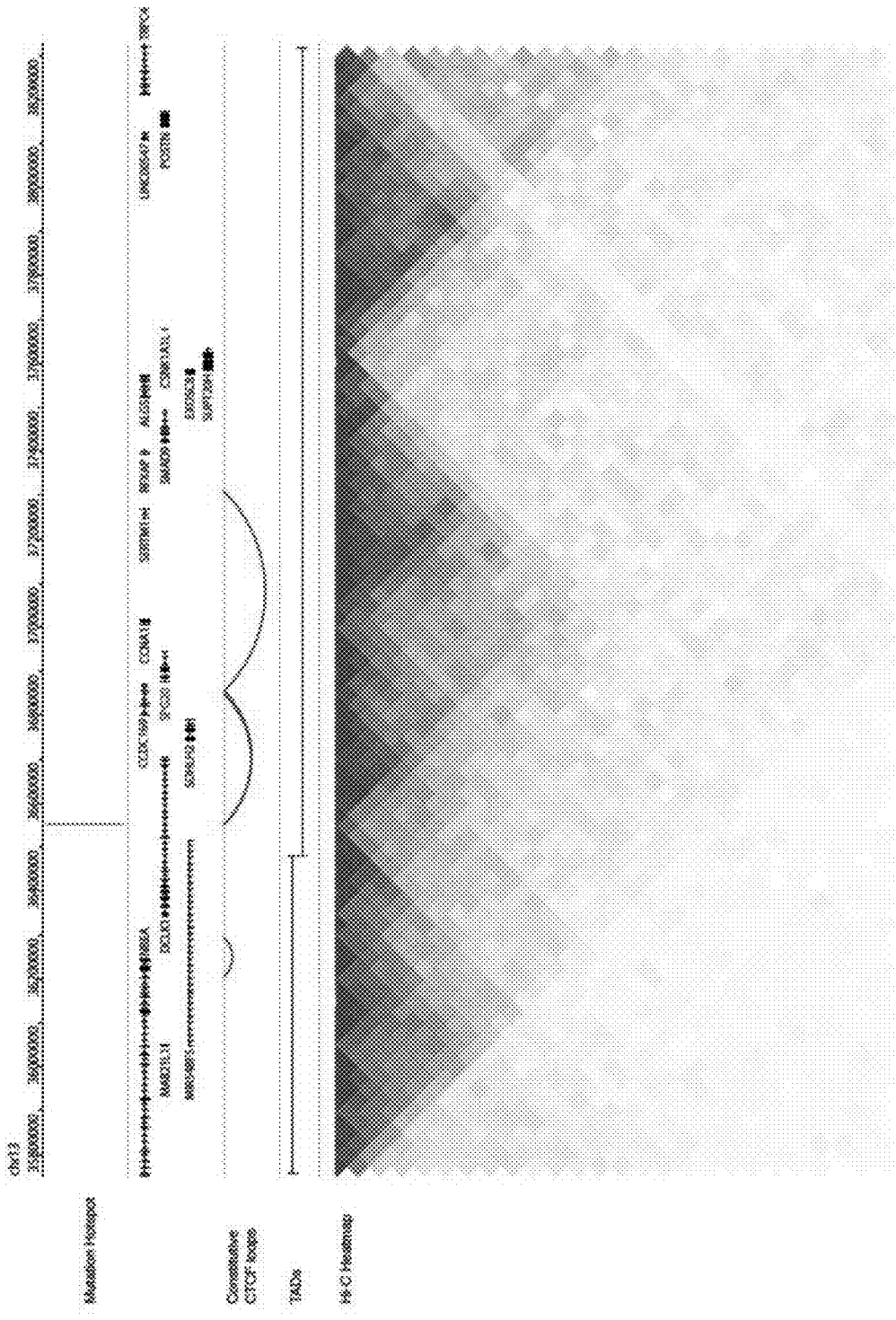

FIG. 17 shows the chromatin neighborhood of CBS hotspot at chr13:36552821-36552860. Candidate gene with expression change associated with the mutation status of the hotspot is highlighted in grey. The archs represent constitutive CTCF loop defined by Hnisz et al., *Science*, 2016. The heatmap shows the normalized Hi-C interaction frequencies in IMR90 cells (Dixon et al., *Nature*, 2012). TADs were called by Dixon et al., *Nature*, 2012.

FIG. 18 shows the correlation between CBS hotspot mutations and the expression of candidate genes using expression data from 14 tumors of the Singapore cohort. (A-C) The gene expressions of CENPQ (A), KCNQ5 (B) and SPG20 (C) in matched normal gastric tissue, tumors wildtype at the corresponding CBS hotspot and tumors mutated at the corresponding CBS hotspot. Wilcoxon ranksum test P-values are shown.

Figure 19C:
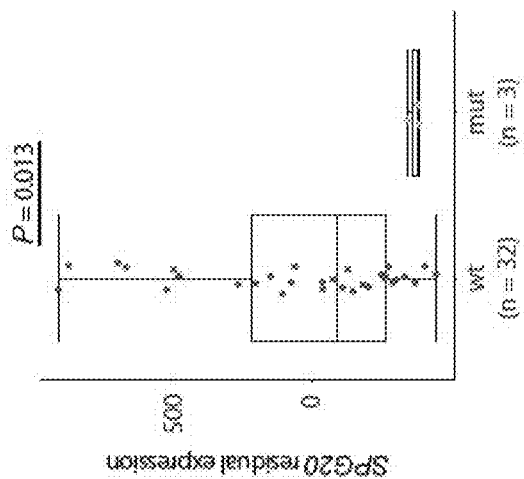
Figure 19B:
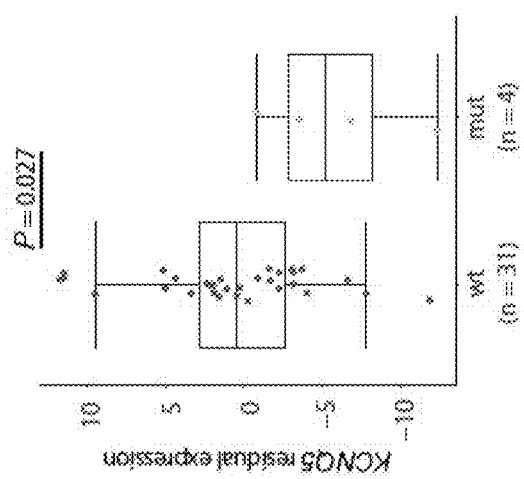
Figure 19A:
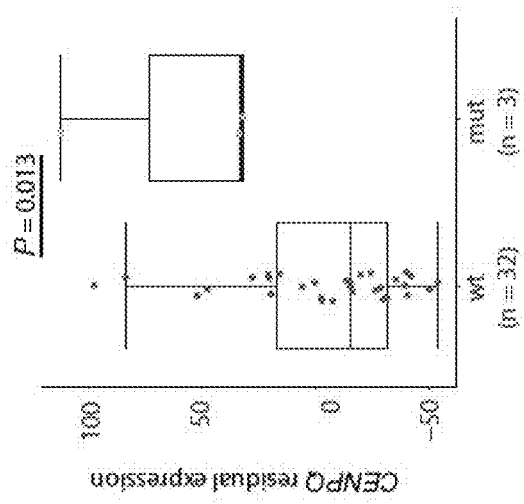

FIG. 19 shows the correlation between CBS hotspot mutations and the residual expression of candidate genes after correcting for tumor purity and copy number. (A-C) The gene expressions of CENPQ (A), KCNQ5 (B) and SPG20 (C) in tumors wildtype at the corresponding CBS hotspot and tumors mutated at the corresponding CBS hotspot. Wilcoxon rank-sum test P-values are shown.

FIG. 20 shows the evolutionary conservation of the consensus CTCF motif and flanking sequences. (A) Average PhyloP scores of the CTCF-binding motif and ±5 flanking bases of all mutated CBSs. (B-C) Two CBS hotspots (B relates to a hotspot upstream of CENPQ) where mutations at 5' flanks of CTCF-binding motifs coincide with conserved bases.

Figure 21:
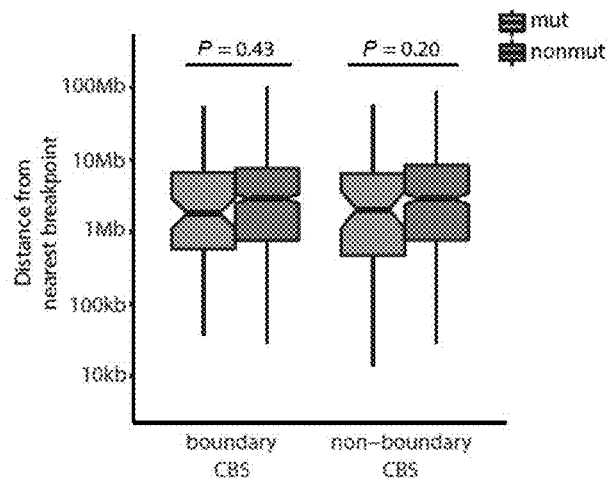

FIG. 21 shows the distance to the nearest CNV breakpoint from CBSs at loop boundary and non-boundary CBSs for GS tumors.

Figure 22:
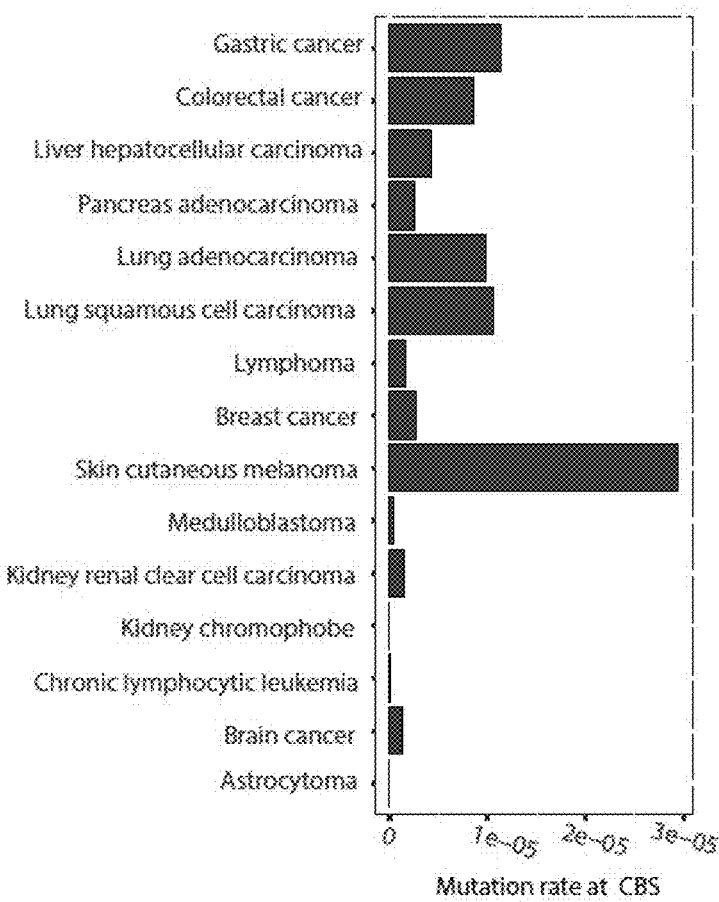

FIG. 22 shows the mutation rate of tissue-specific CBSs in different cancer types.

Figure 23:
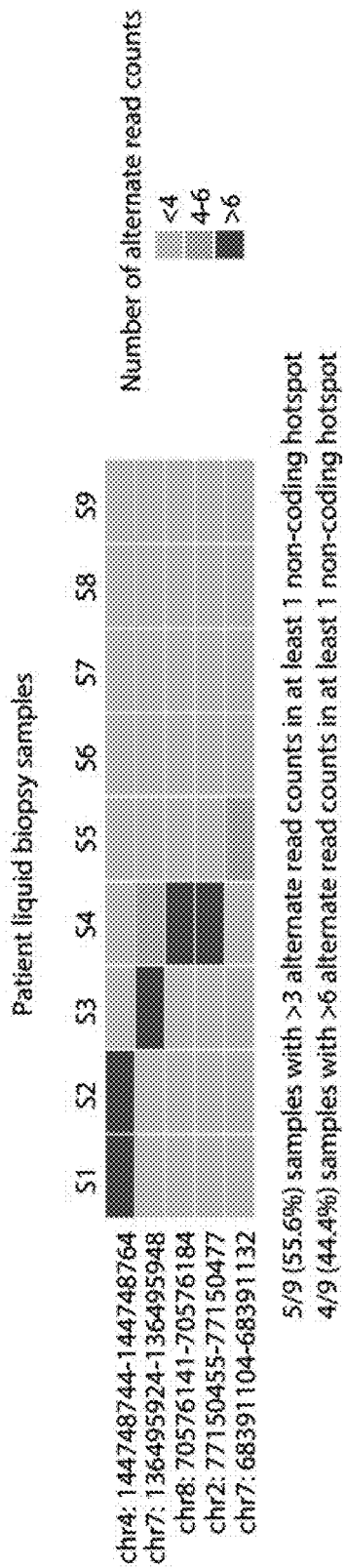

FIG. 23 is an oncoplot showing that mutations were detected in at least one non-coding hotspot in 44-56% of 9 liquid biopsy samples from colorectal cancer patients.

EXAMPLES

Example embodiments of the disclosure will be better understood and readily apparent to one of ordinary skill in the art from the following examples, tables and if applicable, in conjunction with the figures. The example embodiments should not be construed as limiting the scope of the disclosure.

The Mutation Landscape of Gastric Adenocarcinoma

Figure 1A:
FIG. 1 is a summary of the data. (A) Gastric tumor samples were grouped by cohort and ordered by SNV count within each cohort. The panels show coverage, SNV count, indel count, mutation spectrum, molecular subtype and Lauren's classification of each sample. (B) Correlations between epigenetic features and somatic mutation rates in different tumor subtypes. Error bars represent s.e.m of the correlation coefficient. (C) Principle component analysis of contributions of epigenetic features to the variance in the mutation rate of individual tumours. Stacked bars show the contribution of individual epigenetic features to the first two principal components.
Figure 8A:
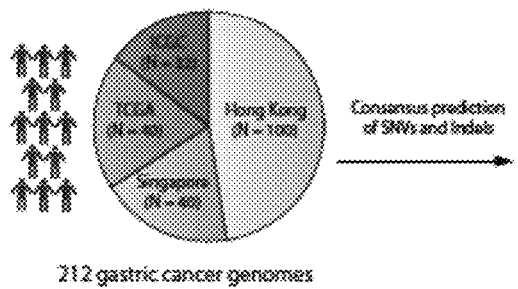
FIG. 8 is a summary of mutation data of 212 gastric cancer genomes. (A) A total of 212 gastric cancer whole genome sequences were collated from 4 sources and uniformly processed to obtain high-confidence somatic mutation calls. (B) Mutation count and coverage of individual tumors from the 4 cohorts. (C) Individual samples were plotted by their mutation counts on the y-axis against the fractions of C.G>A.T mutations on the x-axis. Seven samples were removed due to data corruption. Thirteen tumors with low mutation counts were removed, as these are likely low-quality samples. Finally, 5 samples showing signature of oxidative DNA damage (high fraction of C.G>A.T mutations) were removed. (D) The mutation spectrums of tumors from the 4 cohorts are similar after uniform alignment and mutation calling.
Figure 8B:
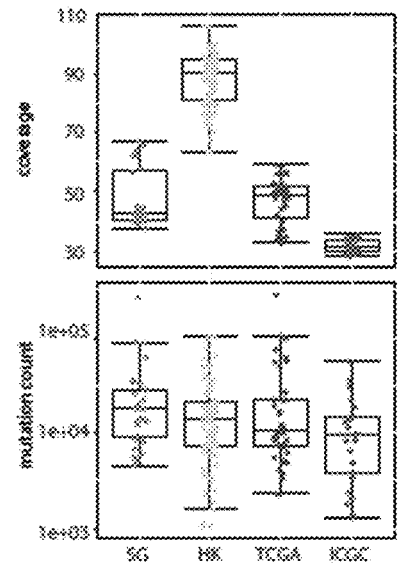
Figure 8C:
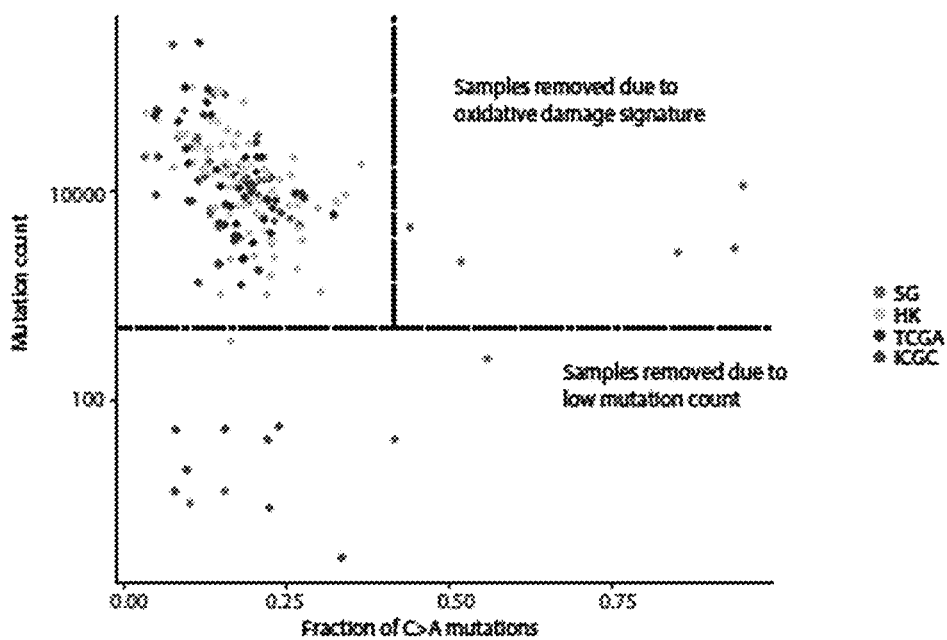
Figure 8D:
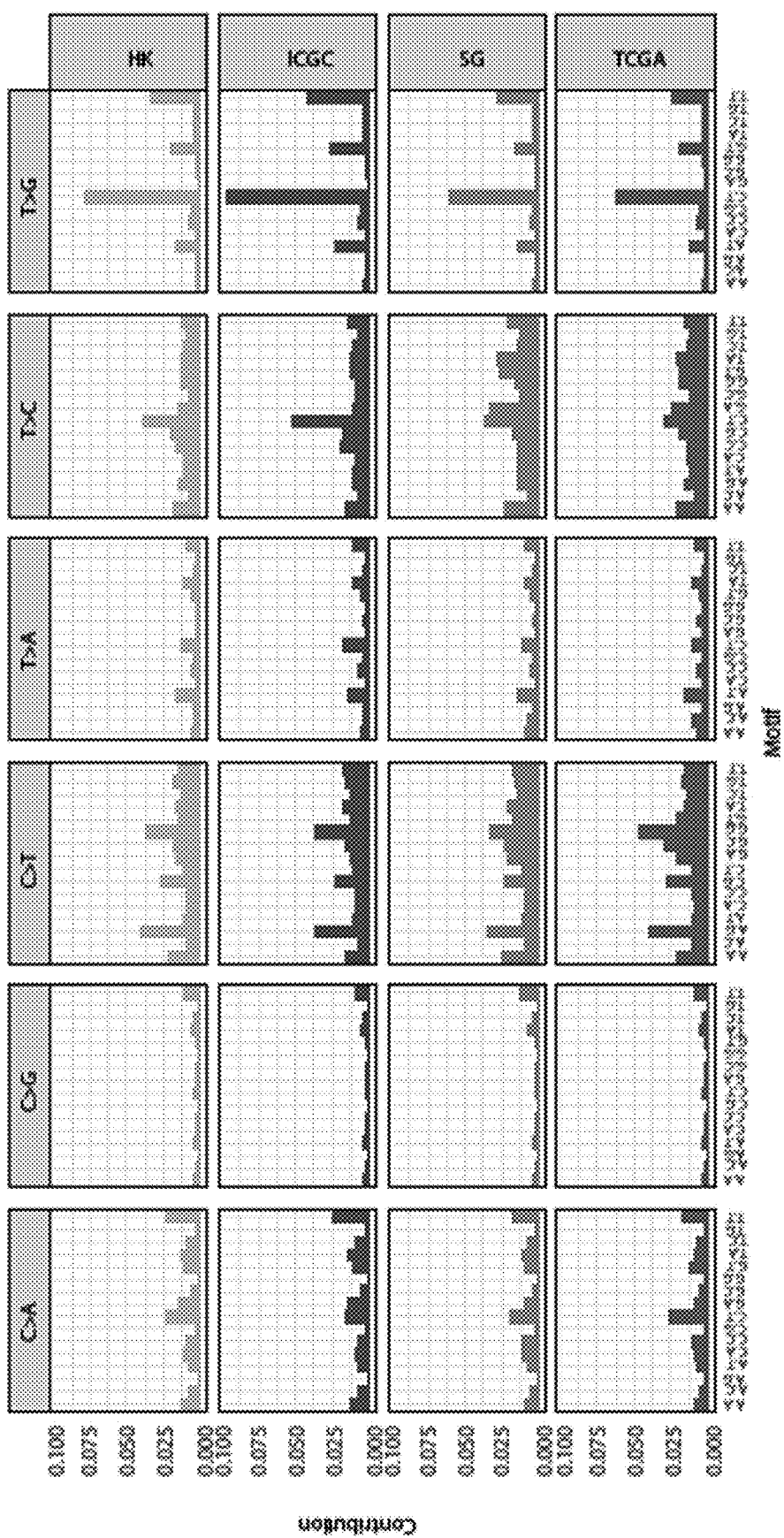

The whole genome sequences of 212 gastric adenocarcinoma tumors and matched normal samples collated from four different sources were analysed (data not shown). All samples were uniformly processed using an accurate somatic mutation calling pipeline (FIG. 8A-B). Briefly, a random forest classifier that predicts high confidence somatic mutation calls (SNVs and indels) was trained by combining the outputs of four independent mutation callers. This approach achieved >85% accuracy on an independent test data set of curated somatic mutations. 20 low quality samples with less than 400 mutation calls were excluded from the discovery cohort (FIG. 8C). In addition, 5 samples with strong enrichment of C>A substitutions (a sign of oxidative damage during DNA preparation) were removed (FIG. 8C). Somatic mutations in CDS regions, immunoglobin loci and poorly mappable regions were also removed from further analyses. After uniform processing, samples from the four cohorts showed comparable distributions of somatic mutation counts and similar mutation spectra (FIG. 1A and FIG. 8A). The ICGC cohort had slightly fewer mutations per tumor, probably due to the lower sequencing depth of this cohort.

Figure 1C:
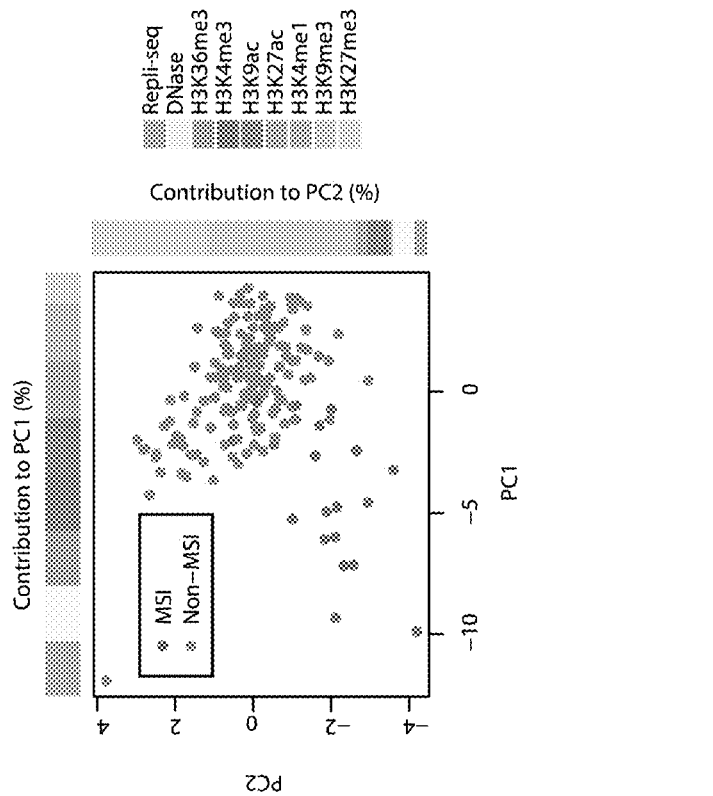
Figure 1B:
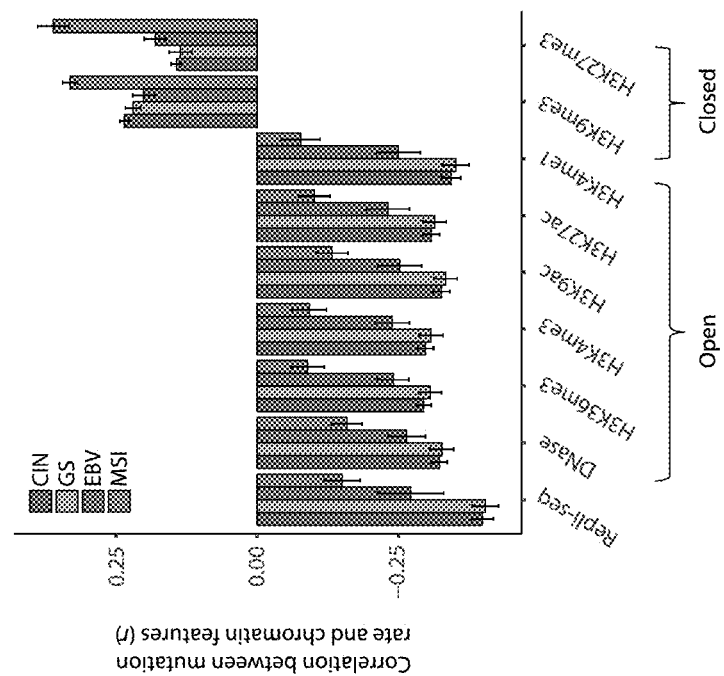

A previous study identified four molecular subtypes of gastric adenocarcinoma: tumors that are EBV positive (EBV), tumors with high levels of microsatellite instability (MSI), tumors that exhibit copy number instability (CIN), and tumor that are genomically stable (GS). The correlations between somatic mutation rates of the four cancer subtypes and epigenetic profiles of gastric tissue obtained from the Roadmap Epigenomics project were investigated. In general, somatic mutation rates were negatively correlated with regions of open chromatin (DNaseI hypersensitivity) and histone marks of active promoters (H3K4me3) and enhancers (H3K27ac) (FIG. 1B). The depletion of somatic mutations in regions of open chromatin is likely due to enhanced accessibility to the DNA repair machinery. Notably, somatic mutations in the EBV subtype were less correlated with histone features and replication timing compared to the CIN and GS subtypes, suggesting that additional mutational biases may exist in EBV infected tumors.

Tumors belonging to the MSI subtype displayed strikingly different associations between epigenetic features and mutation patterns. There was little association observed between mutation rate and open chromatin marks or replication timing in MSI tumors. This is likely because mismatch repair (MMR) deficient MSI tumors have been shown to lose MMR-coupled enhanced repair efficiency at early-replicating open-chromatin regions. Additionally, it was found that MSI mutation profiles showed a strong positive association with heterochromatin (H3K9me3) and repressive domains (H3K27me3) (FIG. 1B). This is in contrast with a previous study reporting that mutations generated after MMR inactivation are no longer enriched in heterochromatin regions, arguing that genome-wide regional mutation rate variation is mostly a result of MMR. Instead, the present data suggests that, in addition to MMR, other repair or mutational processes may further contribute to variation of the GC mutation landscape. Principal component analysis (PCA) on the correlation matrix between the mutation profiles of individual tumors and the epigenetic covariates also revealed MSI tumors as a distinct cluster (FIG. 1C). Accordingly, the small number of MSI tumors (N=19) were removed from the discovery cohort to ensure all tumors had similar mutational biases.

Statistical Framework for Mutational Hotspot Identification

Figure 2A:
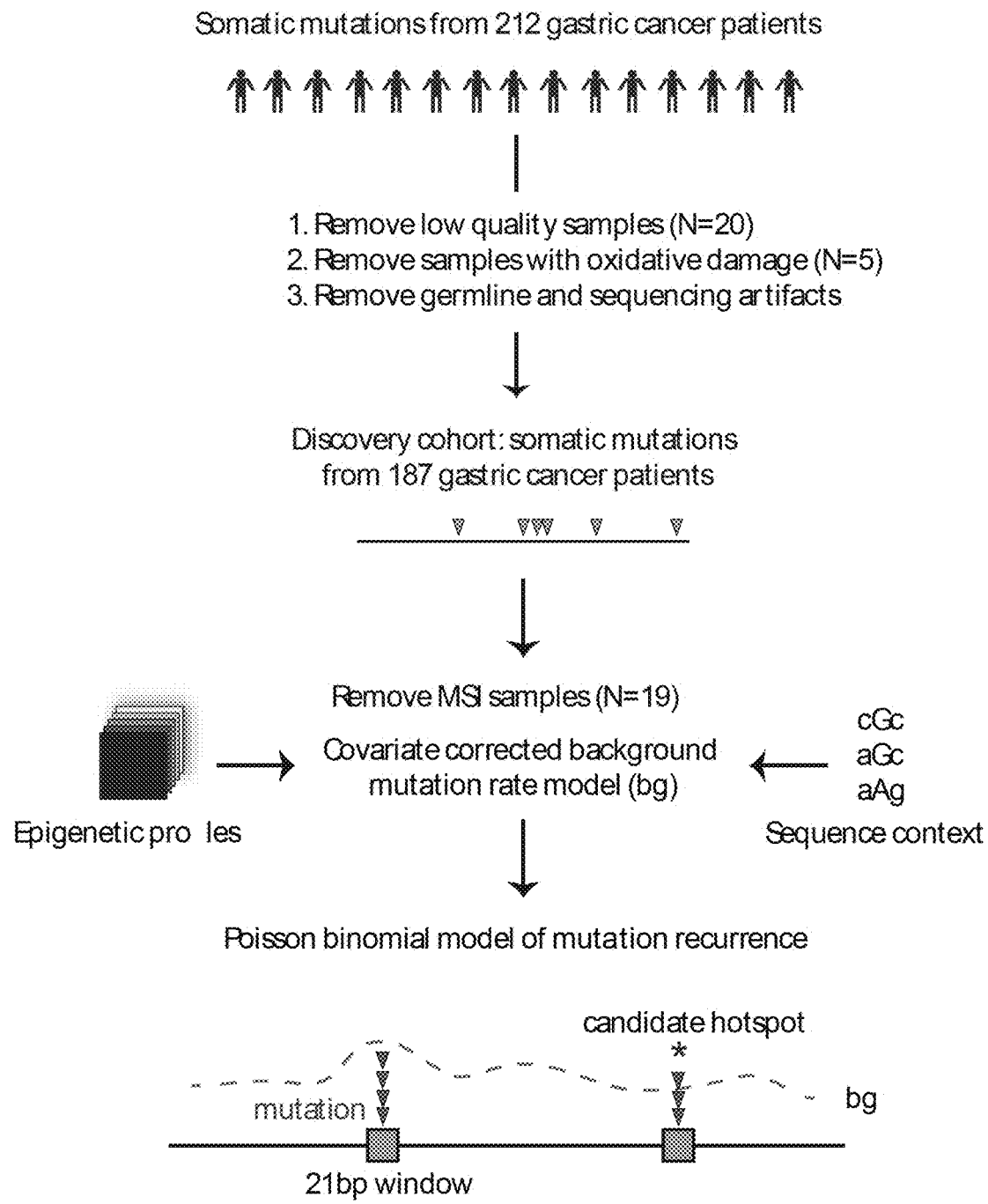
FIG. 2 shows the genome-wide analysis of non-coding indel recurrence. (A) Workflow of the method to detect recurrently mutated non-coding regions. (B) Genome-wide negative log P-values of indel recurrence of 21 bp regions with at least 1 indel. The horizontal line marks the Bonferroni adjusted P-value of 0.01. (C) Negative log P-value of indel recurrence in merged non-coding regions of each gene. The top 3 significantly mutated genes are highlighted. The horizontal line marks the Bonferroni adjusted P-value of 0.01. (D-F) Gene expression of LIPF (D), PGC (E) and MUC6 (f) in normal gastric samples, tumors wildtype for the gene of interest, and tumors with non-coding indels in the gene of interest.
Figures 9A, 9B, 9C:
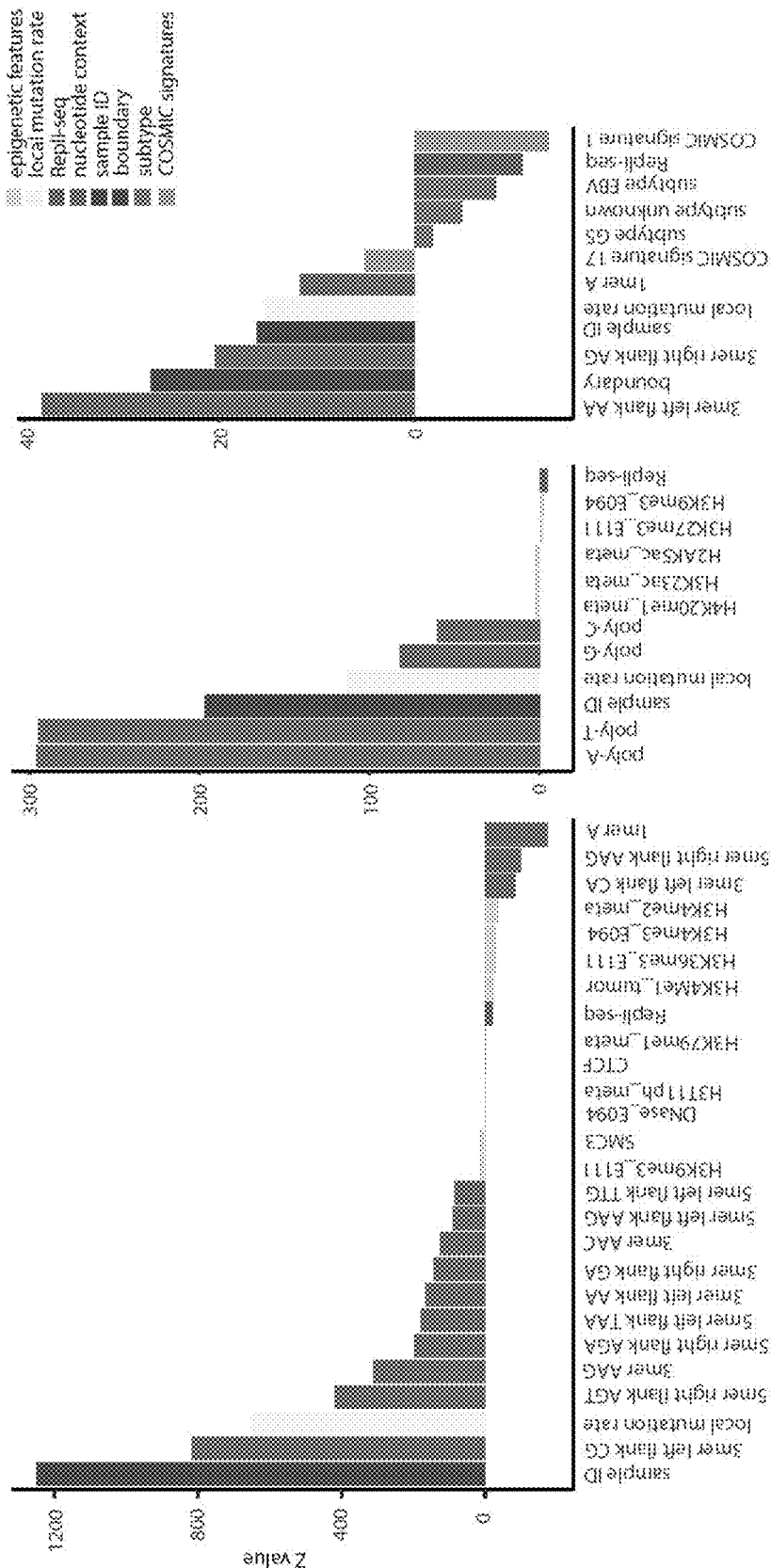
FIG. 9 shows the features used in each background mutation model. Sequence and epigenetic features that are most correlated with somatic mutation rates were selected by LASSO regression. Selected features in the (A) SNV background model, (B) indel background model, and (C) CBS-specific background model.

To identify positive selection in cancer genomes, it is essential to build an accurate background mutation rate model that corrects for covariates (features) that impact regional mutation rate variation, such as local sequence context and chromatin profiles. A range of genetic and epigenetic features that could be correlated with GC somatic mutation rates were considered. The features included 33 general and 36 gastric-specific chromatin features, 133 transcription factor binding profiles, and DNA replication timing profiles. To model the effect of local sequence context on mutation rate, previous studies have considered the single or tri-nucleotide sequence context of each mutation. However, as mutation rates may also be influenced by wider sequence contexts, an expanded sequence context model that considers the effects of tri-nucleotide (1 bp flanks) and penta-nucleotide (2 bp flanks) contexts on the mutation probability of each base was thus used. LASSO logistic regression was used to identify the most predictive epigenetic and sequence context features (FIG. 9). These features were used to estimate sample-specific background mutation probabilities, and to identify individual focal regions (21 bp) exhibiting mutational recurrence across samples beyond chance expectation (FIG. 2A; Methods). Overlapping significantly mutated regions were merged to obtain a list of unique hotspots.

Recurrent Indels in Gastric Lineage-Specific Genes

Figure 2B:
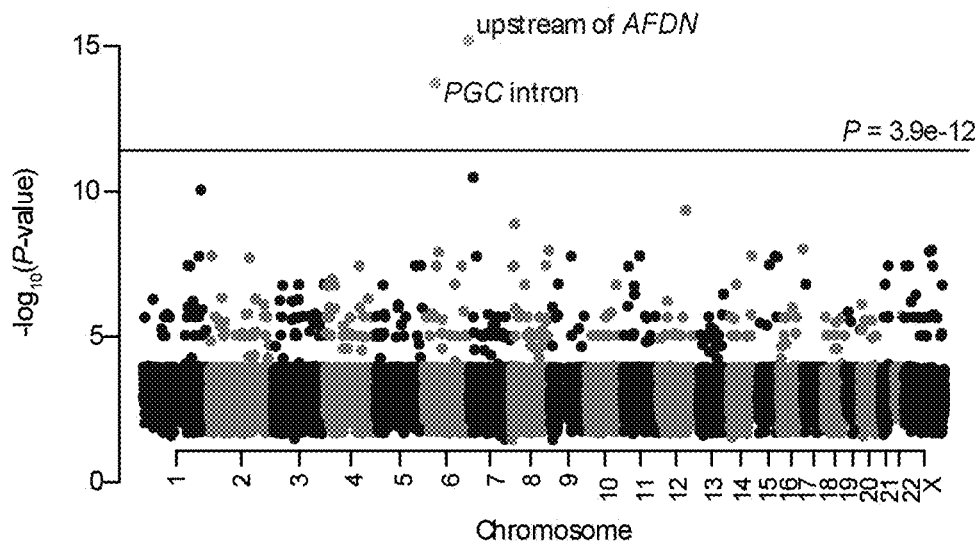
Figure 2C:
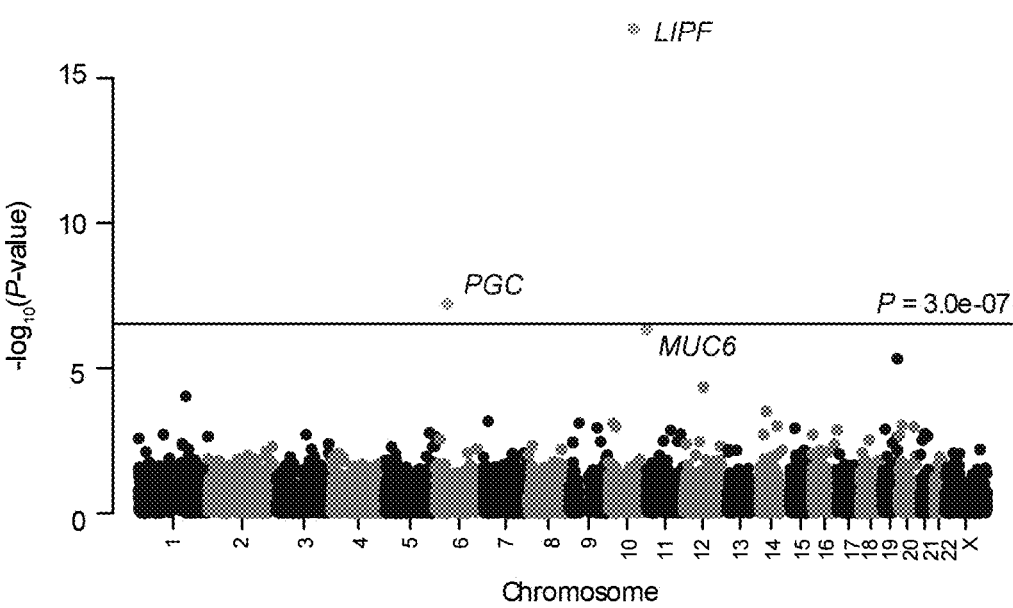
Figures 2D, 2E, 2F:
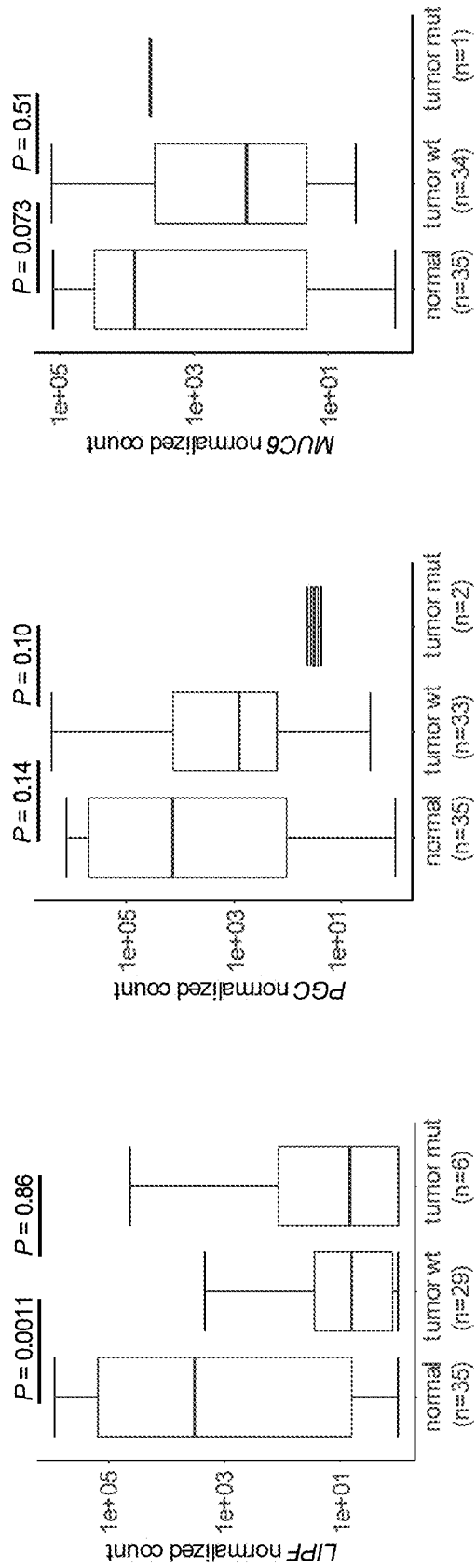
Figure 3A:
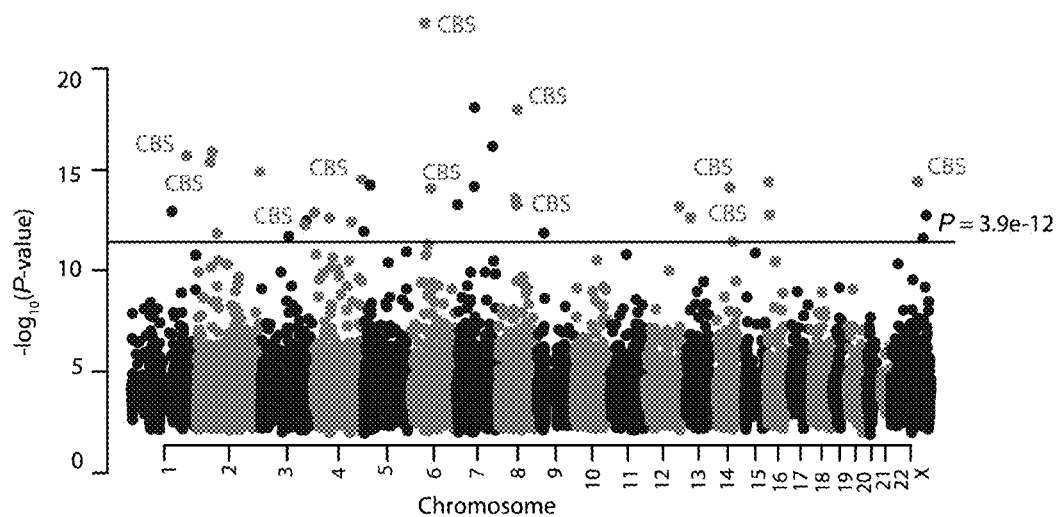
FIG. 3 shows the genome-wide analysis of non-coding SNV hotspots. (A) The negative log P-values of SNV recurrence for all 21 bp regions genome-wide, only regions with at least 3 mutations are displayed. Significantly mutated hotspots overlapping CBSs are highlighted. The horizontal line marks the Bonferroni adjusted P-value of 0.01. (B) Log odds ratio of the enrichment of hotspot mutations and non-hotspot mutations in transcription factor binding regions and conserved regions. Error bars indicate the s.e.m of the log odds ratio. (C) Gastric cancer samples sorted by molecular subtype, with each row representing a significant mutation hotspot. Mutated samples are highlighted in black in the matrix. The mutation load of each sample is shown in the bottom panel. The right panel annotates the location of each hotspot with respect to annotated functional regions.

This statistical framework was used to identify somatic mutation hotspots (both indels and point mutations) across the non-coding genome (FIG. 2B and FIG. 3A). The top indel hotspot was located ~100 kbp upstream of the AFDN gene, which is frequently translocated in leukemia and down-regulated in multiple cancer types. The effect of hotspot mutations on AFDN expression could not be tested, as there was a lack of paired tumor expression data for the mutated samples. The second most significant indel hotspot was located in an intron of the PGC gene, which encodes the precursor of gastric proteinase pepsinogen (see Table 4 below). PGC is expressed at 11940 TPM in the stomach, 39 TPM in the lung, and <=2 TPM in all other tissues in GTEx. Interestingly, a recent study reported that LIPF, a lineage-specific gastric lipase, has broad enrichment of indels in gastric cancer. Hypothesizing that other lineage-specific genes could show similar patterns of indel enrichment, a gene-based recurrence analysis was performed to identify all genes with broad enrichment of indels in their non-coding regions (combining promoter, untranslated, and intronic regions for each gene; Methods). Interestingly, the top 3 genes in this analysis were all lineage-specific genes highly expressed in stomach tissue: LIPF, PGC and MUC6 (FIG. 2C; Table 5 below). MUC6 encodes a mucin glycoprotein that is a major constituent of the gut mucosa, and is expressed at 133 TPM in stomach tissue, 38 TPM in the pancreas, and <=2 TPM in all other tissues in GTEx. However, consistent with a previous report, non-coding indels in these 3 recurrently mutated lineage-specific genes were not associated with expression change (FIG. 2D-F).

TABLE 4

Indel hotspots. Significantly mutated non-coding indel hotspots identified by a genome-wide scan of 21 -bp windows.

| Chr | Start | End | P-value | Length | # mutated samples | adjusted P-value |
| --- | --- | --- | --- | --- | --- | --- |
| chr6 | 168136120 | 168136140 | 6.45E−16 | 21 | 4 | 1.63E−06 |
| chr6 | 41709379 | 41709409 | 1.93E−14 | 31 | 4 | 4.90E−05 |

TABLE 5

Genes enriched for non-coding indels.

| Gene Name | Chr | Gene Start | Gene End | Gene Length | # mutated samples | P-value | Adjusted P-value |
| --- | --- | --- | --- | --- | --- | --- | --- |
| LIPF | chr10 | 90424198 | 90438571 | 14807 | 16 | 1.89E−17 | 6.39E−13 |
| PGC | chr6 | 41704449 | 41721847 | 16717 | 7 | 6.17E−08 | 2.08E−03 |
| MUC6 | chr11 | 1012821 | 1036706 | 17851 | 8 | 4.92E−07 | 1.66E−02 |

Mutation Hotspots Enriched at CBSs in Gastric Cancer

Figure 3B:
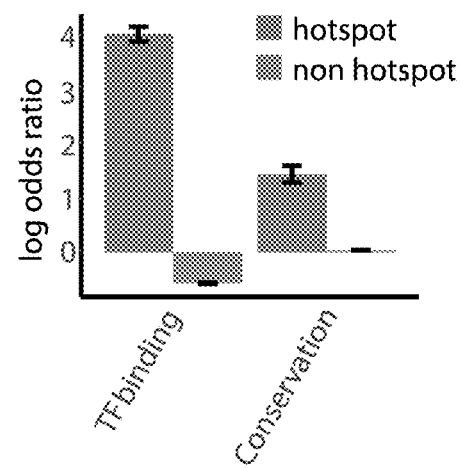
Figure 3C:
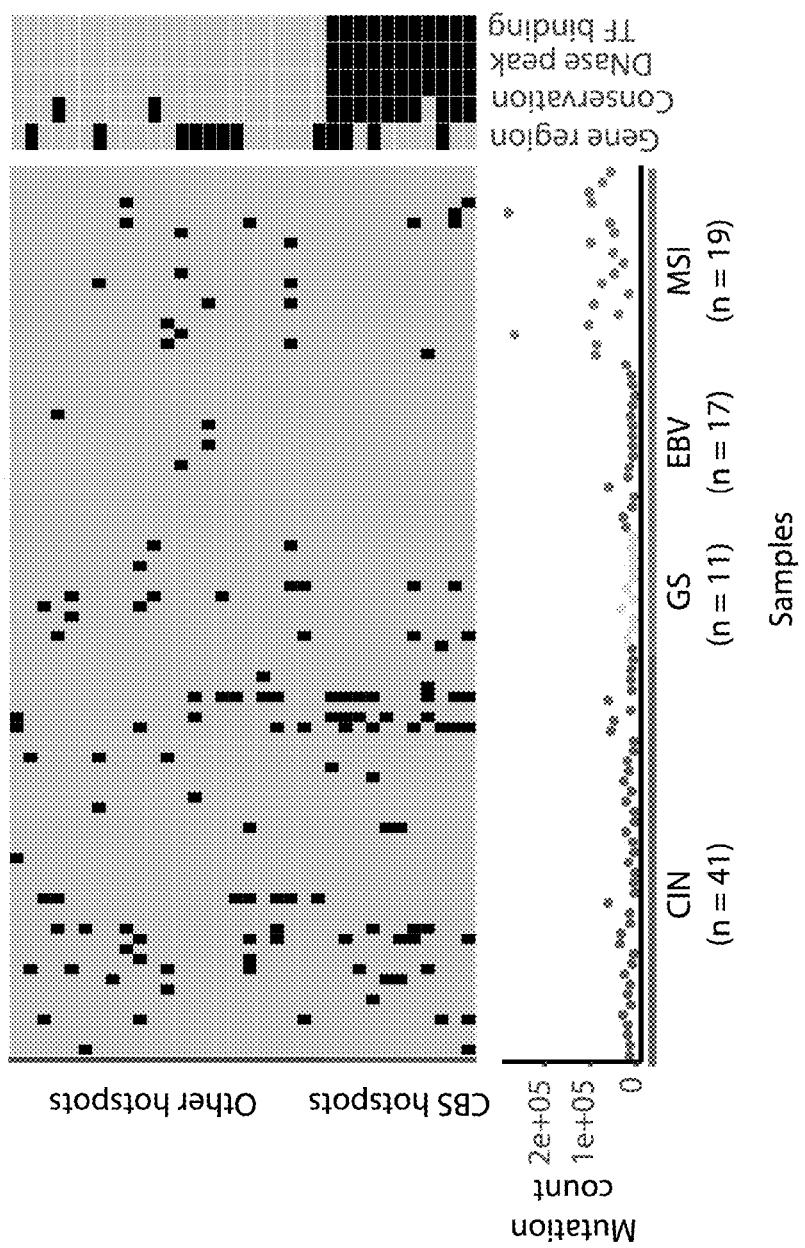
Figure 10:
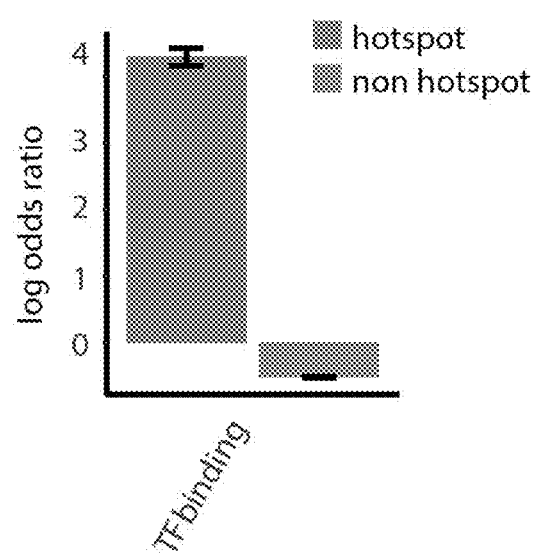
FIG. 10 shows the log odds ratio of the enrichment of hotspot mutations and non-hotspot mutations in constitutive transcription factor binding regions. Error bars indicate the s.e.m of the log odds ratio.

A genome-wide analysis of SNVs in non-coding regions was then performed and 34 significant mutation hotspots were identified (Bonferroni adjusted P-value <0.01; FIG. 3A; Table 6 below). These hotspots were enriched in conserved sequences and TF binding regions, suggesting that many hotspot mutations may disrupt functional elements (FIG. 3B). Strikingly, of the 34 mutation hotspots, 11 were located in CBSs (FIGS. 3A and 3C). The majority of mutations at CBS hotspots occurred in CIN tumors (71%, P=0.012 by two-sided Fisher's Exact test), which is the most common gastric cancer subtype, accounting for ~50% of all GC cases (FIG. 3C). The remaining 23 non-CBS hotspots often overlapped gene regions, but never co-located with TF binding regions. Furthermore, a depletion of somatic mutations at gastric-specific TFBSs was observed among the non-hotspot mutations (FIG. 3B). Overall, gastric tissue TFBSs comprises about 1% of the genome, but only 0.58% of the non-hotspot mutations were located in these regions. A similar depletion of mutations was observed for constitutive TFBSs (FIG. 10). This is striking, as two recent studies have found that somatic mutation rates are elevated at transcription factor binding sites (TFBSs), and that this higher overall mutation load at TFBSs may be explained by reduced accessibility to nucleotide-excision repair (NER) enzymes at these sites. This phenomenon is primarily observed in melanoma and lung adenocarcinoma where NER plays an important role in repairing carcinogen induced DNA lesions. In contrast, the present finding demonstrates that NER and TF occupancy is not a cause of regional mutational bias in GC.

Figure 11:
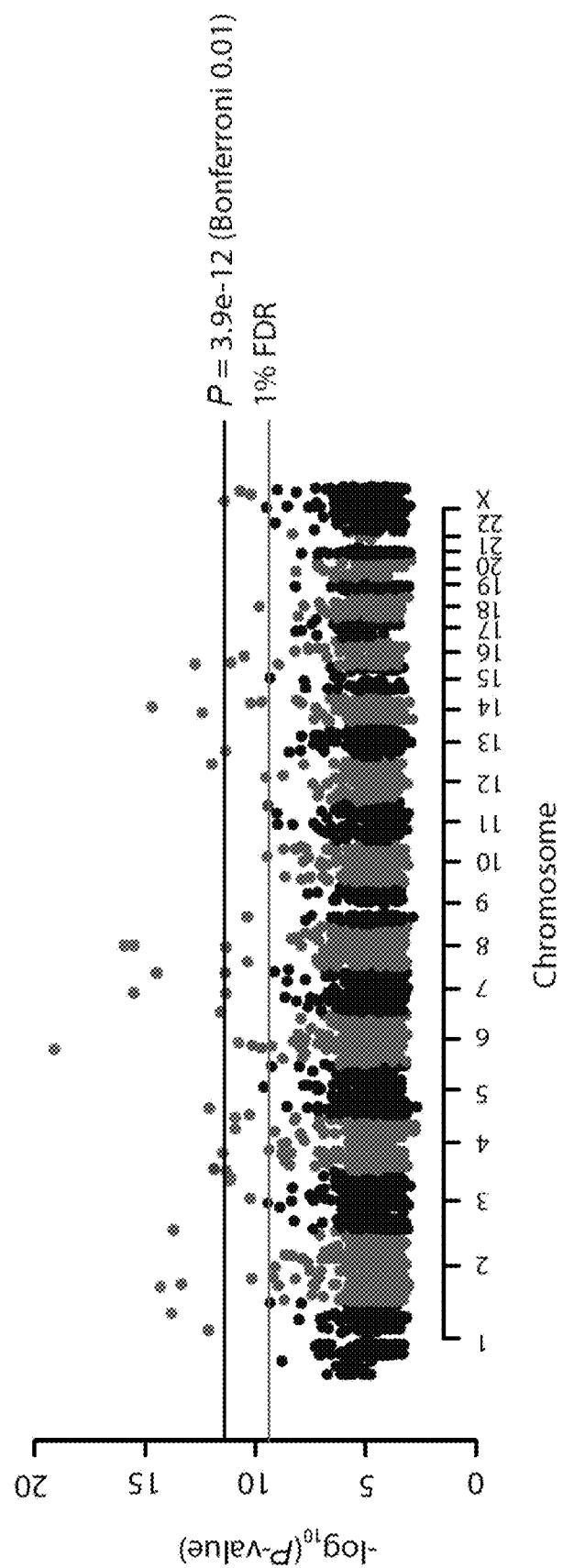
FIG. 11 is a mutation hotspot analysis using 41 bp windows. The negative log P-values of SNV recurrence for all 41 bp regions genome-wide, with only regions with at least 3 mutations are displayed. 17/34 hotspots remained significant and only 2 additional hotspots were identified.

To test if the 21 bp window size was adequate to capture most mutation hotspots, the hotspot analysis was repeated using larger 41 bp windows. In general, the rankings of the hotspots remained stable (FIG. 11). 17/34 hotspots remained significant and only 2 additional hotspots were identified (P<0.01, Bonferroni correction).

was 7.1 and 4.7-fold higher at CBSs compared to flanking regions in CIN and GS tumors, respectively (FIG. 4A-E). There was no enrichment of somatic mutations at CBSs in MSI tumors, likely due to impaired DNA mismatch repair. Surprisingly, EBV tumors, which are not MMR-deficient, only had a modest 1.7-fold increase in mutation load at CBSs. The enrichment of somatic mutations at CBSs is therefore unlikely the result of differential DNA repair alone.

Consistent with another finding in colorectal cancer, the inventors found that somatic mutations at CTCF motifs, including the CBS hotspot mutations, were predominately A.T>C.G and A.T>G.C substitutions (FIG. 4F), suggesting that hotspot mutations are generated by the same mutational process as other CBS mutations. The mutation pattern at CBS hotspots was overall similar to that of all CBSs. However, while a conserved base at position 9 of the 19 bp CTCF binding motif was the most commonly mutated position at CBSs in general, the CBS hotspot mutations had the highest enrichment in the 4 bp sequence flanking the 5'

TABLE 6

SNV hotspots. Significantly mutated non-coding SNV hotspots identified by a genome-wide scan of 21-bp windows.

| Chr | Start | End | P-value | Length | # mutated samples | Adjusted P-value | Annotation |
|---|---|---|---|---|---|---|---|
| chr6 | 50570094 | 50570120 | 5.40E−23 | 27 | 11 | 1.37E−13 | CBS |
| chr7 | 68391104 | 68391132 | 8.36E−19 | 29 | 9 | 2.12E−09 | intergenic |
| chr8 | 71000992 | 71001012 | 1.09E−18 | 21 | 8 | 2.75E−09 | CBS |
| chr7 | 136495924 | 136495948 | 6.73E−17 | 25 | 9 | 1.71E−07 | intergenic |
| chr2 | 57627616 | 57627640 | 1.32E−18 | 25 | 8 | 3.34E−07 | intergenic |
| chr1 | 209422184 | 209422222 | 1.94E−16 | 39 | 7 | 4.90E−07 | CBS |
| chr2 | 49173770 | 49173816 | 4.05E−16 | 47 | 9 | 1.03E−06 | CBS |
| chr2 | 239033350 | 239033370 | 1.32E−15 | 21 | 6 | 3.35E−06 | ESPNL intron |
| chr4 | 182064578 | 182064613 | 3.09E−15 | 36 | 7 | 7.83E−06 | CBS |
| chrX | 104435106 | 104435140 | 4.26E−15 | 35 | 7 | 1.08E−05 | CBS |
| chr16 | 8381278 | 8381302 | 4.44E−15 | 25 | 6 | 1.13E−05 | intergenic |
| chr5 | 23824204 | 23824224 | 6.27E−15 | 21 | 8 | 1.59E−05 | intergenic |
| chr7 | 67614923 | 67614943 | 7.42E−15 | 21 | 8 | 1.88E−05 | intergenic |
| chr14 | 70285576 | 70285601 | 8.40E−15 | 26 | 6 | 2.13E−05 | CBS |
| chr6 | 73122084 | 73122123 | 9.16E−15 | 40 | 7 | 2.32E−05 | CBS |
| chr8 | 65161396 | 65161420 | 2.79E−14 | 25 | 7 | 7.08E−05 | intergenic |
| chr7 | 4937707 | 4937736 | 5.80E−14 | 30 | 6 | 1.47E−04 | intergenic |
| chr8 | 70576141 | 70576184 | 6.12E−14 | 44 | 8 | 1.55E−04 | CBS |
| chr12 | 126996666 | 126996686 | 7.21E−14 | 21 | 7 | 1.83E−04 | intergenic |
| chr1 | 153607104 | 153607124 | 1.24E−13 | 21 | 5 | 3.13E−04 | CHTOP intron |
| chr4 | 5415060 | 5415082 | 1.39E−13 | 23 | 6 | 3.52E−04 | STK32B intron |
| chr16 | 13516145 | 13516165 | 1.87E−13 | 21 | 6 | 4.73E−04 | intergenic |
| chrX | 137405623 | 137405655 | 1.93E−13 | 33 | 7 | 4.88E−04 | intergenic |
| chr13 | 36552821 | 36552860 | 2.57E−13 | 40 | 8 | 6.51E−04 | CBS |
| chr4 | 62653076 | 62653096 | 2.68E−13 | 21 | 6 | 6.80E−04 | LPHN3 intron |
| chr3 | 171164993 | 171165017 | 3.61E−13 | 25 | 5 | 9.15E−04 | TNIK intron |
| chr4 | 144748744 | 144748764 | 4.17E−13 | 21 | 6 | 1.06E−03 | intergenic |
| chr3 | 164903700 | 164903728 | 5.72E−13 | 29 | 7 | 1.45E−03 | CBS |
| chr5 | 1472143 | 1472163 | 1.21E−12 | 21 | 5 | 3.07E−03 | LPCAT1 intron |
| chr9 | 25481736 | 25481758 | 1.44E−12 | 23 | 7 | 3.66E−03 | intergenic |
| chr2 | 77150455 | 77150477 | 1.53E−12 | 23 | 6 | 3.88E−03 | LRRTM4 intron |
| chr3 | 104801455 | 104801477 | 2.12E−12 | 23 | 6 | 5.38E−03 | intergenic |
| chrX | 125548690 | 125548710 | 2.50E−12 | 21 | 6 | 6.33E−03 | intergenic |
| chr14 | 83046706 | 83046744 | 3.82E−12 | 39 | 7 | 9.67E−03 | intergenic |

Differential CBS Mutation Load Across Gastric Cancer Subtypes

Despite the general depletion of somatic mutations at TFBSs in gastrointestinal tumors, several studies have reported an increased mutation rate specifically at CBSs in gastrointestinal tumors. Indeed, when all CBS across the genome were examined, a 3-fold increased mutation rate at CBSs (11 mutations/Mb) was found compared to their 1 Kb flanking regions (3.6 mutations/Mb). Additionally, the mutation frequencies at CBSs were very different among tumors of different molecular subtypes. The somatic mutation rate end of the CTCF motif. Furthermore, C>T changes, which are relatively common among all CBS mutations are much rarer among the CBS hotspot mutations (Fisher's exact test P-value=$4.4 \times 10^{-07}$. These differences could indicate a functional difference between CBS hotspot and non-hotspot mutations.

Hotspots Remain Significant with a CBS-Specific Model

To explicitly test if the CBS hotspots could be explained by the genome-wide elevated mutation rate at CBSs, a CBS-specific background mutation model was constructed. Since CBS mutation rates varied across tumor subtypes, this model further included the tumor subtype as a covariate. Also, since CBSs located at chromatin loop boundaries have higher somatic mutation burden than non-boundary CBSs, the CBS-specific background model differentiated between CBSs inside and outside chromatin loop boundaries. CTCF loop domains have not been profiled in gastric tissue but tend to be cell-type invariant. A constitutive set of CTCF domains shared across 3 cell lines (CM12878, Jurkat and K562) was therefore used to define CTCF loop boundaries. In addition, since the mutation spectrum at CBSs is distinct from the overall genomic mutation spectrum, LASSO logistic regression was performed to identify sequence context features correlated with the somatic mutation rate at CBSs. To identify other mutational processes that might be associated with the occurrence of CBS mutations, the correlation between the proportion of CBS mutations in each tumor and the percentage contribution of each COSMIC mutation signature to each tumor was calculated. While CBS mutations are known to be positively associated with signature 17, it was found that CBS mutations were also strongly negatively associated with COSMIC mutation signature 1, an age related signature (Pearson correlation=−0.41, FIG. 12). Therefore, the percentage contributions of mutation signatures 1 and 17 in each individual were added as covariates. Finally, this model also corrected for replication timing and local mutation rate. With this model, 9/11 CBS hotspots remained significant at the Bonferroni corrected significance threshold of 0.01 and the other 2 were borderline with adjusted P-values of 0.025 and 0.086 (FIG. 4G). Furthermore, 7 additional CBSs became significant with the restricted hypothesis testing (Table 7 below; FIG. 13-14). Mutations at these specific sites can therefore not be explained by a genome-wide elevated mutation rate at CBS, indicating that mutations at these focal sites are may be positively selected in gastric tumors.

Hi-C data from IMR90 cells published by Dixon et al. was used to examine the 3D chromatin structure around each hotspot (FIG. 15-17). The flanking TAD boundary nearest to each hotspot was identified, and the association between the mutation status of each hotspot and the expression of genes within the two adjacent TADs was tested. Genes with nominally altered expression were found for 3 of the four hotspots (FIG. 5), and two of them remain significant after correcting for multiple testing in each region.

Figures 5A, 5B, 5C:
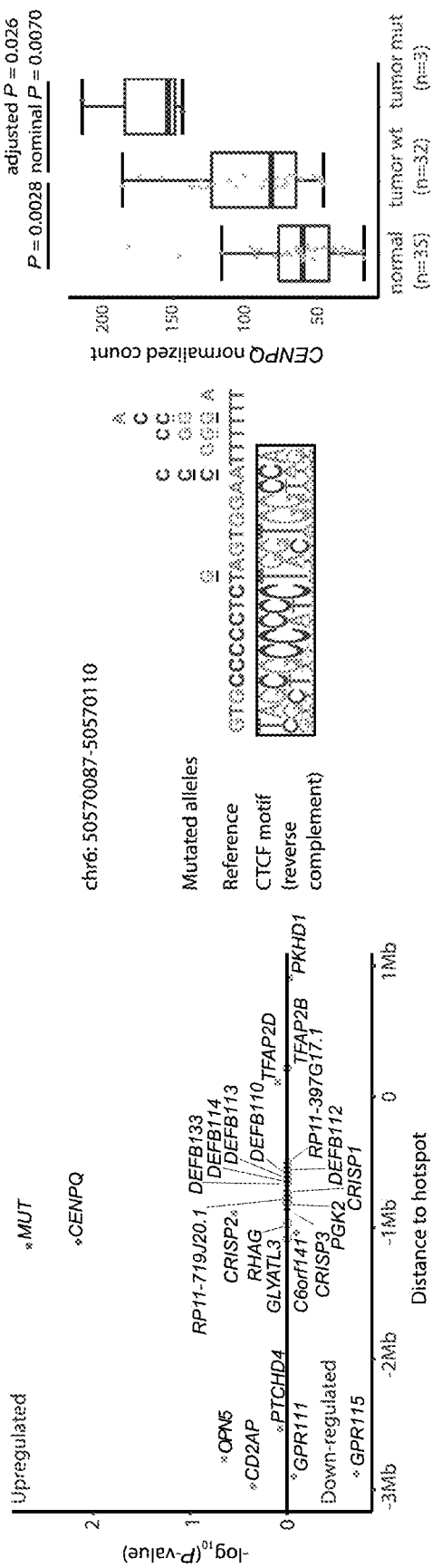
FIG. 5 shows the association of CBS hotspot mutations and cis-gene expression. (A, D, G) Association between mutation status of the CBS hotspot and expression levels of neighboring genes (two-sided Wilcoxon rank-sum test). Upregulated genes are shown above the x-axis, and down-regulated genes are shown below the x-axis. Non-expressed genes are shown with empty circles on the x-axis (normalized count<10 in all samples). (B,E,H) The reference sequence and mutated alleles at the 3 CBS hotspots (SEQ ID NO: 93, SEQ ID NO: 94, SEQ ID NO: 95, respectively). The mutations in tumors with expression data are underlined (black underline: TCGA tumors, grey underline: SG tumors). (C, F, I) The gene expression of CENPQ (C), KCNQ5 (F) and SPG20 (I) in normal gastric tissue, and tumors with and without mutations at the corresponding CBS hotspot. P-values were adjusted using the Benjamini-Hochberg method.
Figures 18A, 18B, 18C:
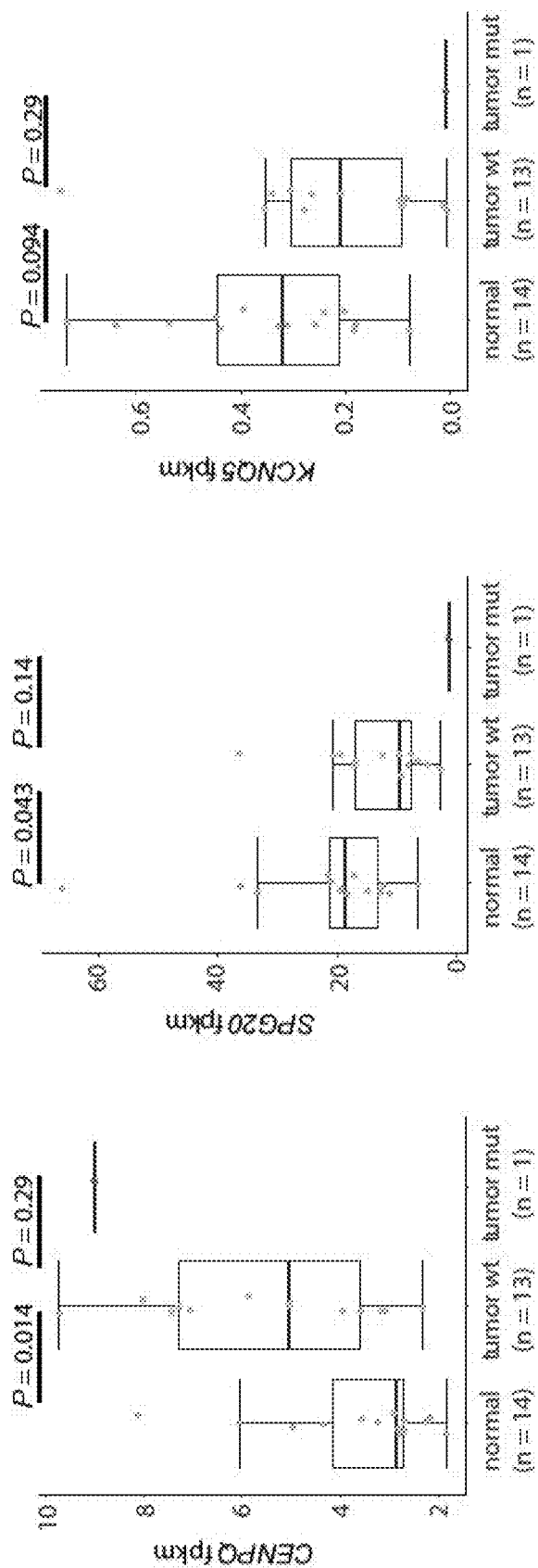

The first hotspot that was identified is located in a CBS on chromosome 6 and has mutations in 12 samples (FIG. 5A-C). The expression of two neighboring genes, CENPQ and MUT, ~1 Mb upstream of this hotspot was significantly elevated in the mutated samples (P=0.007 and 0.0021 respectively, adjusted P=0.026 and 0.042 respectively, two-sided Wilcoxon rank-sum test; FIG. 5A-C). A similar trend of CENPQ expression was observed using the expression data from the SG cohort (FIG. 18A). CENPQ is a subunit of a centromeric complex, and is involved in mitotic progression and chromosomal segregation. Interestingly, the tumor with the highest expression of CENPQ was mutated at the highly conserved position 9 of the CTCF motif, while the other two tumors were mutated at position 2 of the CTCF motif. This indicates that different mutations in the same hotspot may have different disruptive potentials. However, a formal evaluation of such effects requires a larger set of tumor samples with both CBS mutations and RNA-seq data available.

Figures 5D, 5E, 5F:
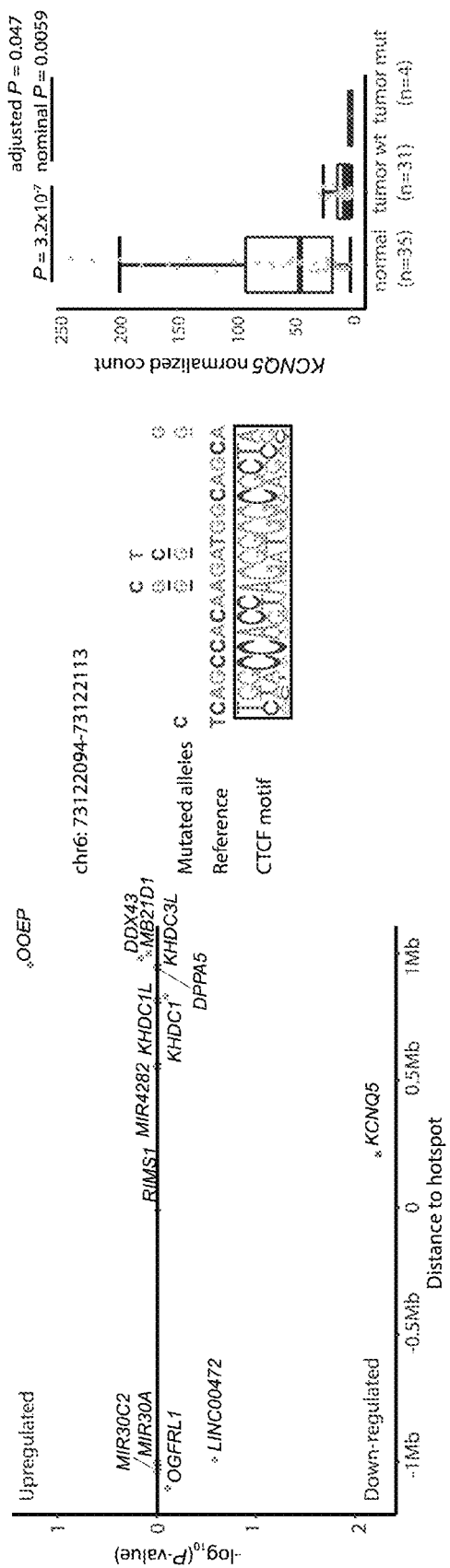

The next hotspot that was tested is located on chromosome 6 with 9 mutated samples. Tumors with mutations at this hotspot had significantly lower expression of the KCNQ5 gene (Wilcoxon P=0.0059, adjusted P=0.047), located ~200 kb downstream of the hotspot (FIG. 5D-F). A similar trend in KCNQ5 expression was observed using the expression data from the SG cohort (FIG. 18B). A recent

TABLE 7

Recurrently mutated CBSs under the CBS-specific background model

| Chr | Start | End | P-value | Length | # mutated samples | Adjusted P-value |
|---|---|---|---|---|---|---|
| chr6 | 50570082 | 50570110 | 1.32E−14 | 29 | 11 | 6.28E−10 |
| chr8 | 70576149 | 70576177 | 2 31E−14 | 29 | 8 | 1.10E−09 |
| chr8 | 71000975 | 71001003 | 8.65E−14 | 29 | 8 | 4.10E−09 |
| chr14 | 70285585 | 70285613 | 4.75E−13 | 29 | 7 | 2.26E−08 |
| chr6 | 50570080 | 50570108 | 1.22E−12 | 29 | 10 | 5.78E−08 |
| chr2 | 49173785 | 49173813 | 4.48E−11 | 29 | 8 | 2.13E−06 |
| chrX | 104435103 | 104435131 | 3.21E−10 | 29 | 7 | 1.52E−05 |
| chr3 | 164903684 | 164903712 | 4.98E−10 | 29 | 7 | 2.37E−05 |
| chr3 | 115533804 | 115533832 | 2.22E−09 | 29 | 5 | 1.05E−04 |
| chr4 | 10556425 | 10556453 | 5.78E−09 | 29 | 6 | 2.74E−04 |
| chr12 | 88242203 | 88242231 | 4.01E−08 | 29 | 5 | 1.90E−03 |
| chr7 | 137139122 | 137139150 | 4.59E−08 | 29 | 6 | 2.18E−03 |
| chr10 | 108384789 | 108384817 | 4.97E−08 | 29 | 5 | 2.36E−03 |
| chr1 | 209422187 | 209422215 | 6.00E−08 | 29 | 7 | 2.85E−03 |
| chr6 | 73122090 | 73122118 | 6.92E−08 | 29 | 7 | 3.28E−03 |
| chr10 | 81134496 | 81134524 | 1.15E−07 | 29 | 4 | 5.45E−03 |
| chr11 | 123349284 | 123349312 | 1.80E−07 | 29 | 5 | 8.56E−03 |

CBS Hotspot Mutations Associated with Gene Expression Changes

The possibility that the CBS hotspots were associated with changes in expression of nearby genes was next examined. Analysis was restricted to the 4 CBS hotspots that had at least 3 mutated samples with gene expression data in the TCGA cohort (N=35 samples). The results were validated using expression data from the SG cohort (N=14 samples). Since the chromatin structure is generally cell-type invariant and there is no published Hi-C data from gastric tissue, the study by Umer et al. found the same mutation hotspot by analyzing motif-breaking mutations. Using an electrophoretic mobility shift assay, Umer et al. confirmed that the chr6:73,122,103A>G mutation disrupts CTCF binding. In addition, it has been reported that CTCF is involved in the spatial organization of the KCNQ5 locus, and knock-down of CTCF down-regulates KCNQ5 expression.

Figures 5G, 5H, 5I:
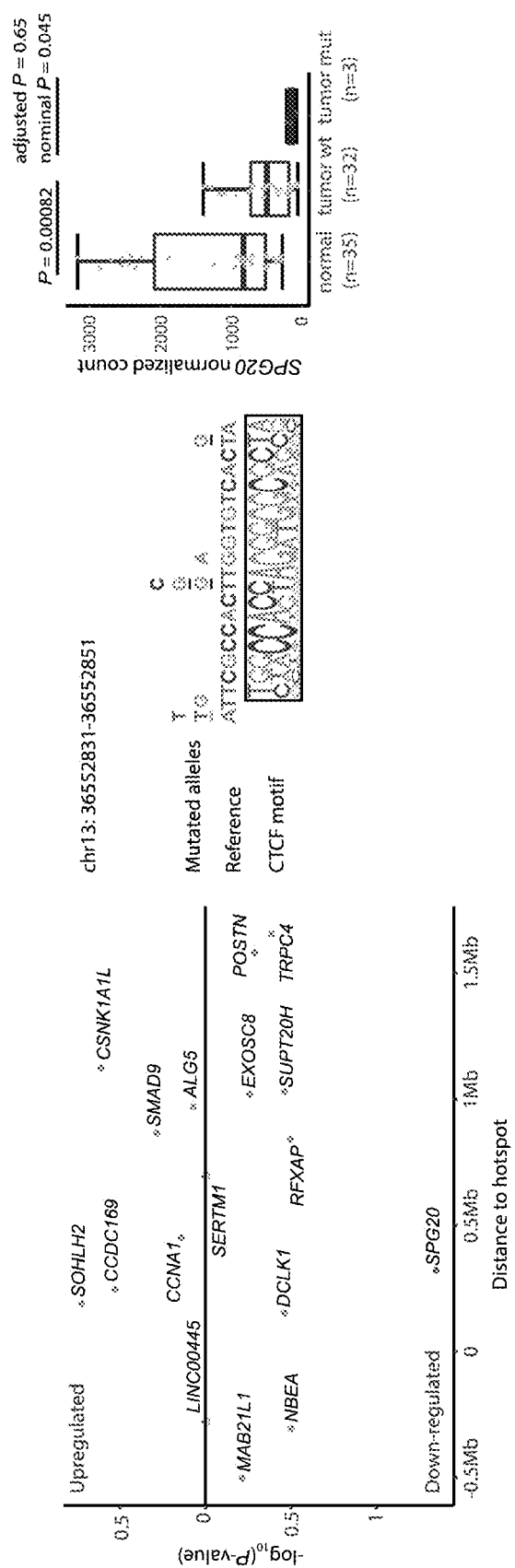

At the third hotspot located on chromosome 13, mutated tumors had on average a 3-fold decrease in SPG20 expression (Wilcoxon P=0.045, adjusted P=0.65; FIG. 5G-I).

However, only 3 tumors with expression data were mutated at this hotspot, and the expression change was not significant after correcting for multiple testing. A larger sample size is needed to evaluate if this is a spurious or true correlation. A similar trend in SPG20 expression is observed using the expression data from the SG cohort (FIG. 18C). SPG20 is involved in epidermal growth factor receptor trafficking and was previously found to be significantly mutated in the exome of esophageal cancer.

In all 3 cases, it was confirmed that the expression changes of these genes were significant after correcting for variation in DNA copy numbers and tumor purity between samples (FIG. 19). As CBSs are essential in maintaining the chromosomal architecture, it is likely that these CBS hotspot mutations cause altered expression of nearby cancer driver genes by disrupting the local chromosomal organization. Indeed, using the set of constitutive CTCF-CTCF loops, chromatin contacts between the KCNQ5 and SPG20 loci and their corresponding CBS hotspots were observed (FIG. 16-17). Interestingly, the 3 genes were also differentially expressed in GC tumors compared to normal gastric tissue. CENPQ expression was up-regulated in tumors (Wilcoxon P=0.0028; FIG. 5C), while both KCNQ5 and SPG20 expression was down-regulated in tumors compared to normal gastric samples (Wilcoxon P=$3.2 \times 10^{-7}$ and 0.00082 respectively; FIGS. 5F and 5I). Therefore, it is plausible that the expression of these 3 genes could be altered in GC through additional mechanisms. Indeed, KCNQ5 and SPG20 were found to be down-regulated in colorectal cancer compared to the normal mucosa due to promoter hypermethylation. These results further support the contributions of these genes to GC tumorigenesis.

Figures 4A, 4B, 4C, 4D:
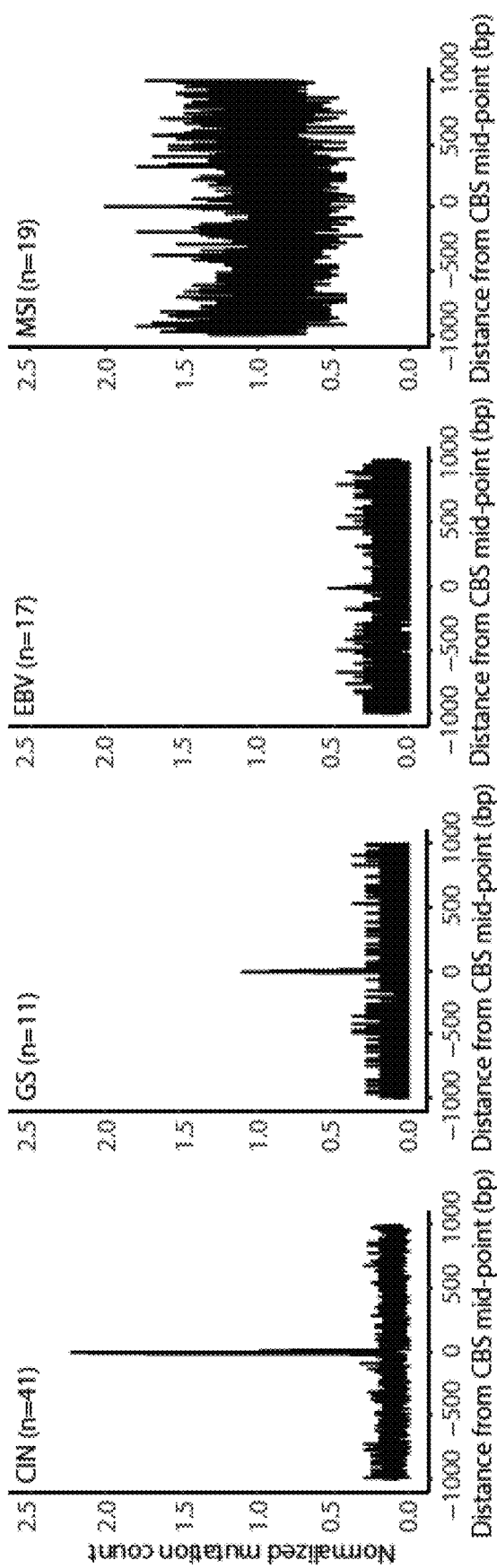
FIG. 4 is an analysis of CBS mutations in different gastric cancer subtypes. (A-D) Mutation count per tumor around CBSs in the four gastric cancer subtypes. (E) Elevated mutation rates at CBSs compared to flanking regions. (F) Somatic substitution patterns within CTCF motifs for hotspot mutations and all mutations, respectively. (G) The negative log P-values of mutation recurrence of all CBSs evaluated with a CBS-specific background model. CBS hotspots identified in FIG. 3A are highlighted and labeled. The horizontal line marks the Bonferroni adjusted P-value of 0.01.
Figure 4E:
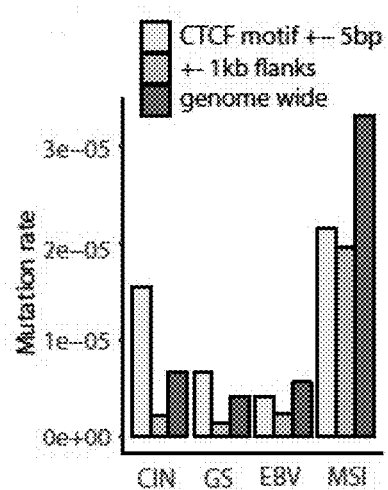
Figure 4F:
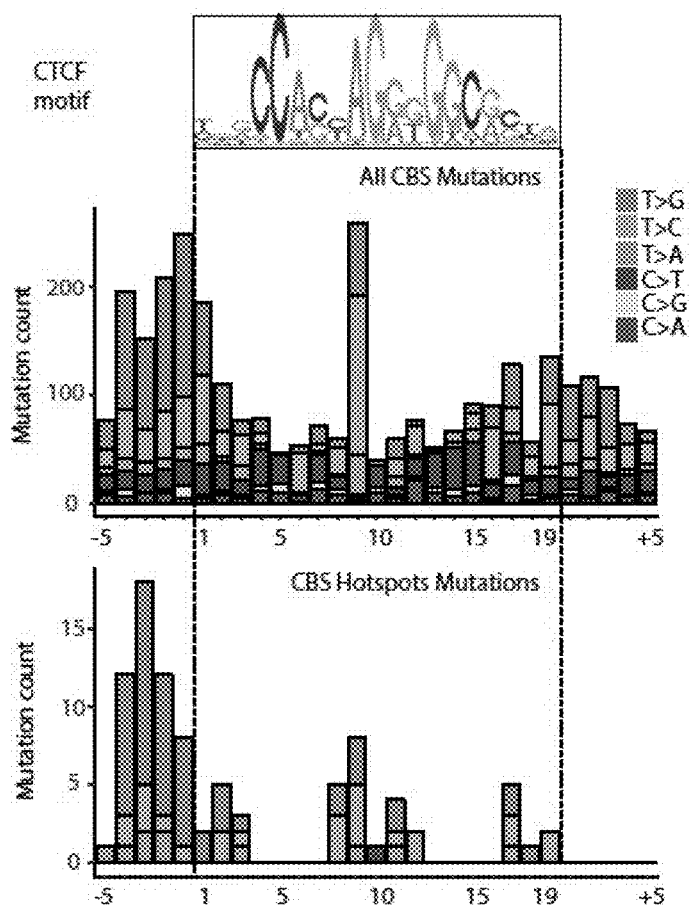
Figure 4G:
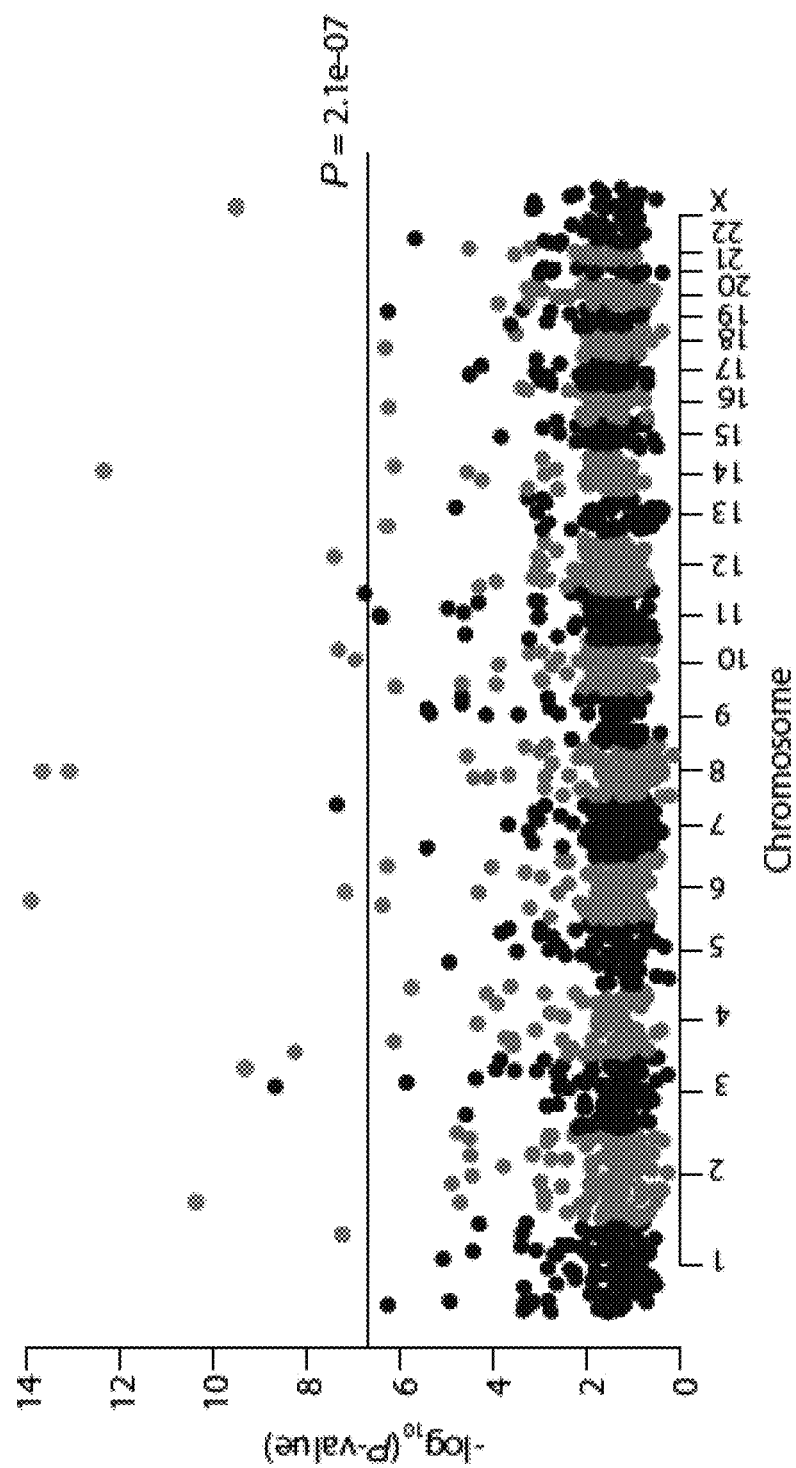
Figure 20A:
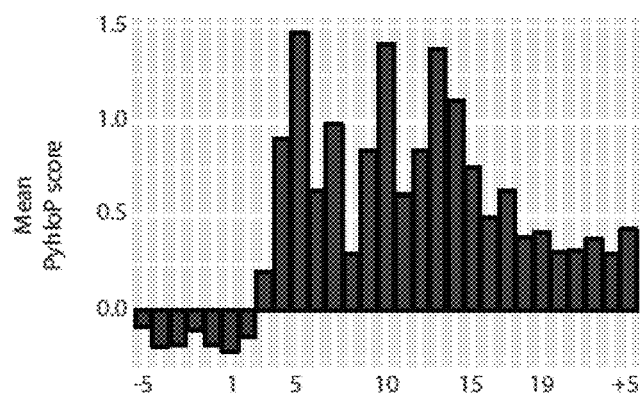
Figure 20B:
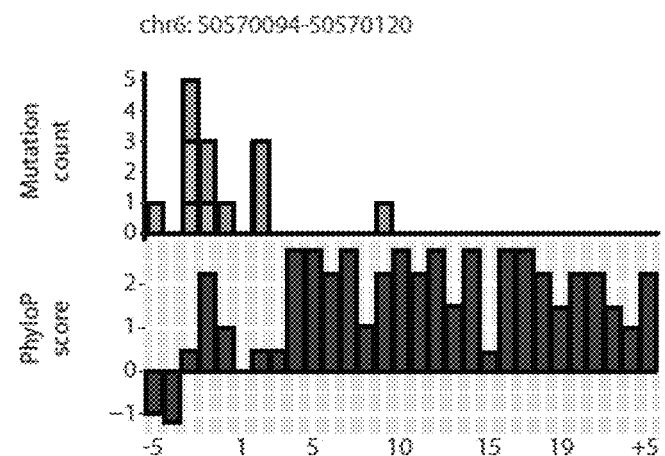
Figure 20C:
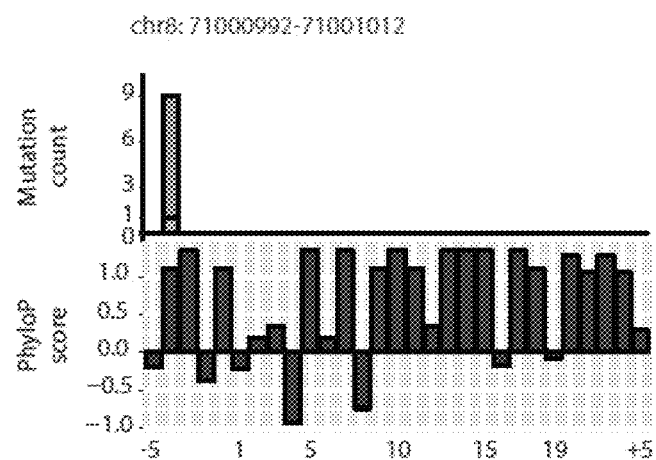

Many of the hotspot mutations were located in the 5' flanks of the consensus CTCF motif (FIG. 4F). Previous studies have found increased conservation of the flanking sequences of weaker CTCF and REST binding sites, suggesting that the sequence context is important for TF binding at these sites. The evolutionary conservation at the CTCF binding motifs and their flanking sequences was examined. In general, the 5' flanks of the CTCF motifs are not conserved (FIG. 20A). However, in the hotspot upstream of CENPQ, the mutation cluster in the 5' flank co-occurred with conserved bases (FIG. 20B). In addition, another CBS hotspot with 9 5'-flank mutations that coincided with a highly conserved base was found (FIG. 20C). Such hotspot mutations, affecting conserved 5' flanks of CTCF motifs, could disrupt context-specific binding of CTCF.

The possibility that mutations in the flanking regions of CTCF motifs create or disrupt binding motifs of other TFs was also examined. DeepBind[55] was used to predict the binding scores of wildtype and mutated sequences for 472 transcription factors. However, mutations with predicted change in TF binding were found only at three CBS sites (Table 8 below). Lastly, it is also possible that some mutations at CBS flanks are passenger mutations arising due to the overall elevated mutation rates at CBSs. While the present model identifies individual CBS regions with overall mutation enrichment, it does not allow one to distinguish between passenger and driver mutations within such regions.

TABLE 8

DeepBind analysis on hotspot mutations flanking CTCF-binding motifs

| Hotspot Location | Mutation | Sample ID | Motif creation | Motif disruption |
|---|---|---|---|---|
| chr2: 49173777-49173807 | chr2:49173789 T > G | apollo10 | ATF2 | — |
| chr2: 49173777-49173807 | chr2:49173789 T > G | HK-pfg146 | ATF2 | — |
| chr2: 49173777-49173807 | chr2:491737n T > G | tan980437 | ATF2 | — |
| chr13: 38882830-3858285e | chr13 36552831 A > T | HK-pfg054 | RCOR1 | — |
| chr13: 38552830-38882850 | chr13: 36552831 A > T | tan76629543 | RCOR1 | — |
| chr14: 70285579-70285801 | chr14: 70285588 T > G | HK-pfg092 | — | SIN3A |
| chr14: 70285576-70285601 | chr14: 70285588 T > G | HK-p344 | — | SIN5A |
| chr14: 702.88878-70285801 | chr14: 70285588 T > G | TCGA-D7-6528 | — | SIN3A |

CBS Hotspots are Often Mutated in Gastrointestinal Cancers

Figures 6A, 6B, 6C:
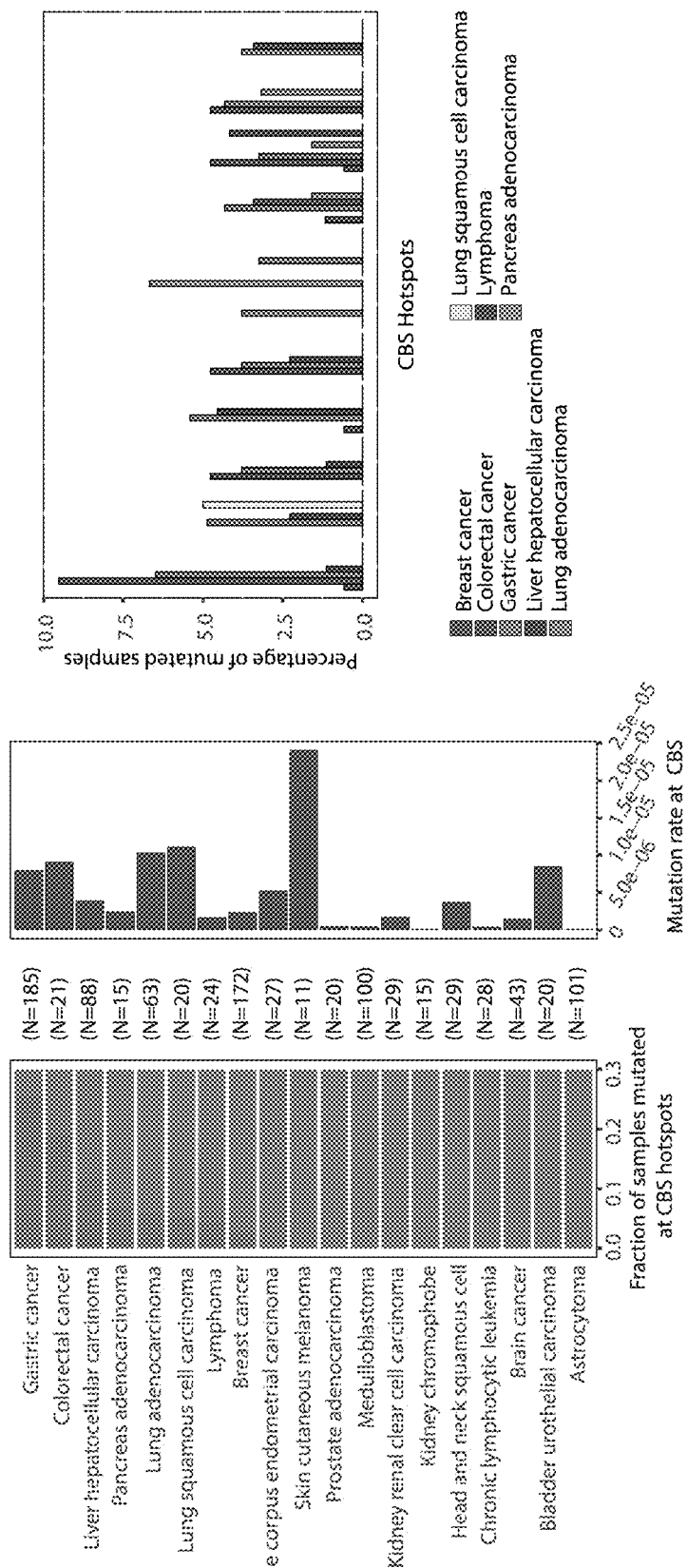
FIG. 6 shows the pan-cancer analysis of mutation recurrence at the 11 CBS mutation hotspots. (A) Fraction of samples with mutation in at least one of the CBS hotspots in different cancer types. (B) Mutation rate of CBSs in different cancer types. (C) Mutation recurrence of individual CBS hotspots in different cancer types.

Taken collectively, 25% of all gastric tumors are mutated in at least one of the 11 CBS hotspots, representing the second most mutated functional region in gastric cancer after TP53 (50% of gastric tumors). To study if these hotspots could also play a role in other cancer types, the recurrence of these 11 hotspots in 826 non-hypermutated tumors of 18 other cancer types was examined (FIG. 6) Strikingly, it was found that 19% of colorectal cancer tumors were mutated at one or more of the CBS hotspots (FIG. 6A and FIG. 22). Since colorectal cancer have pathological and molecular similarities to gastric cancer, the CBS hotspot mutations may drive cancer progression in colorectal cancer through similar mechanisms as in gastric cancer. The CBS hotspots were mutated at lower frequencies in breast cancer, liver cancer, lung cancer, pancreas cancer and lymphoma. Interestingly, while melanoma and bladder carcinoma also have high genome-wide mutation rates at CBS, none of the CBS hotspots were mutated in these two cancer types. Similarly, it was found that mutations at all CBS hotspots had previously been reported in COSMIC or other genome-wide studies of gastrointestinal tumors (Table 9 below). This suggests that the CBS hotspot mutations are generated and act in a cancer-specific manner.

TABLE 9

CBS hotspot mutations identified in previous genomewide studies of gastrointestinal tumors and the COSMIC database.

| Chr | Start | End | # mut in COSMIC | # mut in Katainen et al. | # met in Umer et al. | Cancer types |
|---|---|---|---|---|---|---|
| chr6 | 50570094 | 50570120 | 12 | 15 | 0 | BRCA, CRC, ESAD, GC, PACA |

TABLE 9-continued

CBS hotspot mutations identified in previous genomewide studies of gastrointestinal tumors and the COSMIC database.

| Chr | Start | End | # mut in COSMIC | # mut in Katainen et al. | # met in Umer et al. | Cancer types |
|---|---|---|---|---|---|---|
| chr8 | 71000992 | 71001012 | 5 | 6 | 0 | CRC, ESAD, HCC, LYMP |
| chr1 | 209422184 | 209422222 | 1 | 0 | 0 | BRCA, CRC |
| chr2 | 49173770 | 49173816 | 24 | 4 | 6 | CRC, ESAD, HCC, PACA, PRAD, OV |
| chr4 | 182064578 | 182064613 | 5 | 6 | 3 | GC, HCC |
| chrX | 104435106 | 104435140 | 6 | 5 | 0 | BRCA, CRC, ESAD, GC, PACA |
| chr14 | 70285576 | 70285601 | 2 | 0 | 0 | CRC, ESAD |
| chr6 | 73122084 | 73122123 | 16 | 9 | 7 | BRCA, GC, ESAD, HCC, PACA |
| chr8 | 70576141 | 70576184 | 10 | 0 | 2 | BRCA, ESAD, GC, HCC, LYMP, PACA |
| chr13 | 36552821 | 36552860 | 11 | 6 | 0 | BRCA, ESAD, GC, HCC, KC, OV, PACA, |
| chr3 | 164903700 | 164903728 | 11 | 0 | 0 | ESAD, GC, HCC, LYMP, PACA |

Figure 7A:
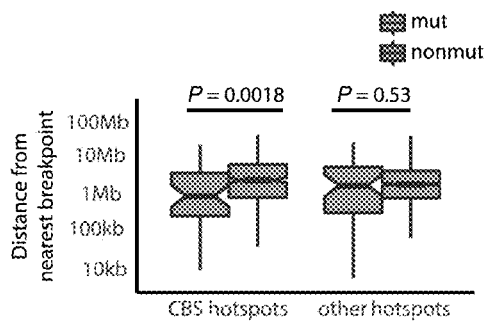
FIG. 7 is an analysis on the association between CBS mutations and chromosomal instability. (A) Distance to the nearest CNV breakpoint from CBS hotspots and other non-CBS mutation hotspots. (B) Distance to the nearest CNV breakpoint from CBSs at loop boundary and non-boundary CBSs. (C) Correlation of mutation rates with SCNA breakpoint density. (D) Correlation of normalized mutation rates with SCNA breakpoint density, correcting for the background mutation rate in each bin. Error bars represent the s.e.m. (E) The violin plots show the VAF distributions of somatic mutations in diploid regions of individual tumors. VAFs of the mutations at CBS hotspots are marked by red vertical lines. (F) Comparison between VAFs of the CBS hotspot mutations and VAFs of non-silent coding mutation on GC driver genes. The darker points represent the median VAFs in each group. The dashed lines match mutations from the same samples. P-value is calculated by paired Wilcoxon rank-sum test.
Figure 7B:
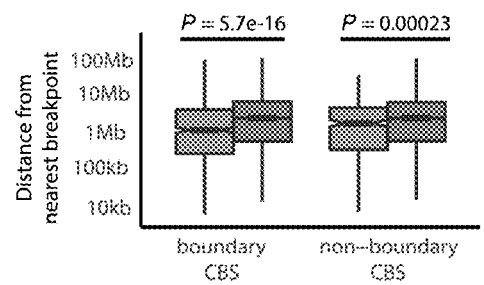
Figure 7C:
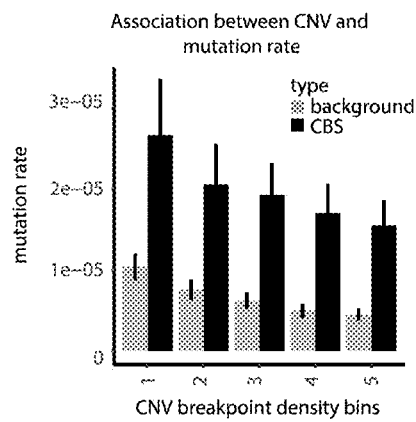
Figure 7D:
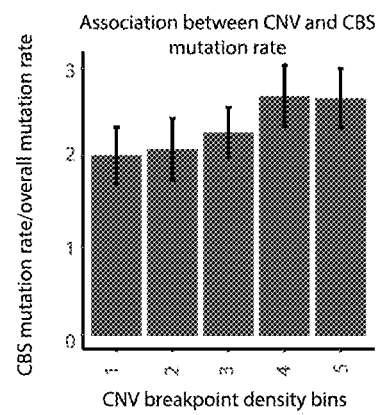

Legend
mut in COSMIC: Number of confirmed somatic mutations at CBS hotspots in COSMICv83
mut in Katainen et al.: mutation clusters identified by Katainen et al. (Table S4)
mut in Umer et al.: CBSs with at least 2 motif breaking mutations from Table S5 of Umer et al.
Kataien et al. studied colorectal cancer; Umer et al. studied liver, gastric, esophageal and pancreatic cancers
Cancer types: cancer types with mutations at CBS hotspots identified in previous studies
BRCA Breast cancer
CRC Colorectal cancer
ESAD Esophageal cancer
GC Gastric cancer
HCC Hepatocellular carcinoma
KC Kidney cancer
LYMP lymphoid neoplasm
OV Ovarian cancer
PACA Pancreatic cancer
PRAD Prostate cancer CBS Mutations are Associated with Chromosomal Instability Enrichment of CBS mutations was highest in CIN tumors, which are characterized by increased chromosomal aneuploidy. This prompted a subsequent examination if mutations at CBSs in CIN tumors were correlated with somatic copy number alteration (SCNA) breakpoints. Strikingly, the distance between a CBS hotspot and its nearest SCNA breakpoint was significantly shorter in mutated than non-mutated tumors (P=0.0018, two-sided Wilcoxon rank-sum test; FIG. 7A). In contrast, non-CBS mutation hotspots showed no such association (P=0.53). The median distance between CBS hotspot mutations and its nearest SCNA breakpoint in the same sample was ~1 Mbp, notably shorter than the ~2 Mbp distance for non-CBS hotspots (FIG. 7A). To study whether this correlation between CBS mutations and SCNA breakpoints was specific to the CBS hotspots, the analysis was extended to all CBSs. Interestingly, it was found that CBS mutations were correlated with occurrence of nearby SCNA breakpoints in the same samples, especially for mutations affecting CBSs at loop boundaries (Wilcoxon P=$5.7 \times 10^{-16}$; FIG. 7B). Conversely, when 1 Mb windows of the genome were grouped according to SCNA breakpoint density, it was found that the normalized CBS mutation rate was positively associated with SCNA breakpoint density (FIG. 7C-D). Overall, these results highlight a link between regional chromosomal instability and mutations at both CBS hotspots and boundary CBSs in general.

As the CBS mutation rate was also elevated in GS tumors (FIG. 4B), it was next investigated if there was a similar association between CBS mutations and SCNA in GS tumors. Although it was found that mutated CBSs also tended to be closer to SCNA breakpoints compared to the non-mutated CBSs in GS tumors, the difference was not statistically significant (FIG. 21), and the relative difference was greater in CIN (2.17-fold difference in distance to nearest breakpoint) compared to GS (1.58-fold difference) tumors. This may indicate that the coupling of CBS mutations and nearby chromosomal instability is a process that is specific to, or exacerbated in, the CIN tumors.

Mutation Hotspots at CTCF Binding Sites are Coupled to Chromosomal Instability in Gastrointestinal Cancers The inventors have performed a comprehensive and unbiased analysis of non-coding SNVs and indels in 212 GC genomes, the largest studied cohort thus far. In addition to a previously identified indel enrichment at LIPF, the analysis identified two other gastric lineage-specific genes with broad enrichment of non-coding indels (PGC and MUC6). The results show that the accumulation of indels occur in multiple lineage specific genes in gastric cancer. Yet, indels at these 3 genes were not associated with change in gene expression. The functional consequences of these indels are therefore still unclear. Strikingly, genome-wide analysis of somatic SNVs revealed 34 significant mutation hotspots (Bonferroni adjusted P-value<0.01) that were disproportionately enriched in CBSs. An increased mutation load at CBSs in colorectal cancer was reported, and another study confirmed the general hypermutation at CBSs in 11 cancer types. Both studies generally discounted CBS mutations as passengers, yet they did not explore the hypothesis that a subset of these mutated CBSs may be undergoing positive selection within individual cancer types. Indeed, a recent study on motif-breaking mutations identified a recurrent CBS mutation that disrupts CTCF binding, confirming the motif-breaking potential of CBS mutations. Here, the inventors used a large cohort of gastric cancer genomes in combination with rigorous statistics, to show that mutation rates at 11 specific CBSs are unexpectedly high and cannot alone be explained by a genome-wide elevated mutation burden at CBS, indicating positive selection at these sites. Out of the 4 CBS hotspots that were examined, 3 of them were associated with nominally significant expression changes of neighboring genes (CENPQ, KCNQ5 and SPG20), and these associations were validated in an independent tumor cohort. Furthermore, it is possible that mutations at these CBS hotspots also have long-range or spatiotemporal regulatory effects on gene expression that are not captured by bulk tumor transcriptome profiling. Overall, the analyses nominate these CBS hotspots as potential drivers in GC, and support the hypothesis that driver mutations may arise as a by-product of the increased mutation load at CBSs followed by positive selection at specific CBSs. This is comparable to a model of genomic rearrangement hotspots in breast cancer, where rearrangements initially arise from defective homologous-recombination-repair and those affecting cancer risk loci are subsequently positively selected, forming rearrangement hotspots.

Figure 7F:
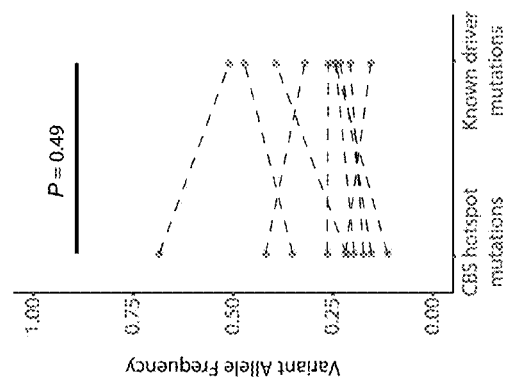
Figure 7E:
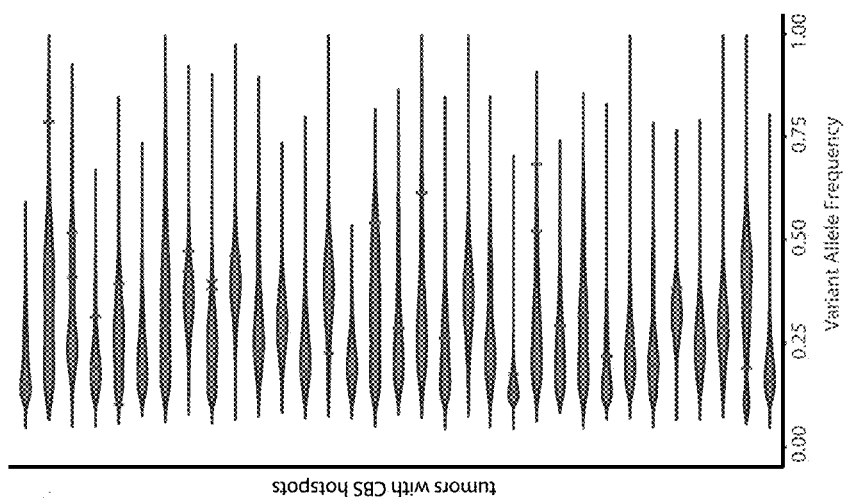

It was found that gastric tumors of the genomic instable subtype (CIN) exhibited the highest mutation rate at CBSs compared to tumors of the other GC subtypes. Furthermore, CBS mutations were associated with the occurrence of nearby chromosomal breakpoints, suggesting a general link between CBS mutations and genomic instability. A previous study has suggested a model where genome higher-order interactions are directly poised for chromosomal breaks. One important open question is whether these processes are coupled, and if so, what is the temporal order of CBS mutations and chromosomal breaks. Interestingly, somatic variant allele frequencies (VAFs) of the CBS hotspot mutations supported that these were generally clonal and likely early events in tumor evolution (FIG. 7E). Furthermore, it was found that the VAFs of CBS hotspot mutations were comparable to non-silent coding mutations of known gastric cancer driver genes from the same sample (paired Wilcoxon P-value=0.49; FIG. 7F).

Previous studies found kilo-base sized regions of hypermutation, termed "kataegis", that tend to co-occur with genomic rearrangements in cancer. Importantly, the present data suggest that the mutational mechanism underlying the association between CBS mutations and DNA breakpoints is distinct from that of kataegis. While kataegis is characterized by C>T and C>G substitutions, CBS mutations are mostly T>G and T>C substitutions. In addition, kataegis is defined by mutation clusters with inter-mutation distance <1 kb. CBS hotspots are confined focal regions of <30 bps including the CTCF motif and its 5' flanking sequence.

Only a subset of tumor samples in the cohort used had paired gene expression data (49/187 samples). This limited the ability to test for functional consequences of CBS hotspot mutations. Additional focused experiments involving transcriptome, copy number, and chromatin structure data should further clarify the regulatory and functional effects of the CBS mutations. The inventors did not uncover a shared theme for the 23 significant non-CBS hotspots. Among the non-CBS hotspots, 7 of them are intronic, 1 is downstream of a gene and the rest are intergenic. None of the genes associated with the hotspots are known cancer drivers. There was no mutation hotspot observed near TERT, confirming that the reactivation of TERT is very rare in gastric cancer 2. For the non-CBS hotspots that overlapped gene regions, focused functional validation experiments could be performed on a case-by-case basis.

The statistics of cancer driver identification is still limited by knowledge of the somatic mutation and repair processes. Although the background model corrected for many covariates of the somatic mutation rate, such as epigenetic and sequence context features, false positives and false negatives could still arise from the current model not considering such unknown mutational biases.

Taken collectively, 25% of gastric cancer tumors and 19% of colorectal cancer tumors are mutated in at least one of the 11 CBS hotspots. Overall, the analyses nominate these CBS hotspots as potentially common drivers of gastrointestinal cancers. Furthermore, the data supports a general link between CBS mutations and chromosomal instability. This suggests that non-coding regulatory mutations could potentially drive tumor evolution through interfacing with cancer genome and epigenome plasticity.

Use of Biomarkers in Liquid Biopsy Assays

Dying tumor cells continually release DNA fragments (~160 nt in length) into the blood circulation. Detection and of such tumor-derived cell-free DNA (cfDNA) has the potential to revolutionize detection and monitoring of cancer. This is especially important for solid tumors where DNA samples can only be obtained via invasive procedures. Furthermore, for purposes of early detection of cancer, relapse or metastasis, liquid biopsies may be the only available approach to identify the presence of cancer cells. One key limitation of cfDNA assays is that cancer DNA fragments only exist at very low frequencies in the blood (often <1%). It is therefore critical to design assays that target specific frequently mutated regions.

The present disclosure involves a comprehensive and uniform analysis of 212 gastric cancer genomes—a pioneer in gastric cancer. A comprehensive statistical approach is developed, incorporating both epigenetic and sequence covariates, to identify non-coding mutation hotspots in gastric cancer. 34 novel non-coding mutational hotspots are identified as potential drivers of gastric cancer (see Table 12 below). Importantly, because mutations happen in concentrated regions ("hotspots"), they are extremely well suited as biomarkers in liquid biopsy assays. Collectively, it is estimated that that mutations in these 34 non-coding hotspots would be detectable in ~54% of gastric cancer patients. Combining these non-coding regions with frequently and focally mutated protein coding regions (such as KRAS, TP53, and RHOA) this number may be increased to about 80% (see Table 10 below).

TABLE 10

| Gene | Cov (%) | AA length | Size (bp) | Probe count | Cov/ probe | Cumulative Pr. | Cumulative # probes |
|---|---|---|---|---|---|---|---|
| KRAS | 6 | 5 | 15 | 1 | 6.00 | 6.0% | 1 |
| Hotspots | 54 | | | 72 | 0.75 | 56.8% | 73 |

TABLE 10-continued

| Gene | Cov (%) | AA length | Size (bp) | Probe count | Cov/ probe | Cumulative Pr. | Cumulative # probes |
|------|---------|-----------|-----------|-------------|------------|----------------|---------------------|
| TP53 | 50 | 250 | 750 | 37.5 | 1.33 | 78.4% | 111 |
| RHOA | 6 | 60 | 180 | 9 | 0.67 | 79.7% | 120 |

Columns:
Cov: Patient coverage, estimated number of patients with mutations
AA length: Number of amino acids in gene that are frequently mutated
Size: Equivalent number of base pairs
Probe count: Number of non-overlapping 20 bp probes needed to cover the region (ignoring exon-intron gaps)
Cov/probe: Estimated patient coverage pr. probe
Cumulative Pr.: Cumulative probability of patient having a mutation in these targeted regions (assuming independence of mutations)
Cumulative # probes: Cumulative number of probes needed Further, mutations in 29 of the 34 potential novel non-coding mutational hotspots (see Table 13 below) are estimated to be detectable in 45% of gastric cancer patients. Combining these 29 non-coding regions with frequently and focally mutated protein coding regions (such as KRAS, TP53, and RHOA), this number may be increased to about 76% (see Table 11 below).

TABLE 11

| Gene | Cov (%) | AA length | Size (bp) | Probe count | Cov/ probe | Cumulative Pr. | Cumulative # probes |
|------|---------|-----------|-----------|-------------|------------|----------------|---------------------|
| KRAS | 6 | 5 | 15 | 2 | 6.00 | 6.0% | 2 |
| Hotspots | 45 | | 706 | 58 | 0.78 | 48.3% | 60 |
| TP53 | 50 | 250 | 750 | 38 | 1.33 | 74.2% | 98 |
| RHOA | 6 | 60 | 180 | 9 | 0.67 | 75.7% | 107 |

The unique advantage of these non-coding regions in cfDNA assays is that the mutations are extremely concentrated and focal (many comparable to KRAS hotspot mutations). This allows design of a compact targeted hybridization approach, which will enable detection of very low frequency cancer DNA fragments in the blood at low cost.

Additional Information on 34 Non-Coding Mutation Hotshots

TABLE 12

| chr | start | end | width | N | q-value | Region | Allele frequency | hotspot sequence | SEQ ID NO |
|-----|-------|-----|-------|---|---------|--------|------------------|------------------|-----------|
| chr6 | 50570094 | 50570120 | 27 | 11 | 1.37E-13 | CBS | 0.28 | CTCTAGTGGAATTTTTTCAGTACTGCA | 1 |
| chr7 | 68391104 | 68391132 | 29 | 9 | 2.12E-09 | intergenic | 0.27 | GGATTTTTTAAAAAAATTTTTTTTAT | 2 |
| chr8 | 71000992 | 71001012 | 21 | 8 | 2.75E-09 | CBS | 0.35 | CTGGCAAAACTTCGGTGCCAA | 3 |
| chr7 | 136495924 | 136495948 | 25 | 9 | 1.71E-07 | intergenic | 0.3 | TACTGGCTTAAGTTTTGGCCCAGCA | 4 |
| chr2 | 57627616 | 57627640 | 25 | 8 | 3.34E-07 | intergenic | 0.36 | ATTTTTCCAAAAATTTTGCAATTAAGGTCCTTTGTTGCCACCT | 5 |
| chr1 | 209422184 | 209422222 | 39 | 7 | 4.90E-07 | CBS | 0.32 | AGTGGCCATTAATTGCACTATAGCCTGTAGTTACTTGATT | 6 |
| chr2 | 49173770 | 49173816 | 47 | 9 | 1.03E-06 | CBS | 0.29 | TCACCACTAGATGGTGATCTTGTATTA | 7 |
| chr2 | 239033350 | 239033370 | 21 | 6 | 3.35E-06 | intron | 0.21 | AGGAGAGTACGTGCATGTGTG | 8 |

TABLE 12-continued

| chr | start | end | width | N | q-value | Region | Allele frequency | hotspot sequence | SEQ ID NO |
|---|---|---|---|---|---|---|---|---|---|
| chr4 | 182064578 | 182064613 | 36 | 7 | 7.83E-06 | CBS | 0.24 | CGCAACCTACAAAACTGCCACCAGGTGGCGCTCACG | 9 |
| chrX | 104435106 | 104435140 | 35 | 7 | 1.08E-05 | CBS | 0.36 | CAGCTCGCCCTCTAGTGGTAATTTTATGAATTGCC | 10 |
| chr16 | 8381278 | 8381302 | 25 | 6 | 1.13E-05 | intergenic | 0.34 | AATAAATAAATAAACAAACAAACAA | 11 |
| chr5 | 23824204 | 23824224 | 21 | 8 | 1.59E-05 | intergenic | 0.18 | AGCAAGCCTAAGTGTGGTCTG | 12 |
| chr7 | 67614923 | 67614943 | 21 | 8 | 1.88E-05 | intergenic | 0.25 | TGAGAGAAACTTAGGGTTTCA | 13 |
| chr14 | 70285576 | 70285601 | 26 | 6 | 2.13E-05 | CBS | 0.32 | TGCACTTATAAATTCTACCACCAGAG | 14 |
| chr6 | 73122084 | 73122123 | 40 | 7 | 2.32E-05 | CBS | 0.23 | GTGGCGCATCTCAGCCACAAGATGGCAGCAGTGCTTCGTG | 15 |
| chr8 | 65161396 | 65161420 | 25 | 7 | 7.08E-05 | intergenic | 0.28 | CATAATCTGAAAATTTTGCAAAGA | 16 |
| chr7 | 4937707 | 4937736 | 30 | 6 | 1.47E-04 | intergenic | 0.22 | TGCTGGCTTAAGTTCAGGGCCACGCTGCCC | 17 |
| chr8 | 70576141 | 70576184 | 44 | 8 | 1.55E-04 | CBS | 0.23 | GTGTTTTCCAAAATGACCACTAGGTGGTAGTCTAGTTCAACTAA | 18 |
| chr12 | 126996666 | 126996686 | 21 | 7 | 1.83E-04 | intergenic | 0.3 | GTAAGAAAACTTAGGTGTAAA | 19 |
| chr1 | 153607104 | 153607124 | 21 | 5 | 3.13E-04 | intron | 0.19 | AAGAAGTACAAGACTTTGAGG | 20 |
| chr4 | 5415060 | 5415082 | 23 | 6 | 3.52E-04 | intron | 0.27 | TTTTAGCTGAAGTTCAGTGGAAT | 21 |
| chr16 | 13516145 | 13516165 | 21 | 6 | 4.73E-04 | intergenic | 0.24 | GATTTTTTTTAAAAAGTTAT | 22 |
| chrX | 137405623 | 137405655 | 33 | 7 | 4.88E-04 | intergenic | 0.25 | TATCTCACTAATAAGGAAGAATTCATCACTTT | 23 |
| chr13 | 36552821 | 36552860 | 40 | 8 | 6.51E-04 | CBS | 0.34 | TAATATCACAATTCGCCACTTGGTGTCACTAGACCTCCAG | 24 |
| chr4 | 62653076 | 62653096 | 21 | 6 | 6.80E-04 | intron | 0.3 | CTTTTTTTTTAAAAAAAAGC | 25 |
| chr3 | 171164993 | 171165017 | 25 | 5 | 9.15E-04 | intron | 0.31 | AATAAATAAATAAACAAACAAACAT | 26 |
| chr4 | 144748744 | 144748764 | 21 | 6 | 1.06E-03 | intergenic | 0.27 | AATTTGTTTGTTTATTTATT | 27 |
| chr3 | 164903700 | 164903728 | 29 | 7 | 1.45E-03 | CBS | 0.38 | AATGGCCTACTTAGATAAGTGCCTGCCTC | 28 |
| chr5 | 1472143 | 1472163 | 21 | 5 | 3.07E-03 | intron | 0.2 | CTGGTCAGAGAGCAGGAGGAA | 29 |
| chr9 | 25481736 | 25481758 | 23 | 7 | 3.66E-03 | intergenic | 0.26 | TTCACCTAAAACTTATCCCCTTA | 30 |
| chr2 | 77150455 | 77150477 | 23 | 6 | 3.88E-03 | intron | 0.33 | ATTTGTAGAAAGTTTGTGAGCTG | 31 |
| chr3 | 104801455 | 104801477 | 23 | 6 | 5.38E-03 | intergenic | 0.25 | AATGGAGTCAAGTTTTCTGAAAT | 32 |
| chrX | 125548690 | 125548710 | 21 | 6 | 6.33E-03 | intergenic | 0.3 | TTGACAGAACTTGTTACATTT | 33 |

TABLE 12-continued

| chr | start | end | width | N | q-value | Region | Allele frequency | hotspot sequence | SEQ ID NO |
|---|---|---|---|---|---|---|---|---|---|
| chr14 | 83046706 | 83046744 | 39 | 7 | 9.67E-03 | intergenic | 0.28 | TTGGACAAACTTGACTTAAATAATAGGCAAGGGACACCT | 34 |

Columns
chr: chromosome
start: start coordinate (Hg19)
end: end coordinate
width: width of hotspot
N: number of samples with mutation (of 168 non-MSI gastric cancer samples)
q-value: Bonferroni-corrected p-value for hotspot
Region: genomic location of hotspot
Allele frequency: Mean allele frequency of hotspot mutations in tumor samples Additional Information on 29 Non-Coding Mutation Hotspots

TABLE 13

| chr | start | end | width | N | q-value | Region | Allele frequency |
|---|---|---|---|---|---|---|---|
| chr6 | 50570094 | 50570120 | 27 | 11 | 1.37E-13 | CBS | 0.28 |
| chr7 | 68391104 | 68391132 | 29 | 9 | 2.12E-09 | intergenic | 0.27 |
| chr8 | 71000992 | 71001012 | 21 | 8 | 2.75E-09 | CBS | 0.35 |
| chr7 | 136495924 | 136495948 | 25 | 9 | 1.71E-07 | intergenic | 0.3 |
| chr2 | 57627616 | 57627640 | 25 | 8 | 3.34E-07 | intergenic | 0.36 |
| chr1 | 209422184 | 209422222 | 39 | 7 | 4.90E-07 | CBS | 0.32 |
| chr2 | 49173770 | 49173816 | 47 | 9 | 1.03E-06 | CBS | 0.29 |
| chr4 | 182064578 | 182064613 | 36 | 7 | 7.83E-06 | CBS | 0.24 |
| chrX | 104435106 | 104435140 | 35 | 7 | 1.08E-05 | CBS | 0.36 |
| chr16 | 8381278 | 8381302 | 25 | 6 | 1.13E-05 | intergenic | 0.34 |
| chr5 | 23824204 | 23824224 | 21 | 8 | 1.59E-05 | intergenic | 0.18 |
| chr7 | 67614923 | 67614943 | 21 | 8 | 1.88E-05 | intergenic | 0.25 |
| chr14 | 70285576 | 70285601 | 26 | 6 | 2.13E-05 | CBS | 0.32 |
| chr6 | 73122084 | 73122123 | 40 | 7 | 2.32E-05 | CBS | 0.23 |
| chr8 | 65161396 | 65161420 | 25 | 7 | 7.08E-05 | intergenic | 0.28 |
| chr7 | 4937707 | 4937736 | 30 | 6 | 1.47E-04 | intergenic | 0.22 |
| chr8 | 70576141 | 70576184 | 44 | 8 | 1.55E-04 | CBS | 0.23 |
| chr12 | 126996666 | 126996686 | 21 | 7 | 1.83E-04 | intergenic | 0.3 |
| chr4 | 5415060 | 5415082 | 23 | 6 | 3.52E-04 | intron | 0.27 |
| chrX | 137405623 | 137405655 | 33 | 7 | 4.88E-04 | intergenic | 0.25 |
| chr13 | 36552821 | 36552860 | 40 | 8 | 6.51E-04 | CBS | 0.34 |
| chr3 | 171164993 | 171165017 | 25 | 5 | 9.15E-04 | intron | 0.31 |
| chr4 | 144748744 | 144748764 | 21 | 6 | 1.06E-03 | intergenic | 0.27 |
| chr3 | 164903700 | 164903728 | 29 | 7 | 1.45E-03 | CBS | 0.38 |
| chr9 | 25481736 | 25481758 | 23 | 7 | 3.66E-03 | intergenic | 0.26 |
| chr2 | 77150455 | 77150477 | 23 | 6 | 3.88E-03 | intron | 0.33 |
| chr3 | 104801455 | 104801477 | 23 | 6 | 5.38E-03 | intergenic | 0.25 |
| chrX | 125548690 | 125548710 | 21 | 6 | 6.33E-03 | intergenic | 0.3 |
| chr14 | 83046706 | 83046744 | 39 | 7 | 9.67E-03 | intergenic | 0.28 |

Columns
chr: chromosome
start: start coordinate (Hg19)
end: end coordinate
width: width of hotspot
N: number of samples with mutation (of 168 non-MSI gastric cancer samples)
q-value: Bonferroni-corrected p-value for hotspot
Region: genomic location of hotspot
Allele frequency: Mean allele frequency of hotspot mutations in tumor samples Primer Sequences

TABLE 14

| Region | Forward | SEQ ID NO. | Reverse | SEQ ID NO. | Size | Hotspot sequence |
|---|---|---|---|---|---|---|
| chr6: 50570094-50570120 | 6_50570094_F: CCTGTCCAGGTATTAGAGAAGG | 35 | 6_50570094_R: AACCCCTCCACCTCCTTTTT | 36 | 144 | CTCTAGTGGAATTTTTTCAGTACTGCA |

TABLE 14-continued

| Region | Forward | SEQ ID NO. | Reverse | SEQ ID NO. | Size | Hotspot sequence |
|---|---|---|---|---|---|---|
| chr7: 68391104-68391132 | 7_68391104_F: CTGACTTGCACCACTCATGC | 37 | 7_68391104_R: GATGGGAGGACTGTTTGAGG | 38 | 118 | GGATTTTTTAAAAAAAATTTTTTTTTAT |
| chr8: 71000992-71001012 | 8_71000992_F: TTCTCCTGCAATGTTTCTCG | 39 | 8_71000992_R: TCACCTTATTTGACTGCTTTGC | 40 | 108 | CTGGCAAAACTTCGGTGCCAA |
| chr7: 136495924-136495948 | 7_136495924_F: CCATGCAGTGGTTACAGTGG | 41 | 7_136495924_R: AGAGGTGGTGGAGGTGATTG | 42 | 118 | TACTGGCTTAAGTTTTGGCCCAGCA |
| chr2: 57627616-57627640 | 2_57627616_F: AGAGCAGGATAAGGCATATTCA | 43 | 2_57627616_R: TGGGACATTTTCCCTTTCAA | 44 | 114 | ATTTTTCCAAAATTTTTGCAATTA |
| chr1: 209422184-209422222 | 1_209422184_F: CACTGCCTACAGCCAATAATCA | 45 | 1_209422184_R: ACCCTGCCTTTTCTTTCATT | 46 | 142 | AGGTCCTTTGTTGCCACCTAGTGGCCATTAATTGCACTA |
| chr2: 49173770-49173816 | 2_49173770_F: GGGGTGCAGAGAAGAATCTG | 47 | 2_49173770_R: ATGCCACCCTTTGTTAGTGG | 48 | 111 | TAGCCTGTAGTTACTTGATTTCACCACTAGATGGTGATCTTGTATTA |
| chr4: 182064578-182064613 | 4_182064578_F: CTTTGCGTGGTGAAAAGAAA | 49 | 4_182064578_R: TTGCTGCTGCTCCAAAGTTA | 50 | 120 | CGCAACCTACAAAACTGCCACCAGGTGGCGCTCACG |
| chrX: 104435106-104435140 | X_104435106_F: CCAGCCAGTTGGTCAATGATAA | 51 | X_104435106_R: GCTAAAAGGGCAATTGTTGG | 52 | 130 | CAGCTCGCCCTCTAGTGGTAATTTTATGAATTGCC |
| chr5: 23824204-23824224 | 5_23824204_F: TGATGTCTGTGATGTTTTCAAGTG | 53 | 5_23824204_R: TGTCAATTTTGAGCCCTCATC | 54 | 107 | AGCAAGCCTAAGTGTGGTCTG |
| chr7: 67614923-67614943 | 7_67614923_F: TTGGAACTCCCTACCCCTAAA | 55 | 7_67614923_R: CATGGATAACCAGCACAGACA | 56 | 113 | TGAGAGAAACTTAGGGTTTCA |
| chr14: 70285576-70285601 | 14_70285576_F: GGTAGGGCACTTGCTGTGTT | 57 | 14_70285576_R: CTGCACCTAAGGGACAGCAG | 58 | 128 | TGCACTTATAAATTCTACCACCAGAG |
| chr6: 73122084-73122123 | 6_73122084_F: CTGCCCTCTGTTGGTGAGAG | 59 | 6_73122084_R: TAGCGCATCAGCATTGACTC | 60 | 147 | GTGGCGCATCTCAGCCACAAGATGGCAGCAGTGCTTCGTG |
| chr8: 65161396-65161420 | 8_65161396_F: AAATGGACTCTCTGCCACTGA | 61 | 8_65161396_R: CAGGACAAAGAGACAAGTGGAG | 62 | 97 | CATAATCTGAAAATTTTTGCAAAGA |
| chr7: 4937707-4937736 | 7_4937707_F: TGCCTTCTAAACCCTCCTGA | 63 | 7_4937707_R: GTCTTTGTGATGGCCCATGT | 64 | 116 | TGCTGGCTTAAGTTCAGGGCCACGCTGCCC |
| chr8: 70576141-70576184 | 8_70576141_F: AAGAGCATCACCCCATCAAG | 65 | 8_70576141_R: CTGGAGCCAAGCAAAGATGT | 66 | 116 | GTGTTTTCCAAAATGACCACTAGGTGGTAGTCTAGTTCAACTAA |
| chr12: 126996666-126996686 | 12_126996666_F: CTGCTGCCTTTATGTTGAAATG | 67 | 12_126996666_R: GCAAAACCAGGAAGAAGCAG | 68 | 136 | GTAAGAAAACTTAGGTGTAAA |
| chr1: 153607104-153607124 | 1_153607104_F: CAGGGCTTTGAGGATGGTAG | 69 | 1_153607104_R: CTGGGAATTAGCTCGCAAAG | 70 | 116 | AAGAAGTACAAGACTTTGAGG |

TABLE 14-continued

| Region | Forward | SEQ ID NO. | Reverse | SEQ ID NO. | Size | Hotspot sequence |
|---|---|---|---|---|---|---|
| chr4: 5415060-5415082 | 4_5415060_F: CAAGGAACAAAGAGCCCAAC | 71 | 4_5415060_R: ATGGAGAAGGCAGAGCTTCA | 72 | 144 | TTTTAGCTGAAGTTCAGTGGAAT |
| chr16: 13516145-13516165 | 16_13516145_F: GCTTCCAGGCTAAAGCACAA | 73 | 16_13516145_R: TCCAGGCTATGTGAATGTTGA | 74 | 142 | GATTTTTTTTAAAAAGTTAT |
| chrX: 137405623-137405655 | X_137405623_F: TGGACATGGTAGGTCCTTGA | 75 | X_137405623_R: TGTGGTCCCATATGGACTTG | 76 | 133 | TATCTCACTAATAAAGGAAGAATTCATCACTTT |
| chr13: 36552821-36552860 | 13_36552821_F: GAACACTCTCAAACAACCAACA | 77 | 13_36552821_R: AATGGGGCCTTACAGAAAAA | 78 | 139 | TAATATCACAATTCGCCACTTGGTGTCACTAGACCTCCAG |
| chr4: 62653076-62653096 | 4_62653076_F: CCAGACATTATTGGACTTCCTG | 79 | 4_62653076_R: TCATTCCCAAATCACTGTCA | 80 | 158 | CTTTTTTTTTAAAAAAAAAGC |
| chr3: 171164993-171165017 | 3_171164993_F: CACTCCAGCCTGGGTAACAG | 81 | 3_171164993_R: GCTATTTGGGGATTAACAGTGA | 82 | 121 | AATAAATAAATAAACAAACAAACAT |
| chr3: 164903700-164903728 | 3_164903700_F: GGGTCTGTGGATCTCTGGAA | 83 | 3_164903700_R: CCGGTATCAAATTGGTGGAG | 84 | 106 | AATGGCCTACTTAGATAAGTGCCTGCCTC |
| chr9: 25481736-25481758 | 9_25481736_F: TCATCAGCACCAGAAACCAG | 85 | 9_25481736_R: TGGATTCTAATGGGGGAAAA | 86 | 95 | TTCACCTAAAACTTATCCCCTTA |
| chr2: 77150455-77150477 | 2_77150455_F: CATGAAACCTCTTGCAACCA | 87 | 2_77150455_R: GGCTCTGTTTAACAACCAGCTC | 88 | 108 | ATTTGTAGAAAGTTTGTGAGCTG |
| chr3: 104801455-104801477 | 3_104801455_F: ACACAGCCAAACTGCATCAA | 89 | 3_104801455_R: AACTATGGGTTGCTCTTGCTTT | 90 | 108 | AATGGAGTCAAGTTTTCTGAAAT |
| chr14: 83046706-83046735 | 14_83046706_F: GCCACATTCAAAGCCATTCT | 91 | 14_83046706_R: CTCAAGGTGTCCCTTGCCTA | 92 | 91 | TTGGACAAACTTGACTTAAATAATAGGCAAGGGACACCT |

Detection of Mutations in the Non-Coding Hotspots in Colorectal Cancer Patients Using Liquid Biopsy Assay Blood samples were collected from metastatic colorectal cancer patients with informed consent. Plasma was obtained from patient blood within 2 hours of venipuncture, followed by centrifugation of blood at 1900 g and 4° C. for 10 min, followed by a second centrifugation of the plasma fraction at 16000 g and 4° C. for 10 min. Plasma was stored at −80° C. until extraction. DNA from plasma was extracted using the QiaAmp Circulating Nucleic Acids Kit (Qiagen), following manufacturer's instructions. The inventors performed whole genome sequencing of the cell free DNA (cfDNA) samples and matched normal samples at 60-90× raw coverage. Sequencing libraries were constructed from cfDNA using the Kapa Hyper Prep Kit and 151 bp paired-end sequencing was performed on an Illumine Hiseq4000. Sequencing reads were aligned to the human reference genome (hg19) using BWA. Pile ups of reads at the 29 non-coding hotspots were generated using samtools. It was found that 5/9 cfDNA samples have more than 3 mutant reads in at least 1 non-coding hotspot (55.6%), and 4/9 cfDNA samples have more than 4 mutant reads in at least 1 non-coding hotspot (44.4%) (see FIG. 23). This is consistent with the previous estimate that mutations in the 29 non-coding hotspots could be detected in ~45% of gastrointestinal cancer patients.

Methods

Gastric Cancer Whole-Genome Sequence Data

Whole genome sequencing of 40 gastric GC tumors and matched normal samples from patients from Singapore (study protocol approved by National University of Singapore Institutional Review Board) were performed. Informed consent was obtained from all participating patients. Genomic DNA of tumors and matched normal gastric tissues was extracted (QIAGEN). Libraries were constructed with 300-400 bp insert length, and 101 bp or 151 bp paired-end sequencing was performed on Illumine Hiseq instruments. The tumors were classified into 4 molecular subtypes as described previously by TCGA 19.

The WGS data of 40 GC tumors from TCGA (gdc.cancer.gov), 32 tumors from ICGC (ega-archive.org/datasets/EGAD00001003132), and 100 tumors were obtained from Wang et al. (HK)[20]. The molecular subtypes of tumors from the TCGA cohort were defined by TCGA. For the HK cohort, only EBV and MSI subtype status was available. The molecular subtypes of tumors from the ICGC cohort were unavailable, but 1 MSI sample was identified from the ICGC cohort using MSIseq[61].

Alignment and Somatic Mutation Calling

Raw sequencing data was uniformly processed using the bcbio-nextgen pipeline (v0.9.3). Briefly, sequencing reads were aligned to the human reference genome (hg19) using BWA[62]. Duplicated reads marked by Picard were removed. Indel regions were realigned using GATK[63]. Somatic mutations were called by four independent mutation callers: VarScan[64], MuTect[65], VarDict[66] and FreeBayes[67] using default parameters of the bcbio-nextgen pipeline. As the nature of the analyses requires high specificity in somatic mutation calling, a random forest predictor, SMuRF, trained on manually curated true somatic mutations was developed to identify high confidence somatic mutation calls from the output of the four mutation callers. For each gastric cancer WGS sample, a set of high confidence consensus calls were obtained by running the random forest prediction algorithm.

Additional Filters to Remove Sequencing Artefacts

False positive somatic calls could arise from sequencing and mapping errors. More false positives tend to be called in the non-coding regions of the genome because these regions are enriched for repeats and low sequence complexity regions. As the downstream mutation recurrence analysis is extremely sensitive to recurrent artefacts in somatic mutation calling, additional post-processing filters were applied to eliminate potential false positive calls. The following candidate somatic mutation calls are removed:
  (i) candidate somatic mutation calls that are found at >1% allele frequency in the 1000 Genomes Project 68 (potential germline mutations)
  (ii) candidate somatic mutation calls that are found in more than 10% of the matched normal samples (potential systematic sequencing errors)
  (iii) candidate somatic mutation calls that are found in more than 1% of the matched normal samples and are within 20 bp to a common indel in the 1000 Genomes Project (potential errors arising from mapping errors near indels).

In addition, indel calls that overlap mono-nucleotide repeats of 8 bp or longer were removed. The final set of somatic SNVs and indels were obtained (data not shown).

Gene Expression Data

RNA-sequencing on 19 matched tumor-normal pairs was performed. Total RNA was extracted using the Qiagen RNeasy Mini kit. RNA-seq libraries were constructed according to manufacturer's instructions using Illumina Stranded Total RNA Sample Prep Kit v2 (Illumina, San Diego, CA), Ribo-Zero Gold option (Epicentre, Madison, WI), and 1 μg total RNA. The completed libraries were validated with Agilent Bioanalyzer (Agilent Technologies, Palo Alto, CA) and the libraries were applied to an Illumina flow cell via the Illumina Cluster Station. RNA-seq reads (2×101 bp) were aligned to the human genome (hg19) using TopHat2-2.0.12 (default parameter and —library-type frfirststrand). Transcript abundances at the gene level were estimated by Cufflinks[68]. The normalized counts of RNA sequencing data of 35 tumors from the TCGA cohort were obtained from the Genomic Data Commons Portal.

Epigenomic and Sequence Covariates of Somatic Mutation Rate

The somatic mutation rate is correlated with epigenetic features such as histone modification and chromatin accessibility, especially those derived from the cell type of origin of the cancer. 36 gastric specific and 24 general chromatin features that potentially affect mutation rate in gastric cancer were compiled. These 66 histone modification profiles and chromatin accessibility profiles were obtained from Roadmap Epigenomics[29] and in-house data. P-value signal tracks of 853 DNaseI and histone modification profiles of 111 primary tissues and cell types were obtained from the Roadmap Epigenomics project. Among them, 27 epigenetic profiles were derived from gastric related tissues. For the 24 histone marks that were not assayed in gastric-related tissues, meta histone modifications profiles were created by taking the median profile of each mark across all tissues and cell-types assayed. In addition, histone modifications profiles of H3K4Me1, H3K4me3, and H3K27Ac of 19 GC tumor/normal samples and 13 gastric cancer cell lines (FU97, KATO3, MKN7, NCC24, NCC59, OCUM1, RERF-GC-1B, SNU16, SNU1750, YCC3, YCC7, YCC21, YCC22) were included[24,70]. The median signal of each histone mark over all tumour samples, all normal samples, and all cell lines were used respectively.

Replication timing profiles were not available for gastric tissue. The inventors therefore used the mean replication timing profile of 13 cell lines (Bj, Nhek, K562, Mcf7, Gm06990, Gm12812, Imr90, Hepg2, Helas3, Gm12801, Huvec, Gm12878 Gm12813) generated by ENCODE[71].

Binding profiles of 132 transcription factors and a metaprofile of all transcription factor binding sites were obtained from the Ensembl Regulatory Build[72]. Generic TF binding profiles were used as there is no comprehensive TF-binding assay done in gastric tissue. In total, 194 candidate epigenetic covariates potentially informative of somatic mutation rates in GC were considered (data not shown).

To identify sequence context features affecting somatic mutation accumulation in GC, 1-mer, 3-mer, and 5-mer nucleotide motifs centred at the mutated site, as well as 1-bp and 2-bp left/right flank motifs of the site were considered. All nucleotide context features were grouped into reverse compliment pairs. As indels tend to occur in poly-monomer sequences, especially poly-A and poly-T sequences, the presence of poly-A, poly-T, poly-G and poly-C sequences at the indel sites was used as features in the indel background mutation model.

Lastly, local mutation rate was included as a covariate to account for other unknown factors affecting mutation rate. The local mutation rate was calculated for 100 kb non-overlapping bins across the genome after masking CDS regions, immunoglobulin loci and poorly mappable regions (mappability score <1 in the ENCODE 75mers Alignability track).

PCA on the Epigenetic Features

The genome was divided into 1 Mb non-overlapping windows. CDS regions, immunoglobulin loci and poorly mappable regions were masked from the genomic windows. Windows smaller than 250 kb after masking were removed. The mean signal of each epigenetic feature (in FIG. 1B) and the mutation rate of each tumour in each window were calculated. The Pearson correlations between the epigenetic features and mutation rates of the tumour were calculated. To identify the contributions of epigenetic features to the variance in the mutation rate of individual tumours, PCA was performed on the correlation matrix between the mutation rates of individual tumours and epigenetic features using the prcomp function in R. The contribution of each feature to a principal component is calculated as the feature's loading (rotation) divided by the sum of loadings of all features for that principal component.

Feature Selection Using LASSO Regression

The least absolute shrinkage and selection operator (LASSO) is a regularized regression approach commonly used for automated feature selection. LASSO penalizes the sum of the absolute size of the regression coefficients, forcing some of the regression coefficients to shrink to zero, thereby selecting a simpler and more interpretable model. The LASSO objective function can be written as:

$$\min_{\beta_0, \beta} \frac{1}{N} \sum_{i=1}^{N} l(y_i, \beta_0 + \beta^T x_i) + \lambda \|\beta\|_1$$

Where l is the negative log-likelihood function and λ is the regularization parameter.

LASSO logistic regression was used to identify the most informative features for modelling the somatic mutation rate in gastric cancer. As it is computationally expensive to run a logistic regression on all positions in the non-coding genome with a large number of predictor variables, the inventors used all mutated sites and an equal number of randomly sampled non-mutated sites as the input for feature selection in the LASSO logistic regression model. The inventors regressed the binary mutation status of each site against the mean signal of each feature over an 11 bp region centred at the site. The regularization parameter λ was chosen by 10-fold cross-validation such that the error of the selected model was within 1 standard deviation from the minimum error. LASSO regression and cross validation were performed using the 'glmnet' package in R.

*glm*net(*y*~β*X*,family=logistic)

The inventors bootstrapped 100 samples with 50% of the data at each bootstrap, and performed LASSO regression using the bootstrap samples. Assuming that the most informative features would be robustly selected, features selected in more than 95% of the bootstrap samples were used for the final regression model.

Tumor-Specific Background Mutation Model

The patient specific background mutation probabilities were estimated by fitting a logistic regression model on all genomic sites after masking CDS regions, immunoglobin loci and poorly mappable regions. Replication timing was discretized into 8 equally sized bins, the local mutation rate was discretized into equally sized bins, and the chromatin features and TF-binding profiles were binarized. P-value signal tracks of the histone modification profiles from the Roadmap Epigenomics were binarized using a cutoff of $10^{-4}$. ENCODE TF-binding profiles were binarized according to the presence of a peak in any cell line assayed. Logistic regression was performed using the frequency table of the counts of mutated and non-mutated sites for each combination of the covariates. Separate logistic regression models were fit to estimate the background mutation probabilities of SNVs and indels. This is to account for the different mutational processes from which SNVs and indels arise, as well as the different uncertainties associated with SNV and indel calls.

*glm*(*y*~rep+epi+sequence+pid,family=logit)

Here rep is the Repli-seq profile, epi represents the epigenomic features, sequence represents the sequence context features and pid is the patient ID. Features used in each model are shown in FIG. 9.

Poisson Binomial Model of Mutation Recurrence

For a specific region of interest, the probability, $p_i$, of mutation in tumor i is a function of the length of that region and the expected mutation rates of individual nucleotides in that region under the null hypothesis. Assuming $q_{i,j}$ is the mutation probability of nucleotide j in tumor i, and l is the length of the region of interest:

$$p_i = 1 - \prod_{j=0}^{l} (1 - q_{i,j})$$

Mutation recurrence is then modelled using the Poisson binomial distribution, which accounts for variation in mutation rate across tumours. For a specific region of interest, the probability of having mutations in k or more individuals is given by:

$$Pr(K \geq k) = \sum_{m=k}^{n} \sum_{A \in F_m} \prod_{i \in A} p_i \prod_{j \in A^c} (1 - p_j)$$

Here n is the total number of tumors sequenced, k is the number of tumors with mutations in the region of interest, $F_m$ is the set of all subsets of k integers selected from {1, 2, ..., n}, A is a subset of $F_m$, $A^c$ is the complement of set A, $p_i$ is the probability of mutation in tumor i, and $p_j$ is the probability of mutation in tumor j. The Poisson binomial probability is calculated using an efficient and accurate normal approximation in the 'poibin' R package.

Identification of Mutation Hotshots

The hotspot analysis aims to identify small focal regions with high mutation rates. The inventors first considered all mutated 21 bp regions by taking 10 bp flanks on each side of each mutation. Then the mutation recurrence scores for all 21 bp regions with 3 or more mutated samples (2 or more for indels) were calculated. The P value of mutation recurrence of each hotspot was calculated using the Poisson binomial model described in the previous section. The total number of hypothesis tested is equal to the number of bases in the masked non-coding genome. The Bonferroni correction was used to adjust for multiple testing of 2,533,374,732 hypotheses, to maintain the overall a at 0.01.

Identification of Gene Non-Coding Regions with Indel Recurrence

Non-coding regions of genes with recurrence of indels were scanned for. Gene regions were defined by Ensembl v75 annotations. The inventors considered the merged non-coding regions of each gene by masking all coding regions of each gene, and extending the gene boundaries by 1 kb to take into account its promoter region. The mutation recurrence scores were calculated for all protein-coding genes, and their individual merged non-coding regions, using the Poisson binomial model described in the previous section. The Bonferroni correction was used to maintain the overall a at 0.01.

Enrichment of Mutation Hotspots in Functional Regions

The log odds ratio of the enrichment of hotspot mutations in TF binding regions and conserved DNA elements was calculated. Gastric-specific TFBSs were defined as a ChIP-seq peak of a TF in any of the ENCODE cell lines that overlaps a gastric tissue DNaseI hypersensitivity site (data from Roadmap Epigenomics). Constitutive TFBSs are defined as TFBSs with $P_{tfbs} > 0.75$, where $P_{tfbs}$ is the probability that the TFBS is bound by a TF for any given ENCODE cell line. $P_{tfbs}$ for all TFBSs were obtained from the ENSEMBL regulatory build. Conserved elements generated by GERP[73] from the alignment of hg19 to 36 mammals were downloaded from the UCSC genome browser.

The expected fraction of hotspot (or non-hotspot) mutations in the functional region type ($p_2$) is the fraction of the genome that constitutes the functional region. The observed fraction of hotspot (or non-hotspot) mutations in the functional region is calculated by adding all mutations in the functional region type and dividing by the total number of mutations genome-wide ($p_1$). The log odds ratio of the enrichment of hotspot (or non-hotspot) mutations in a functional region type is given by, $$LOD = \ln\left(\frac{p_1/(1-p_1)}{p_2/(1-p_2)}\right)$$

The standard error of the LOD is calculated as, $$SE_{LOR} = \sqrt{\frac{SE_{p1}^2}{p1^2 - (1-p1)^2} + \frac{SE_{p2}^2}{p2^2 - (1-p2)^2}}$$

The statistical significance of the enrichment was evaluated by the Z-test.

Identification of Gastric-Specific CBSs

The position weight matrix of the CTCF binding motif was obtained from JASPAR[74]. Genomic locations of CTCF binding motifs were identified using the FIMO[75] function of the MEME tool suite[76] with a P-value threshold of 0.01. Gastric specific CBSs were defined as CBS motifs overlapping both a CTCF ChIP-seq peak in at least one ENCODE cell line and a DNaseI hypersensitivity site in gastric tissue from Roadmap epigenomics. The set of constitutive CTCF-CTCF loops shared across 3 cell lines (GM12878, Jurkat and K562) obtained from the supplementary information of Hnisz et al[13] were used. CBSs that overlap the boundaries of these constitutive CTCF loops were defined as boundary CBSs.

The CBS-Specific Background Model

For the CBS specific background model, the model and search space were limited to CBS regions and their 5 bp flanking DNA.

$glm(y_{CBS}$~rep+subtype+boundary+sequence+pid+
    mutsig1+mutsig17,family=logit)

Here subtype is the tumor subtype, boundary indicates if the CBS is located at a CTCF loop boundary, and mutsig1 and mutsig17 represent the percentage contributions of signature 1 and signature 17 of the tumor. DeconstructSigs[76] was used to quantify the prevalence of each of the 30 COSMIC consensus mutation signatures in each tumor.

The P value of mutation recurrence of each CBS was calculated using the Poisson binomial model described in the previous section. The Bonferroni correction was applied to maintain the overall α at 0.01.

Motif Analysis of Hotspot Mutations in CTCF Motif Flanks

The ±40 bp sequence context around each mutation was extracted, and DeepBind was used to predict the binding scores of 472 TFs for the reference (ref score) and mutated sequences (alt score) of each mutation. Since the binding scores output by DeepBind are on an arbitrary scale and vary between different TF models, the background distributions of the binding scores of each TF were estimated by applying DeepBind to 10,000 randomly sampled non-hotspot mutations. For a particular TF, a mutation is predicted to be motif-disrupting if its reference sequence scores higher than 99.9% of the random mutations, and the score difference between its alternate and reference sequences (alt score–ref score) is smaller than 99.9% of the random mutations for that TF. A mutation is predicted to create a motif for a specific TF if its alternate sequence scores higher than 99.9% of the random mutations, and the score difference between its alternate and reference sequences (alt score–ref score) is greater than 99.9% of the random mutations for that TF.

Pan-Cancer Analysis of Mutation Recurrence at CBS Hotspots

Somatic mutations of 858 tumors from 22 cancer types were downloaded from the supplementary information of Weinhold et al[5]. Hypermutated tumors with more than 200,000 mutations were excluded from the analysis. Cancer types with less than 10 samples were excluded from the analysis. For CBS mutation rate calculation in FIG. 6B, CBSs were defined as CTCF motifs overlapping a CTCF ChIP-seq peak in at least one ENCODE cell line. The inventors further defined tissue-specific CBSs for 14/19 cancer types for which DNaseI profiles in the matched tissue types are available in Roadmap Epigenomics. Tissue-specific CBSs were defined as generic CBSs that fall under DNaseI peaks in the respective tissue. FIG. 22 shows the mutation rates at tissue-specific CBSs.

Analysis of SCNA Breakpoints

Copy number segmentations were generated by CNVkit[77] using default settings (bcbio-nextgen v0.9.3). SCNA breakpoints were defined as the ends of non-diploid segments. Assuming tumor purity of 50%, the estimated mean purity of these tumors, non-diploid segments were defined as segments with log 2(tumor coverage/normal coverage)<log 2(1.5/2) or log 2(tumor coverage/normal coverage)>log 2(2.5/2).

Analysis of Variant Allele Frequencies

The list of known gastric cancer driver genes was collated from the Cancer Gene Census[79] and the driver genes identified by TCGA[19] and Wang et al.[20]. TP53 was excluded from the analysis as TP53 frequently undergo deletions and loss of heterozyosity. Nonsynonymous and truncating mutations on known gastric cancer driver genes were identified, and their VAFs were compared to the VAFs of CBS hotspot mutations from the same samples using a matched Wilcoxon rank-sum test. Only mutations in diploid regions in each sample were included in the analysis.

Code Availability

R was code used to generate some of the figures and statistics of the paper (data not shown). Source code for the ensemble somatic mutation caller, SMuRF, can be found at github.com/skandlab/SMuRF. Source code for estimating background mutation rate from genomic covariates and identification of non-coding mutation hotspots is available at: github.com/skandlab/MutSpot.

Data Availability

SG tumor data: Sequence data has been deposited at the European Genome-phenome Archive (EGA), which is hosted by the EBI and the CRG, under accession number EGAS 00001002872.

TCGA tumor data: portal.gdc.cancer.gov/projects/TCGA-TAD

ICGC tumor data: ega-archive.org/datasets/EGAD00001003132

HK tumor data: ega-archive.org/datasets/EGAD00001000782

Roadmap Epigenomics data: www.roadmapepigenomics.org/data/

Encode data: ftp.ensembl.org/pub/release-85/regulation/homo_sapiens/

REFERENCES

1. Encode Project Consortium. An integrated encyclopedia of DNA elements in the human genome. *Nature* 489, 57-74 (2012).
2. Huang F W, Hodis E, Xu M J, Kryukov G V, Chin L, Garraway L A. Highly recurrent TERT promoter mutations in human melanoma. *Science* 339, 957-959 (2013).
3. Vinagre J, et al. Frequency of TERT promoter mutations in human cancers. *Nat Commun* 4, 2185 (2013).
4. Mansour M R, et al. Oncogene regulation. An oncogenic super-enhancer formed through somatic mutation of a noncoding intergenic element. *Science* 346, 1373-1377 (2014).
5. Weinhold N, Jacobsen A, Schultz N, Sander C, Lee W. Genome-wide analysis of noncoding regulatory mutations in cancer. *Nat Genet* 46, 1160-1165 (2014).
6. Melton C, Reuter J A, Spacek D V, Snyder M. Recurrent somatic mutations in regulatory regions of human cancer genomes. *Nat Genet* 47, 710-716 (2015).
7. Lawrence M S, et al. Discovery and saturation analysis of cancer genes across 21 tumour types. *Nature* 505, 495-501 (2014).
8. Nik-Zainal S, et al. Landscape of somatic mutations in 560 breast cancer whole-genome sequences. *Nature* 534, 47-54 (2016).
9. Fujimoto A, et al. Whole-genome mutational landscape and characterization of noncoding and structural mutations in liver cancer. *Nat Genet* 48, 500-509 (2016).
10. Feigin M E, et al. Recurrent noncoding regulatory mutations in pancreatic ductal adenocarcinoma. *Nat Genet*, (2017).
11. Ghirlando R, Felsenfeld G. CTCF: making the right connections. *Genes Dev* 30, 881-891 (2016).
12. Phillips J E, Corces V G. CTCF: master weaver of the genome. *Cell* 137, 1194-1211 (2009).
13. Hnisz D, et al. Activation of proto-oncogenes by disruption of chromosome neighborhoods. *Science* 351, 1454-1458 (2016).
14. Flavahan W A, et al. Insulator dysfunction and oncogene activation in IDH mutant gliomas. *Nature* 529, 110-114 (2016).
15. Katainen R, et al. CTCF/cohesin-binding sites are frequently mutated in cancer. *Nat Genet* 47, 818-821 (2015).
16. Sabarinathan R, Mularoni L, Deu-Pons J, Gonzalez-Perez A, Lopez-Bigas N. Nucleotide excision repair is impaired by binding of transcription factors to DNA. *Nature* 532, 264-267 (2016).
17. Perera D, Poulos R C, Shah A, Beck D, Pimanda J E, Wong J W. Differential DNA repair underlies mutation hotspots at active promoters in cancer genomes. *Nature* 532, 259-263 (2016).
18. Kaiser V B, Taylor M S, Semple C A. Mutational Biases Drive Elevated Rates of Substitution at Regulatory Sites across Cancer Types. *PLoS Genet* 12, e1006207 (2016).
19. Cancer Genome Atlas Research N. Comprehensive molecular characterization of gastric adenocarcinoma. *Nature* 513, 202-209 (2014).
20. Wang K, et al. Whole-genome sequencing and comprehensive molecular profiling identify new driver mutations in gastric cancer. *Nat Genet* 46, 573-582 (2014).
21. Zang Z J, et al. Exome sequencing of gastric adenocarcinoma identifies recurrent somatic mutations in cell adhesion and chromatin remodeling genes. *Nat Genet* 44, 570-574 (2012).
22. Alexandrov L B, Nik-Zainal S, Siu H C, Leung S Y, Stratton M R. A mutational signature in gastric cancer suggests therapeutic strategies. *Nat Commun* 6, 8683 (2015).
23. Nagarajan N, et al. Whole-genome reconstruction and mutational signatures in gastric cancer. *Genome Biol* 13, R115 (2012).
24. Ooi W F, et al. Epigenomic profiling of primary gastric adenocarcinoma reveals super-enhancer heterogeneity. *Nat Commun* 7, 12983 (2016).
25. Qamra A, et al. Epigenomic Promoter Alterations Amplify Gene Isoform and Immunogenic Diversity in Gastric Adenocarcinoma. *Cancer Discov*, (2017).
26. Alioto T S, et al. A comprehensive assessment of somatic mutation detection in cancer using whole-genome sequencing. *Nat Commun* 6, 10001 (2015).
27. Chen L, Liu P, Evans T C, Jr., Ettwiller L M. DNA damage is a pervasive cause of sequencing errors, directly confounding variant identification. *Science* 355, 752-756 (2017).
28. Costello M, et al. Discovery and characterization of artifactual mutations in deep coverage targeted capture sequencing data due to oxidative DNA damage during sample preparation. *Nucleic Acids Res* 41, e67 (2013).
29. Roadmap Epigenomics Consortium, et al. Integrative analysis of 111 reference human epigenomes. *Nature* 518, 317-330 (2015).
30. Schuster-Bockler B, Lehner B. Chromatin organization is a major influence on regional mutation rates in human cancer cells. *Nature* 488, 504-507 (2012).
31. Supek F, Lehner B. Differential DNA mismatch repair underlies mutation rate variation across the human genome. *Nature* 521, 81-84 (2015).
32. Polak P, et al. Cell-of-origin chromatin organization shapes the mutational landscape of cancer. *Nature* 518, 360-364 (2015).
33. Aggarwala V, Voight B F. An expanded sequence context model broadly explains variability in polymorphism levels across the human genome. *Nat Genet* 48, 349-355 (2016).
34. Prasad R, et al. Cloning of the ALL-1 fusion partner, the AF-6 gene, involved in acute myeloid leukemias with the t(6;11) chromosome translocation. *Cancer Res* 53, 5624-5628 (1993).
35. Letessier A, et al. Correlated break at PARK2/FRA6E and loss of AF-6/Afadin protein expression are associated with poor outcome in breast cancer. *Oncogene* 26, 298-307 (2007).
36. Xu Y, et al. Loss of polarity protein AF6 promotes pancreatic cancer metastasis by inducing Snail expression. *Nat Commun* 6, 7184 (2015).
37. Petryszak R, et al. Expression Atlas update—an integrated database of gene and protein expression in humans, animals and plants. *Nucleic Acids Res* 44, D746-752 (2016).
38. Consortium G T. The Genotype-Tissue Expression (GTEx) project. *Nat Genet* 45, 580-585 (2013).
39. Imielinski M, Guo G, Meyerson M. Insertions and Deletions Target Lineage-Defining Genes in Human Cancers. *Cell* 168, 460-472 e414 (2017).

40. Umer H M, et al. A Significant Regulatory Mutation Burden at a High-Affinity Position of the CTCF Motif in Gastrointestinal Cancers. *Hum Mutat* 37, 904-913 (2016).
41. Dixon J R, et al. Topological domains in mammalian genomes identified by analysis of chromatin interactions. *Nature* 485, 376-380 (2012).
42. Rao S S, et al. A 3D map of the human genome at kilobase resolution reveals principles of chromatin looping. *Cell* 159, 1665-1680 (2014).
43. Heidari N, et al. Genome-wide map of regulatory interactions in the human genome. *Genome Res* 24, 1905-1917 (2014).
44. Alexandrov L B, et al. Signatures of mutational processes in human cancer. *Nature* 500, 415-421 (2013).
45. Okada M, et al. The CENP-H-I complex is required for the efficient incorporation of newly synthesized CENP-A into centromeres. *Nat Cell Biol* 8, 446-457 (2006).
46. Ren L, Wang Y, Shi M, Wang X, Yang Z, Zhao Z. CTCF mediates the cell-type specific spatial organization of the Kcnq5 locus and the local gene regulation. *PLoS One* 7, e31416 (2012).
47. Bakowska J C, Jupille H, Fatheddin P, Puertollano R, Blackstone C. Troyer syndrome protein spartin is monoubiquitinated and functions in EGF receptor trafficking. *Mol Biol Cell* 18, 1683-1692 (2007).
48. Dulak A M, et al. Exome and whole-genome sequencing of esophageal adenocarcinoma identifies recurrent driver events and mutational complexity. *Nat Genet* 45, 478-486 (2013).
49. Varley K E, Mitra R D. Bisulfite Patch PCR enables multiplexed sequencing of promoter methylation across cancer samples. *Genome Res* 20, 1279-1287 (2010).
50. Kim Y H, et al. Epigenomic analysis of aberrantly methylated genes in colorectal cancer identifies genes commonly affected by epigenetic alterations. *Ann Surg Oncol* 18, 2338-2347 (2011).
51. Lind G E, et al. SPG20, a novel biomarker for early detection of colorectal cancer, encodes a regulator of cytokinesis. *Oncogene* 30, 3967-3978 (2011).
52. Bruce A W, et al. Functional diversity for REST (NRSF) is defined by in vivo binding affinity hierarchies at the DNA sequence level. *Genome Res* 19, 994-1005 (2009).
53. Essien K, Vigneau S, Apreleva S, Singh L N, Bartolomei M S, Hannenhalli S. CTCF binding site classes exhibit distinct evolutionary, genomic, epigenomic and transcriptomic features. *Genome Biol* 10, R131 (2009).
54. Pollard K S, Hubisz M J, Rosenbloom K R, Siepel A. Detection of nonneutral substitution rates on mammalian phylogenies. *Genome Res* 20, 110-121 (2010).
55. Alipanahi B, Delong A, Weirauch M T, Frey B J. Predicting the sequence specificities of DNA- and RNA-binding proteins by deep learning. *Nat Biotechnol* 33, 831-838 (2015).
56. Bijlsma M F, Sadanandam A, Tan P, Vermeulen L. Molecular subtypes in cancers of the gastrointestinal tract. *Nat Rev Gastroenterol Hepatol*, (2017).
57. Forbes S A, et al. COSMIC: somatic cancer genetics at high-resolution. *Nucleic Acids Res* 45, D777-D783 (2017).
58. Glodzik D, et al. A somatic-mutational process recurrently duplicates germline susceptibility loci and tissue-specific super-enhancers in breast cancers. *Nat Genet* 49, 341-348 (2017).
59. Fudenberg G, Getz G, Meyerson M, Mirny L A. High order chromatin architecture shapes the landscape of chromosomal alterations in cancer. *Nat Biotechnol* 29, 1109-1113 (2011).
60. Nik-Zainal S, et al. Mutational processes molding the genomes of 21 breast cancers. *Cell* 149, 979-993 (2012).
61. Huang M N, McPherson J R, Cutcutache I, Teh B T, Tan P, Rozen S G. MSIseq: Software for Assessing Microsatellite Instability from Catalogs of Somatic Mutations. *Sci Rep* 5, 13321 (2015).
62. Li H, Durbin R. Fast and accurate short read alignment with Burrows-Wheeler transform. *Bioinformatics* 25, 1754-1760 (2009).
63. McKenna A, et al. The Genome Analysis Toolkit: a MapReduce framework for analyzing next-generation DNA sequencing data. *Genome Res* 20, 1297-1303 (2010).
64. Koboldt D C, et al. VarScan 2: somatic mutation and copy number alteration discovery in cancer by exome sequencing. *Genome Res* 22, 568-576 (2012).
65. Cibulskis K, et al. Sensitive detection of somatic point mutations in impure and heterogeneous cancer samples. *Nat Biotechnol* 31, 213-219 (2013).
66. Lai Z, et al. VarDict: a novel and versatile variant caller for next-generation sequencing in cancer research. *Nucleic Acids Res* 44, e108 (2016).
67. Garrison E, Marth G. Haplotype-based variant detection from short-read sequencing. Preprint at http://adsabs.harvard.edu/abs/2012arXiv1207.3907G (2012).
68. Genomes Project C, et al. A global reference for human genetic variation. *Nature* 526, 68-74 (2015).
69. Trapnell C, et al. Transcript assembly and quantification by RNA-Seq reveals unannotated transcripts and isoform switching during cell differentiation. *Nat Biotechnol* 28, 511-515 (2010).
70. Qamra A, et al. Epigenomic Promoter Alterations Amplify Gene Isoform and Immunogenic Diversity in Gastric Adenocarcinoma. *Cancer Discov* 7, 630-651 (2017).
71. Hansen R S, et al. Sequencing newly replicated DNA reveals widespread plasticity in human replication timing. *Proc Natl Acad Sci USA* 107, 139-144 (2010).
72. Zerbino D R, Wilder S P, Johnson N, Juettemann T, Flicek P R. The ensembl regulatory build. *Genome Biol* 16, 56 (2015).
73. Davydov E V, Goode D L, Sirota M, Cooper G M, Sidow A, Batzoglou S. Identifying a high fraction of the human genome to be under selective constraint using GERP++. *PLoS Comput Biol* 6, e1001025 (2010).
74. Mathelier A, et al. JASPAR 2016: a major expansion and update of the open-access database of transcription factor binding profiles. *Nucleic Acids Res* 44, D110-115 (2016).
75. Grant C E, Bailey T L, Noble W S. FIMO: scanning for occurrences of a given motif. *Bioinformatics* 27, 1017-1018 (2011).
76. Bailey T L, et al. MEME SUITE: tools for motif discovery and searching. *Nucleic Acids Res* 37, W202-208 (2009).
77. Rosenthal R, McGranahan N, Herrero J, Taylor B S, Swanton C. DeconstructSigs: delineating mutational processes in single tumors distinguishes DNA repair deficiencies and patterns of carcinoma evolution. *Genome Biol* 17, 31 (2016).
78. Talevich E, Shain A H, Botton T, Bastian B C. CNVkit: Genome-Wide Copy Number Detection and Visualization from Targeted DNA Sequencing. *PLoS Comput Biol* 12, e1004873 (2016).
79. Futreal P A, et al. A census of human cancer genes. *Nat Rev Cancer* 4, 177-183 (2004).

APPLICATIONS

It is believed that no disclosure before the present disclosure has rigorously tested the hypothesis that even amidst a general elevated mutational burden at CBSs, positive selection may still act on specific CBSs to drive cancer in individual tumor types. Indeed, to accurately identify such genomic sites under positive selection, statistical tests must take into account regional biases in the mutation burden. In the present disclosure, the inventors have performed uniform and accurate identification of somatic single nucleotide variants (SNVs) and insertions/deletions (indels) in 212 GC genomes using an ensemble mutation calling approach. A comprehensive statistical approach was developed, incorporating both epigenetic and sequence covariates, to accurately model background mutational processes and identify non-coding regions with significantly higher mutation burdens over background, indicating positive selection and a role in gastric tumorigenesis.

Performing an unbiased genome-wide scan of focal mutation hotspots (~20 bp, as TF binding motifs are typically <20 bp), significant enrichment of non-coding indels (insertions/deletions) in three gastric lineage-specific genes (LIPF, PGC and MUC6) was observed. Furthermore, 34 significantly mutated and recurring focal regions (hotspots), of which 11 overlapped CTCF binding sites (CBSs) were identified. These 11 CBS hotspots remained significant even after controlling for genome-wide elevated mutation rate at CBSs. In 3 out of 4 tested CBS hotspots, mutations were nominally associated with expression change of neighboring genes (CENPQ, KCNQ5, SPG20). CBS hotspot mutations were enriched in tumors showing chromosomal instability, co-occurred with neighboring chromosomal aberrations, and were common in gastric (25%) and colorectal (19%) tumors but rare in other cancer types (CTCF hotspot mutations are frequent (20-25%) in gastrointestinal tumors). Thus, the present disclosure has identified mutational disruption of specific CBSs as a potential tissue-specific mechanism of tumorigenesis conserved across gastrointestinal cancers.

The hotspots are further characterised in the present disclosure by analyzing CBS specific mutation biases, gene expression of neighboring genes, chromosomal instability, and incidence of these mutations in other cancer types. Particularly, the present disclosure has found that mutations at boundary CTCF binding sites are associated with neighboring chromosomal instability. Overall, the present disclosure has identified the CBS hotspots as candidate drivers of gastrointestinal cancers, and elucidated a general link between CBS mutations and chromosomal instability in gastrointestinal cancers.

Notably, previous cases/examples or studies cover mutations only in protein-coding regions in gastrointestinal cancers. It is believed that the mutated non-coding regions identified in the present disclosure have not previously been reported in gastrointestinal cancers including gastric cancer. Furthermore, it is believed that there are no prior studies investigating the use of non-coding mutations in cancer cfDNA assays. Indeed, the identified non-coding regions/hotspots could only have been reliably discovered with >150 samples/tumors (signal/noise ratio). Before the present disclosure, no such datasets or studies exist.

Advantageously, the CBS hotspots identified in the present disclosure, being extremely concentrated and focal, are well suited for use in a liquid biopsy method for detecting and monitoring of gastrointestinal cancer such as gastric cancer (via, inter alia, detecting, capturing and sequencing the non-coding DNA fragments). This includes early detection and monitoring of disease relapse and metastasis. Further advantageously, the present disclosure also provides hybridization probes (or PCR primers) useful for capturing and sequencing the 34 potential non-coding mutational hotspot regions (each ~20 nt long).

The present disclosure, in identifying novel cancer-causing mutations, has the potential to contribute new disease biomarkers, improved patient diagnosis, and entirely new therapeutic paradigms.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The so present embodiments are, therefore, to be considered in all respects to be illustrative and not restrictive.

The invention claimed is:

1. A method of detecting, determining and/or diagnosing gastrointestinal cancer in a human subject, the method comprising:
   i) extracting nucleic acid from a fluid biological sample of the subject, wherein the fluid biological sample is selected from the group consisting of blood, plasma, serum, and combinations thereof,
   ii) contacting the nucleic acid from the sample with an agent for detecting the presence of a mutation in one or more focal regions with high mutation rates,
   iii) detecting the presence of mutation in one or more focal regions with high mutation rates,
   wherein the one or more focal regions is selected from the group consisting of CTCF-binding sites (CBS) overlapping regions set forth in the table 1 below:

| Chromosome | Start site | End site  |
|------------|------------|-----------|
| 6          | 50570094   | 50570120  |
| 8          | 71000992   | 71001012  |
| 1          | 209422184  | 209422222 |
| 2          | 49173770   | 49173816  |
| 4          | 182064578  | 182064613 |
| X          | 104435106  | 104435140 |
| 14         | 70285576   | 70285601  |
| 6          | 73122084   | 73122123  |
| 8          | 70576141   | 70576184  |
| 13         | 36552821   | 36552860  |
| 3          | 164903700  | 164903728 | or portions or 1 to 4 bp sequences flanking the 5' end thereof,
and non-CBS regions set forth in the table 2 below:

| Chromosome | Start site | End site  |
|------------|------------|-----------|
| 7          | 68391104   | 68391132  |
| 7          | 136495924  | 136495948 |
| 2          | 57627616   | 57627640  |
| 16         | 8381278    | 8381302   |
| 5          | 23824204   | 23824224  |
| 7          | 67614923   | 67614943  |
| 8          | 65161396  | 65161420  |
| 7          | 4937707    | 4937736   |
| 12         | 126996666  | 126996686 |
| 4          | 5415060    | 5415082   |
| X          | 137405623  | 137405655 |
| 3          | 171164993  | 171165017 |
| 4          | 144748744  | 144748764 |
| 9          | 25481736   | 25481758  |
| 2          | 77150455   | 77150477  |
| 3          | 104801455  | 104801477 |
| X          | 125548690  | 125548710 |
| 14         | 83046706   | 83046744  | or portions or 1 to 4 bp sequences flanking the 5' end thereof, and
wherein detecting the presence of mutation in the CBS overlapping region(s), or portions or 1 to 4 bp sequences flanking the 5' end thereof, comprises contacting the biological sample with a primer having a sequence selected from the group consisting of: SEQ ID NO. 35, SEQ ID NO. 36, SEQ ID NO. 39, SEQ ID NO. 40, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 57, SEQ ID NO. 58, SEQ ID NO. 59, SEQ ID NO. 60, SEQ ID NO. 65, SEQ ID NO. 66, SEQ ID NO. 77, SEQ ID NO. 78, SEQ ID NO. SEQ ID NO. 83, SEQ ID NO. 84 and combinations thereof and/or wherein detecting the presence of mutation in the one or more focal regions comprises contacting the biological sample with a primer having a sequence selected from the group consisting of: SEQ ID NO. 37, SEQ ID NO. 38, SEQ ID NO. 41, SEQ ID NO. 42, SEQ ID NO. 43, SEQ ID NO. 44, SEQ ID NO. 53, SEQ ID NO. 54, SEQ ID NO. 55, SEQ ID NO. 56, SEQ ID NO. 61, SEQ ID NO. 62, SEQ ID NO. 63, SEQ ID NO. 64, SEQ ID NO. 67, SEQ ID NO. 68, SEQ ID NO. 71, SEQ ID NO. 72, SEQ ID NO. 75, SEQ ID NO. 76, SEQ ID NO. 81, SEQ ID NO. 82, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, and combinations thereof; and
   iv) detecting, determining, and/or diagnosing the presence of gastrointestinal cancer in the subject based on the presence of mutation in the one or more focal regions.

2. The method of claim 1, further comprising determining in the fluid biological sample of the subject, whether mutation is present in at least one of the genes selected from the group consisting of: KRAS, TP53, RHOA, ARID1A, PIK3CA, ERBB3 and PTEN, wherein presence of mutation in at least one of the genes is indicative of a risk of gastrointestinal cancer in the subject.

3. The method of claim 1, wherein detecting the presence of mutation in the one or more focal regions does not comprise determining whether mutation is present in a region spanning more than 50 nucleotides.

4. The method of claim 1, wherein the method further comprises determining whether mutation is present in at least two of the CBS overlapping regions, or portions or flanking sequences thereof, set forth in the table 1, optionally wherein the method comprises determining whether mutation is present in all of the CBS overlapping regions, or portions or 1 to 4 bp sequences flanking the 5' end thereof, set forth in the table 1, further optionally wherein the method comprises determining whether mutation is present in all of the CBS overlapping regions, or portions or 1 to 4 bp sequences flanking the 5' end thereof, and all of the non-CBS regions, or portions or 1 to 4 bp sequences flanking the 5' end thereof, set forth in the tables 1 and 2.

5. The method of claim 1, wherein the gastrointestinal cancer is selected from the group consisting of gastric cancer, colorectal cancer, colon cancer rectal cancer, esophageal cancer, liver cancer and pancreatic cancer.

6. The method of claim 1, wherein the human subject is an Asian subject.

7. The method of claim 1, wherein the nucleic acid is DNA.

8. A method of treating gastrointestinal cancer in a human subject, the method comprising:

a) detecting and/or determining the presence of gastrointestinal cancer in a human, wherein the detecting and/or determining comprises the steps of:
contacting a fluid biological sample from the subject with an agent for detecting the presence of a mutation in one or more focal regions with high mutation rates, wherein the fluid biological sample is selected from the group consisting of blood, plasma, serum, and combinations thereof,
detecting and/or determining the presence of the mutation in one or more focal regions with high mutation rates, wherein the one or more focal regions is selected from the group consisting of
CTCF-binding sites (CBS) overlapping regions set forth in the table 1 below:

| Chromosome | Start site | End site |
|---|---|---|
| 6 | 50570094 | 50570120 |
| 8 | 71000992 | 71001012 |
| 1 | 209422184 | 209422222 |
| 2 | 49173770 | 49173816 |
| 4 | 182064578 | 182064613 |
| X | 104435106 | 104435140 |
| 14 | 70285576 | 70285601 |
| 6 | 73122084 | 73122123 |
| 8 | 70576141 | 70576184 |
| 13 | 36552821 | 36552860 |
| 3 | 164903700 | 164903728 | or portions or 1 to 4 bp sequences flanking the 5' end thereof,
and non-CBS regions set forth in the table 2 below:

| Chromosome | Start site | End site |
|---|---|---|
| 7 | 68391104 | 68391132 |
| 7 | 136495924 | 136495948 |
| 2 | 57627616 | 57627640 |
| 16 | 8381278 | 8381302 |
| 5 | 23824204 | 23824224 |
| 7 | 67614923 | 67614943 |
| 8 | 65161396 | 65161420 |
| 7 | 4937707 | 4937736 |
| 12 | 126996666 | 126996686 |
| 4 | 5415060 | 5415082 |
| X | 137405623 | 137405655 |
| 3 | 171164993 | 171165017 |
| 4 | 144748744 | 144748764 |
| 9 | 25481736 | 25481758 |
| 2 | 77150455 | 77150477 |
| 3 | 104801455 | 104801477 |
| X | 125548690 | 125548710 |
| 14 | 83046706 | 83046744 | or portions or 1 to 4 bp sequences flanking the 5' end thereof,
wherein detecting and/or determining the presence of mutation in the CBS overlapping region(s), or portions or 1 to 4 bp sequences flanking the 5' end thereof, comprises contacting the biological sample with a primer having a sequence selected from the group consisting of: SEQ ID NO. 35, SEQ ID NO. 36, SEQ ID NO. 39, SEQ ID NO. 40, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 57, SEQ ID NO. 58, SEQ ID NO. 59, SEQ ID NO. 60, SEQ ID NO. 65, SEQ ID NO. 66, SEQ ID NO. 77, SEQ ID NO. 78, SEQ ID NO. SEQ ID NO. 83, SEQ ID NO. 84 and combinations thereof and/or wherein detecting and/or determining the presence of mutation in the one or more focal regions comprises contacting the biological sample with a primer having a sequence selected from the group consisting of: SEQ ID NO. 37, SEQ ID NO. 38, SEQ ID NO. 41, SEQ ID NO. 42, SEQ ID NO. 43, SEQ ID NO. 44, SEQ ID NO. 53, SEQ ID NO. 54, SEQ ID NO. 55, SEQ ID NO. 56, SEQ ID NO. 61, SEQ ID NO. 62, SEQ ID NO. 63, SEQ ID NO. 64, SEQ ID NO. 67, SEQ ID NO. 68, SEQ ID NO. 71, SEQ ID NO. 72, SEQ ID NO. 75, SEQ ID NO. 76, SEQ ID NO. 81, SEQ ID NO. 82, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, and combinations thereof,
wherein presence of mutation in the one or more focal regions detects and/or determines the presence of gastrointestinal cancer in the subject,
and
b) treating the subject detected and/or determined to have gastrointestinal cancer with a therapeutic agent for treating gastrointestinal cancer.

9. The method of claim 8, further comprising determining in the fluid biological sample of the subject, whether mutation is present in at least one of the genes selected from the group consisting of: KRAS, TP53, RHOA, ARID1A, PIK3CA, ERBB3 and PTEN, wherein when the biological sample shows a presence of mutation in one or more focal regions and/or at least one of the genes, the subject is administered a therapeutic agent for treating gastrointestinal cancer.

10. The method of claim 8, wherein the therapeutic agent is selected from the group consisting of chemotherapy, radiation therapy, immunotherapy and combinations thereof.

* * * * *

SEQUENCE LISTING

<160> NUMBER OF SEQ ID NOS: 95

<210> SEQ ID NO 1
<211> LENGTH: 27
<212> TYPE: DNA
<213> ORGANISM: Homo sapiens

<400> SEQUENCE: 1
ctctagtgga attttttcag tactgca           27

<210> SEQ ID NO 2
<211> LENGTH: 29
<212> TYPE: DNA
<213> ORGANISM: Homo sapiens

<400> SEQUENCE: 2 ggatttttt aaaaaaaatt ttttttat           29

<210> SEQ ID NO 3
<211> LENGTH: 21
<212> TYPE: DNA
<213> ORGANISM: Homo sapiens

<400> SEQUENCE: 3
ctggcaaaac ttcggtgcca a                                              21

<210> SEQ ID NO 4
<211> LENGTH: 25
<212> TYPE: DNA
<213> ORGANISM: Homo sapiens

<400> SEQUENCE: 4
tactggctta agttttggcc cagca                                          25

<210> SEQ ID NO 5
<211> LENGTH: 25
<212> TYPE: DNA
<213> ORGANISM: Homo sapiens

<400> SEQUENCE: 5
atttttccaa aaattttgc aatta                                           25

<210> SEQ ID NO 6
<211> LENGTH: 39
<212> TYPE: DNA
<213> ORGANISM: Homo sapiens

<400> SEQUENCE: 6
aggtcctttg ttgccaccta gtggccatta attgcacta                           39

<210> SEQ ID NO 7
<211> LENGTH: 47
<212> TYPE: DNA
<213> ORGANISM: Homo sapiens

<400> SEQUENCE: 7
tagcctgtag ttacttgatt tcaccactag atggtgatct tgtatta                  47

<210> SEQ ID NO 8
<211> LENGTH: 21
<212> TYPE: DNA
<213> ORGANISM: Homo sapiens

<400> SEQUENCE: 8
aggagagtac gtgcatgtgt g                                              21

<210> SEQ ID NO 9
<211> LENGTH: 36
<212> TYPE: DNA
<213> ORGANISM: Homo sapiens

<400> SEQUENCE: 9
cgcaacctac aaaactgcca ccaggtggcg ctcacg                              36

<210> SEQ ID NO 10
<211> LENGTH: 35
<212> TYPE: DNA
<213> ORGANISM: Homo sapiens

<400> SEQUENCE: 10
cagctcgccc tctagtggta attttatgaa ttgcc                               35

<210> SEQ ID NO 11
<211> LENGTH: 25
<212> TYPE: DNA

<213> ORGANISM: Homo sapiens

<400> SEQUENCE: 11
aataaataaa taaacaaaca aacaa    25

<210> SEQ ID NO 12
<211> LENGTH: 21
<212> TYPE: DNA
<213> ORGANISM: Homo sapiens

<400> SEQUENCE: 12
agcaagccta agtgtggtct g    21

<210> SEQ ID NO 13
<211> LENGTH: 21
<212> TYPE: DNA
<213> ORGANISM: Homo sapiens

<400> SEQUENCE: 13
tgagagaaac ttagggtttc a    21

<210> SEQ ID NO 14
<211> LENGTH: 26
<212> TYPE: DNA
<213> ORGANISM: Homo sapiens

<400> SEQUENCE: 14
tgcacttata aattctacca ccagag    26

<210> SEQ ID NO 15
<211> LENGTH: 40
<212> TYPE: DNA
<213> ORGANISM: Homo sapiens

<400> SEQUENCE: 15
gtggcgcatc tcagccacaa gatggcagca gtgcttcgtg    40

<210> SEQ ID NO 16
<211> LENGTH: 25
<212> TYPE: DNA
<213> ORGANISM: Homo sapiens

<400> SEQUENCE: 16
cataatctga aaattttgc aaaga    25

<210> SEQ ID NO 17
<211> LENGTH: 30
<212> TYPE: DNA
<213> ORGANISM: Homo sapiens

<400> SEQUENCE: 17
tgctggctta agttcagggc cacgctgccc    30

<210> SEQ ID NO 18
<211> LENGTH: 44
<212> TYPE: DNA
<213> ORGANISM: Homo sapiens

<400> SEQUENCE: 18
gtgttttcca aaatgaccac taggtggtag tctagttcaa ctaa    44

<210> SEQ ID NO 19
<211> LENGTH: 21

```
<212> TYPE: DNA
<213> ORGANISM: Homo sapiens

<400> SEQUENCE: 19
gtaagaaaac ttaggtgtaa a                                              21

<210> SEQ ID NO 20
<211> LENGTH: 21
<212> TYPE: DNA
<213> ORGANISM: Homo sapiens

<400> SEQUENCE: 20
aagaagtaca agactttgag g                                              21

<210> SEQ ID NO 21
<211> LENGTH: 23
<212> TYPE: DNA
<213> ORGANISM: Homo sapiens

<400> SEQUENCE: 21
ttttagctga agttcagtgg aat                                            23

<210> SEQ ID NO 22
<211> LENGTH: 21
<212> TYPE: DNA
<213> ORGANISM: Homo sapiens

<400> SEQUENCE: 22 gattttttt taaaaagtta t                                               21

<210> SEQ ID NO 23
<211> LENGTH: 33
<212> TYPE: DNA
<213> ORGANISM: Homo sapiens

<400> SEQUENCE: 23
tatctcacta ataaggaag aattcatcac ttt                                  33

<210> SEQ ID NO 24
<211> LENGTH: 40
<212> TYPE: DNA
<213> ORGANISM: Homo sapiens

<400> SEQUENCE: 24
taatatcaca attcgccact tggtgtcact agacctccag                          40

<210> SEQ ID NO 25
<211> LENGTH: 21
<212> TYPE: DNA
<213> ORGANISM: Homo sapiens

<400> SEQUENCE: 25 ctttttttt aaaaaaaag c                                                21

<210> SEQ ID NO 26
<211> LENGTH: 25
<212> TYPE: DNA
<213> ORGANISM: Homo sapiens

<400> SEQUENCE: 26
aataaataaa taaacaaaca aacat                                          25

<210> SEQ ID NO 27
```

```
<211> LENGTH: 21
<212> TYPE: DNA
<213> ORGANISM: Homo sapiens

<400> SEQUENCE: 27
aattttgttt gtttatttat t                                            21

<210> SEQ ID NO 28
<211> LENGTH: 29
<212> TYPE: DNA
<213> ORGANISM: Homo sapiens

<400> SEQUENCE: 28
aatggcctac ttagataagt gcctgcctc                                    29

<210> SEQ ID NO 29
<211> LENGTH: 21
<212> TYPE: DNA
<213> ORGANISM: Homo sapiens

<400> SEQUENCE: 29
ctggtcagag agcaggagga a                                            21

<210> SEQ ID NO 30
<211> LENGTH: 23
<212> TYPE: DNA
<213> ORGANISM: Homo sapiens

<400> SEQUENCE: 30
ttcacctaaa acttatcccc tta                                          23

<210> SEQ ID NO 31
<211> LENGTH: 23
<212> TYPE: DNA
<213> ORGANISM: Homo sapiens

<400> SEQUENCE: 31
atttgtagaa agtttgtgag ctg                                          23

<210> SEQ ID NO 32
<211> LENGTH: 23
<212> TYPE: DNA
<213> ORGANISM: Homo sapiens

<400> SEQUENCE: 32
aatggagtca agttttctga aat                                          23

<210> SEQ ID NO 33
<211> LENGTH: 21
<212> TYPE: DNA
<213> ORGANISM: Homo sapiens

<400> SEQUENCE: 33
ttgacagaac ttgttacatt t                                            21

<210> SEQ ID NO 34
<211> LENGTH: 39
<212> TYPE: DNA
<213> ORGANISM: Homo sapiens

<400> SEQUENCE: 34
ttggacaaac ttgacttaaa taataggcaa gggacacct                         39
```

<210> SEQ ID NO 35
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 35
cctgtccagg tattagagaa gg                                    22

<210> SEQ ID NO 36
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 36
aacccctcca cctcctttt                                        20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 37
ctgacttgca ccactcatgc                                       20

<210> SEQ ID NO 38
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 38
gatgggagga ctgtttgagg                                       20

<210> SEQ ID NO 39
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 39
ttctcctgca atgtttctcg                                       20

<210> SEQ ID NO 40
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 40
tcaccttatt tgactgcttt gc                                    22

<210> SEQ ID NO 41
<211> LENGTH: 20
<212> TYPE: DNA
<213> ORGANISM: Artificial Sequence
<220> FEATURE:
<223> OTHER INFORMATION: oligonucleotide sequence -continued

<400> SEQUENCE: 41
ccatgcagtg gttacagtgg                                             20

<210> SEQ ID NO 42
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 42
agaggtggtg gaggtgattg                                             20

<210> SEQ ID NO 43
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 43
agagcaggat aaggcatatt ca                                          22

<210> SEQ ID NO 44
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 44
tgggacattt tccctttcaa                                             20

<210> SEQ ID NO 45
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 45
cactgcctac agccaataat ca                                          22

<210> SEQ ID NO 46
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 46
accctgcctt ttctttcatt                                             20

<210> SEQ ID NO 47
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 47
ggggtgcaga gaagaatctg                                             20

<210> SEQ ID NO 48
<211> LENGTH: 20

```
<212> TYPE: DNA
<213> ORGANISM: Artificial Sequence
<220> FEATURE:
<223> OTHER INFORMATION: oligonucleotide sequence

<400> SEQUENCE: 48
atgccaccct tgttagtgg                                                    20

<210> SEQ ID NO 49
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 49
ctttgcgtgg tgaaaagaaa                                                   20

<210> SEQ ID NO 50
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 50
ttgctgctgc tccaaagtta                                                   20

<210> SEQ ID NO 51
<211> LENGTH: 21
<212> TYPE: DNA
<213> ORGANISM: Artificial Sequence
<220> FEATURE:
<223> OTHER INFORMATION: oligonucleotide sequence

<400> SEQUENCE: 51
ccagcagttg gtcaatgata a                                                 21

<210> SEQ ID NO 52
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 52
gctaaaaggg caattgttgg                                                   20

<210> SEQ ID NO 53
<211> LENGTH: 24
<212> TYPE: DNA
<213> ORGANISM: Artificial Sequence
<220> FEATURE:
<223> OTHER INFORMATION: oligonucleotide sequence

<400> SEQUENCE: 53
tgatgtctgt gatgttttca agtg                                              24

<210> SEQ ID NO 54
<211> LENGTH: 21
<212> TYPE: DNA
<213> ORGANISM: Artificial Sequence
<220> FEATURE:
<223> OTHER INFORMATION: oligonucleotide sequence

<400> SEQUENCE: 54
```

```
tgtcaattttgagccctcatc                                              21

<210> SEQ ID NO 55
<211> LENGTH: 21
<212> TYPE: DNA
<213> ORGANISM: Artificial Sequence
<220> FEATURE:
<223> OTHER INFORMATION: oligonucleotide sequence

<400> SEQUENCE: 55 ttggaactccctaccccctaaa                                             21

<210> SEQ ID NO 56
<211> LENGTH: 21
<212> TYPE: DNA
<213> ORGANISM: Artificial Sequence
<220> FEATURE:
<223> OTHER INFORMATION: oligonucleotide sequence

<400> SEQUENCE: 56 catggataaccagcacagaca                                              21

<210> SEQ ID NO 57
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 57 ggtagggcacttgctgtgtt                                               20

<210> SEQ ID NO 58
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 58 ctgcacctaagggacagcag                                               20

<210> SEQ ID NO 59
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 59 ctgccctctgttggtgagag                                               20

<210> SEQ ID NO 60
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 60 tagcgcatcagcattgactc                                               20

<210> SEQ ID NO 61
<211> LENGTH: 21
<212> TYPE: DNA
<213> ORGANISM: Artificial Sequence
```

```
<220> FEATURE:
<223> OTHER INFORMATION: oligonucleotide sequence

<400> SEQUENCE: 61
aaatggactc tctgccactg a                                              21

<210> SEQ ID NO 62
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 62
caggacaaag agacaagtgg ag                                             22

<210> SEQ ID NO 63
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 63
tgccttctaa accctcctga                                                20

<210> SEQ ID NO 64
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 64
gtctttgtga tggcccatgt                                                20

<210> SEQ ID NO 65
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 65
aagagcatca ccccatcaag                                                20

<210> SEQ ID NO 66
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 66
ctggagccaa gcaaagatgt                                                20

<210> SEQ ID NO 67
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 67 ctgctgccctt tatgttgaaa tg                                            22
```

```
<210> SEQ ID NO 68
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 68
gcaaaaccag gaagaagcag                                                   20

<210> SEQ ID NO 69
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 69
cagggctttg aggatggtag                                                   20

<210> SEQ ID NO 70
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 70
ctgggaatta gctcgcaaag                                                   20

<210> SEQ ID NO 71
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 71
caaggaacaa agagcccaac                                                   20

<210> SEQ ID NO 72
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 72
atggagaagg cagagcttca                                                   20

<210> SEQ ID NO 73
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 73
gcttccaggc taaagcacaa                                                   20

<210> SEQ ID NO 74
<211> LENGTH: 21
<212> TYPE: DNA
<213> ORGANISM: Artificial Sequence
<220> FEATURE:
<223> OTHER INFORMATION: oligonucleotide sequence
```

<400> SEQUENCE: 74
tccaggctat gtgaatgttg a                                              21

<210> SEQ ID NO 75
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 75
tggacatggt aggtccttga                                                20

<210> SEQ ID NO 76
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 76
tgtggtccca tatggacttg                                                20

<210> SEQ ID NO 77
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 77
gaacactctc aaacaaccaa ca                                             22

<210> SEQ ID NO 78
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 78
aatggggcct tacagaaaaa                                                20

<210> SEQ ID NO 79
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 79
ccagacatta ttggacttcc tg                                             22

<210> SEQ ID NO 80
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 80
tcattcccaa atcactgtca                                                20

<210> SEQ ID NO 81

```
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 81
cactccagcc tgggtaacag                                                    20

<210> SEQ ID NO 82
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 82
gctatttggg gattaacagt ga                                                 22

<210> SEQ ID NO 83
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 83
gggtctgtgg atctctggaa                                                    20

<210> SEQ ID NO 84
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 84
ccggtatcaa attggtggag                                                    20

<210> SEQ ID NO 85
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 85
tcatcagcac cagaaaccag                                                    20

<210> SEQ ID NO 86
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 86
tggattctaa tgggggaaaa                                                    20

<210> SEQ ID NO 87
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 87
```
catgaaacct cttgcaacca 20

<210> SEQ ID NO 88
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 88
ggctctgttt aacaaccagc tc 22

<210> SEQ ID NO 89
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 89
acacagccaa actgcatcaa 20

<210> SEQ ID NO 90
<211> LENGTH: 22
<212> TYPE: DNA
<213> ORGANISM: Artificial Sequence
<220> FEATURE:
<223> OTHER INFORMATION: oligonucleotide sequence

<400> SEQUENCE: 90
aactatgggt tgctcttgct tt 22

<210> SEQ ID NO 91
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 91
gccacattca aagccattct 20

<210> SEQ ID NO 92
<211> LENGTH: 20
<212> TYPE: DNA
<213> ORGANISM: Artificial Sequence
<220> FEATURE:
<223> OTHER INFORMATION: oligonucleotide sequence

<400> SEQUENCE: 92
ctcaaggtgt cccttgccta 20

<210> SEQ ID NO 93
<211> LENGTH: 24
<212> TYPE: DNA
<213> ORGANISM: Artificial Sequence
<220> FEATURE:
<223> OTHER INFORMATION: oligonucleotide sequence
<220> FEATURE:
<221> NAME/KEY: mutation
<222> LOCATION: (11)..(11)
<223> OTHER INFORMATION: G
<220> FEATURE:
<221> NAME/KEY: mutation
<222> LOCATION: (18)..(18)
<223> OTHER INFORMATION: C
<220> FEATURE:

<221> NAME/KEY: mutation
<222> LOCATION: (20)..(20)
<223> OTHER INFORMATION: G
<220> FEATURE:
<221> NAME/KEY: mutation
<222> LOCATION: (21)..(21)
<223> OTHER INFORMATION: G, C
<220> FEATURE:
<221> NAME/KEY: mutation
<222> LOCATION: (22)..(22)
<223> OTHER INFORMATION: G, C, A
<220> FEATURE:
<221> NAME/KEY: mutation
<222> LOCATION: (24)..(24)
<223> OTHER INFORMATION: A

<400> SEQUENCE: 93 gtgcccctc tagtggaatt tttt                                          24

<210> SEQ ID NO 94
<211> LENGTH: 20
<212> TYPE: DNA
<213> ORGANISM: Artificial sequence
<220> FEATURE:
<223> OTHER INFORMATION: oligonucleotide sequence
<220> FEATURE:
<221> NAME/KEY: mutation
<222> LOCATION: (1)..(1)
<223> OTHER INFORMATION: C
<220> FEATURE:
<221> NAME/KEY: mutation
<222> LOCATION: (10)..(10)
<223> OTHER INFORMATION: C, G
<220> FEATURE:
<221> NAME/KEY: mutation
<222> LOCATION: (12)..(12)
<223> OTHER INFORMATION: C, G, T
<220> FEATURE:
<221> NAME/KEY: mutation
<222> LOCATION: (20)..(20)
<223> OTHER INFORMATION: G

<400> SEQUENCE: 94
tcagccacaa gatggcagca                                              20

<210> SEQ ID NO 95
<211> LENGTH: 21
<212> TYPE: DNA
<213> ORGANISM: Artificial sequence
<220> FEATURE:
<223> OTHER INFORMATION: oligonucleotide sequence
<220> FEATURE:
<221> NAME/KEY: mutation
<222> LOCATION: (1)..(1)
<223> OTHER INFORMATION: T
<220> FEATURE:
<221> NAME/KEY: mutation
<222> LOCATION: (2)..(2)
<223> OTHER INFORMATION: G
<220> FEATURE:
<221> NAME/KEY: mutation
<222> LOCATION: (10)..(10)
<223> OTHER INFORMATION: G, C
<220> FEATURE:
<221> NAME/KEY: mutation
<222> LOCATION: (12)..(12)
<223> OTHER INFORMATION: A
<220> FEATURE:
<221> NAME/KEY: mutation
<222> LOCATION: (20)..(20)
<223> OTHER INFORMATION: G

```
<400> SEQUENCE: 95
attcgccact tggtgtcact a                                              21
```